US009790178B2

(12) United States Patent
Allen et al.

(10) Patent No.: US 9,790,178 B2
(45) Date of Patent: Oct. 17, 2017

(54) PYRROLIDINYL UREA, THIOUREA, GUANIDINE AND CYANOGUANIDINE COMPOUNDS AS TRKA KINASE INHIBITORS

(71) Applicant: Array BioPharma Inc., Boulder, CO (US)

(72) Inventors: Shelley Allen, Boulder, CO (US); Steven Wade Andrews, Boulder, CO (US); James F. Blake, Boulder, CO (US); Barbara J. Brandhuber, Boulder, CO (US); Yutong Jiang, Boulder, CO (US); Timothy Kercher, San Diego, CA (US); Shannon L. Winski, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 82 days.

(21) Appl. No.: 14/442,514

(22) PCT Filed: Nov. 13, 2013

(86) PCT No.: PCT/US2013/069827
§ 371 (c)(1),
(2) Date: May 13, 2015

(87) PCT Pub. No.: WO2014/078372
PCT Pub. Date: May 22, 2014

(65) Prior Publication Data
US 2016/0297758 A1 Oct. 13, 2016

Related U.S. Application Data

(60) Provisional application No. 61/725,940, filed on Nov. 13, 2012.

(51) Int. Cl.

| | |
|---|---|
| ***C07D 491/02*** | (2006.01) |
| ***C07D 487/00*** | (2006.01) |
| ***A61K 31/50*** | (2006.01) |
| ***A61K 31/519*** | (2006.01) |
| ***A61K 31/44*** | (2006.01) |
| ***C07D 207/50*** | (2006.01) |
| ***C07D 403/12*** | (2006.01) |
| ***C07D 471/04*** | (2006.01) |
| ***C07D 487/04*** | (2006.01) |
| ***C07D 207/14*** | (2006.01) |

(Continued)

(52) U.S. Cl.
CPC ............ *C07D 207/50* (2013.01); *C07C 53/18* (2013.01); *C07D 207/14* (2013.01); *C07D 403/12* (2013.01); *C07D 471/04* (2013.01); *C07D 487/04* (2013.01); *C07D 513/04* (2013.01)

(58) Field of Classification Search
CPC .. C07D 471/04; C07D 487/04; A61K 31/437; A61K 31/4985; A61K 31/519
USPC ...... 546/121; 544/281, 350; 514/249, 259.1, 514/300
See application file for complete search history.

(56) References Cited

U.S. PATENT DOCUMENTS

| | | | |
|---|---|---|---|
| 5,849,779 | A | 12/1998 | Hirota et al. |
| 5,998,424 | A | 12/1999 | Galemmo, Jr. et al. |

(Continued)

FOREIGN PATENT DOCUMENTS

| | | | |
|---|---|---|---|
| EP | 0761658 | A1 | 12/1997 |
| EP | 1043995 | B1 | 11/2006 |

(Continued)

OTHER PUBLICATIONS

Tsuzuki, Y., et al., Tetrahedron Asymmetry 12 (2001), 2989-2997.

(Continued)

*Primary Examiner* — Shengjun Wang
(74) *Attorney, Agent, or Firm* — Viksnins Harris Padys Malen LLP

(57) ABSTRACT

Compounds of Formula I: or stereoisomers, tautomers, or pharmaceutically acceptable salts, or solvates or prodrugs thereof, where $R^1$, $R^2$, $R^a$, $R^b$, $R^c$, $R^d$, X, Ring B, and Ring C are as defined herein, and wherein Ring B moiety and the NH—C(=X)—NH moiety are in the trans configuration, are inhibitors of TrkA kinase and are useful in the treatment of diseases which can be treated with a TrkA kinase inhibitor such as pain, cancer, inflammation/inflammatory diseases, neurodegenerative diseases, certain infectious diseases, Sjogren's syndrome, endometriosis, diabetic peripheral neuropathy, prostatitis and pelvic pain syndrome.

I

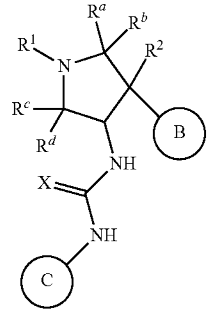

6 Claims, No Drawings

(51) Int. Cl.
*C07D 513/04* (2006.01)
*C07C 53/18* (2006.01)

(56) References Cited

U.S. PATENT DOCUMENTS

| | | | | |
|---|---|---|---|---|
| 6,197,798 | B1 | 3/2001 | Fink et al. | |
| 6,410,533 | B1 | 6/2002 | Hirth et al. | |
| 7,223,782 | B2 | 5/2007 | Atkinson et al. | |
| 7,625,915 | B2 | 12/2009 | Dumas et al. | |
| 8,592,454 | B2 | 11/2013 | Shirai et al. | |
| 9,163,917 | B2 | 10/2015 | Hidaka | |
| 2011/0178060 | A1* | 7/2011 | Shirai | C07D 403/06 514/210.18 |

FOREIGN PATENT DOCUMENTS

| | | | |
|---|---|---|---|
| EP | 2033955 | A1 | 3/2009 |
| EP | 1451160 | B1 | 1/2010 |
| EP | 2336105 | B9 | 9/2014 |
| JP | 2005206527 | A | 8/2005 |
| WO | 9804521 | A1 | 2/1998 |
| WO | 9923091 | A1 | 5/1999 |
| WO | 9932110 | A1 | 7/1999 |
| WO | 0039116 | A1 | 7/2000 |
| WO | 0043384 | A1 | 7/2000 |
| WO | 0112188 | A1 | 2/2001 |
| WO | 0202525 | A2 | 1/2002 |
| WO | 02088101 | A2 | 11/2002 |
| WO | 02090326 | A1 | 11/2002 |
| WO | 03037274 | A2 | 5/2003 |
| WO | 03045920 | A1 | 6/2003 |
| WO | 03051275 | A2 | 6/2003 |
| WO | 2004005262 | A2 | 1/2004 |
| WO | 2004032870 | A2 | 4/2004 |
| WO | 2004060305 | A2 | 7/2004 |
| WO | 2004060306 | A2 | 7/2004 |
| WO | 2004061084 | A2 | 7/2004 |
| WO | 2004111009 | A1 | 12/2004 |
| WO | 2005024755 | A2 | 3/2005 |
| WO | 2005048948 | A2 | 6/2005 |
| WO | 2005110994 | A2 | 11/2005 |
| WO | 2006014290 | A2 | 2/2006 |
| WO | 2006068591 | A1 | 6/2006 |
| WO | 2006070198 | A1 | 7/2006 |
| WO | 2006071940 | A2 | 7/2006 |
| WO | 2006081034 | A2 | 8/2006 |
| WO | 2006123257 | A2 | 11/2006 |
| WO | 2007008917 | A2 | 1/2007 |
| WO | 2007059202 | A2 | 5/2007 |
| WO | 2007061882 | A2 | 5/2007 |
| WO | 2007064872 | A2 | 6/2007 |
| WO | 2008016811 | A2 | 2/2008 |
| WO | 2008021859 | A1 | 2/2008 |
| WO | 2008033999 | A2 | 3/2008 |
| WO | 2008034008 | A2 | 3/2008 |
| WO | 2008046003 | A2 | 4/2008 |
| WO | 2008131276 | A1 | 10/2008 |
| WO | 2008150899 | A1 | 12/2008 |
| WO | 2009140128 | A2 | 11/2009 |
| WO | 2010032856 | A1 | 3/2010 |
| WO | 2010033941 | A1 | 3/2010 |
| WO | 2010040663 | A1 | 4/2010 |
| WO | 2010048314 | A1 | 4/2010 |
| WO | 2010059719 | A2 | 5/2010 |
| WO | 2010075376 | A2 | 7/2010 |
| WO | 2010077680 | A2 | 7/2010 |
| WO | 2010104488 | A1 | 9/2010 |
| WO | 2010125799 | A1 | 11/2010 |
| WO | 2011006074 | A1 | 1/2011 |
| WO | 2011032291 | A1 | 3/2011 |
| WO | 2011146336 | A1 | 11/2011 |
| WO | 2012158413 | A2 | 11/2012 |
| WO | 2013063214 | A1 | 5/2013 |
| WO | 2013096226 | A1 | 6/2013 |
| WO | 2013176970 | A1 | 11/2013 |
| WO | 2014052563 | A1 | 4/2014 |
| WO | 2014052566 | A1 | 4/2014 |
| WO | 2014078322 | A1 | 5/2014 |
| WO | 2014078323 | A1 | 5/2014 |
| WO | 2014078325 | A1 | 5/2014 |
| WO | 2014078328 | A1 | 5/2014 |
| WO | 2014078331 | A1 | 5/2014 |
| WO | 2014078372 | A1 | 5/2014 |
| WO | 2014078378 | A1 | 5/2014 |
| WO | 2014078408 | A1 | 5/2014 |
| WO | 2014078417 | A1 | 5/2014 |
| WO | 2014078454 | A1 | 5/2014 |
| WO | 2015039333 | A1 | 3/2015 |
| WO | 2015042085 | A2 | 3/2015 |

OTHER PUBLICATIONS

Wadhwa, S., et al., Journal of Biosciences, 2003, 28(2), 181-188.
Wang, T., et al., Expert Opinion in Therapeutic Patents (2009) 19(3):305-319.
Woolf, C.J. et al. (1994) Neuroscience, 62, 327-331.
Yilmaz, T., et al., Cancer Biology and Therapy, 2010, 10(6), 644-653.
Zahn, P.K. et al. (2004) J. Pain, 5, 157-163.
Patent Cooperation Treaty, International Searching Authority, Search Report and Written Opinion for PCT/US2013/069827, May 28, 2015, 10 Pages.
Adriaenssens, E, et al. Cancer Res (2008) 68:(2) 346-351.
Asaumi, K., et al., Bone (2000) 26(6) 625-633.
Bardelli, A., Science 2003, 300, 949.
Bhattacharya, S. K., et al., Bioorganic & Medicinal Chemistry Letters (2012) 22(24) 7523-7592.
Bouhana, Karyn S., et al., "Comparison of Analgesic Effects of an Allosteric Inhibitor of TrkA to that of an ATP site inhibitor of the pan-Trk axis in a Rodent Model of Inflammatory Pain", Gordon Conference, Salve Regina University, Newport, RI, Jun. 7, 2011.
Brodeur, G. M., Nat. Rev. Cancer 2003, 3, 203-216.
Bruno, O., Bioorganic & Medicinal Chemistry (2009) 17, 3379-3387.
Burger, K., et al., Synthesis (1990) vol. 4, 360-365.
Chambers, L J., et al., Bioorganic & Medicinal Chemistry Letters (2010) 20(10) 3161-3164.
Davidson. B., et al., Clin. Cancer Res. 2003, 9, 2248-2259.
Davies, Stephen G., et al., Asymmetric synthesis of 3,4-anti- and 3,4-syn-substituted aminopyrrolidines via lithium amide conjugate addition, Org. Biomol. Chem., 2007, 5, 1961-1969.
Delafoy, L. et al. (2003) Pain 105, 489-497.
Demelo-Jorge, M. et al., Cell Host & Microbe (2007) 1(4), 251-261.
Dimola, F. F, et al., Gut (2000) 46(5), 670-678.
Dou, Y.-C., et. al. Archives of Dermatological Research (2006) 298(1), 31-37.
Du, et al., World Journal of Gastroenterology, 2003, 9(7), 1431-1434.
Eguchi, M., et aL, Blood 1999, 93 (4), pp. 1355-1363.
El Haddad, M., et al., J. Heterocyclic Chem., (2000) 37, 1247-1252.
Eliav, E. et al., Pain 79, 255-264 (1999).
Euthus, D.M., et al., Cancer Cell 2002, 2 (5), pp. 347-348.
Freund-Michel, V; Frossard, N., Pharmacology & Therapeutics (2008) 117(1), 52-76.
Greco, A., et al., Molecular and Cellular Endocrinology 2010, 321 (1), pp. 44-49.
Gruber-Olipitz, M., et al., Journal of Proteome Research 2008, 7 (5), pp. 1932-1944.
Gwak, Y. S. et al. (2003) Neurosci. Lett. 336, 117-120.
Han, S., et al., J. Biological Chem., (2009), 284(19) 13199-13201.
Herzberg, U. et al., Neuroreport 1997; 8:1613-1618.
Hu, Vivian Y; et al., The Journal of Urology (2005), 173(3), 1016-1021.
Jaggar, S. I. et al., Br. J. Anaesth. (1999) 83, 442-448.
Jin, W., et al., Carcinogenesis (2010) 31 (11), pp. 1939-1947.
Kaymakcioglu, B.K, et al., European Journal of Pharmaceutical Sciences (2005) 26(1), 97-103.
Lamb, K. et al. (2003) Neurogastroenterol. Motil. 15, 355-361.

(56) References Cited

OTHER PUBLICATIONS

Li, L. et al. (2003) Mol. Cell. Neurosci. 23, 232-250.
Li, Y.-G., et al., Chinese Journal of Cancer Prevention and Treatment, 2009, 16 (6), pp. 428-430 (with English Abstract).
Ma, Q. P. and Woolf, C. J. NeuroReport (1997) 8, 807-810.
Mantyh, Patrick W., et al., Anesthesiology, vol. 115, No. 1, Jul. 2011, 189-204.
McCarthy, C. and Walker, E., Expert Opin. Ther. Patents (2014) 24(7):731-744.
McMahon, S.B. et al., (1995) Nat. Med. 1, 774-780.
Meyer, J. et al. (2007) Leukemia, 21(10):2171-2180.
Nakagawara, A. (2001) Cancer Letters 169:107-114.
Patapoutian, A. et al., Current Opinion in Neurobiology, 2001, 11, 272-280.
Pierottia, M.A. and Greco A., (2006) Cancer Letters 232:90-98.
Pinski, J. et al., Cancer Research, (2002) 62:986-989.
Ramer, M. S. and Bisby, M. A. (1999) Eur. J. Neurosci. 11, 837-846.
Raychaudhuri, S. P., et al., J. Investigative Dermatology (2004) 122(3), 812-819.
Ricci A., et al., American Journal of Respiratory Cell and Molecular Biology, 2001, 25(4), pp. 439-446.
Ro, L. S. et aL, Pain, Feb. 1999; 79(2-3):265-274.
Shelton, D. L. et al. (2005) Pain, 116, 8-16.
Theodosiou, M. et al. (1999) Pain, 81, 245-255.
Truzzi, F., et al., Dermato-Endocrinology, 2011, 3(1), 32-36.

* cited by examiner

PYRROLIDINYL UREA, THIOUREA, GUANIDINE AND CYANOGUANIDINE COMPOUNDS AS TRKA KINASE INHIBITORS

RELATED APPLICATIONS

This application is a 371 filing of PCT Application No. PCT/US2013/069827, filed Nov. 13, 2013, which claims priority to U.S. Provisional Application Ser. No. 61/725,940, filed Nov. 13, 2012, each of which is incorporated herein by reference in its entirety.

BACKGROUND OF THE INVENTION

The present invention relates to novel compounds, to pharmaceutical compositions comprising the compounds, to processes for making the compounds and to the use of the compounds in therapy. More particularly, it relates to pyrrolidinyl urea, thiourea, guanidine and cyanoguanidine compounds which exhibit TrkA kinase inhibition, and which are useful in the treatment of pain, cancer, inflammation/inflammatory diseases, neurodegenerative diseases, certain infectious diseases, Sjogren's syndrome, endometriosis, diabetic peripheral neuropathy, prostatitis and pelvic pain syndrome.

The current treatment regimens for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., *Current Opinion in Neurobiology,* 2001, 11, 272-280).

Inhibitors of the Trk/neurotrophin pathway have been demonstrated to be effective in numerous pre-clinical animal models of pain. For example, antagonistic NGF and TrkA antibodies such as RN-624 have been shown to be efficacious in inflammatory and neuropathic pain animal models (Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *NeuroReport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J. Anaesth.* 83, 442-448) and neuropathic pain animal models (Ramer, M. S. and Bisby, M. A. (1999) *Eur. J. Neurosci.* 11, 837-846; Ro, L. S. et al. (1999); Herzberg, U. et al., *Pain* 79, 265-274 (1997) *Neuroreport* 8, 1613-1618; Theodosiou, M. et al. (1999) *Pain* 81, 245-255; Li, L. et al. (2003) *Mol. Cell. Neurosci.* 23, 232-250; Gwak, Y. S. et al. (2003) *Neurosci. Lett.* 336, 117-120).

It has also been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. Because TrkA kinase may serve as a mediator of NGF driven biological responses, inhibitors of TrkA and/or other Trk kinases may provide an effective treatment for chronic pain states.

Recent literature has also shown that overexpression, activation, amplification and/or mutation of Trk kinases are associated with many cancers including neuroblastoma (Brodeur, G. M., *Nat. Rev. Cancer* 2003, 3, 203-216), ovarian (Davidson. B., et al., *Clin. Cancer Res.* 2003, 9, 2248-2259), colorectal cancer (Bardelli, A., *Science* 2003, 300, 949), melanoma (Truzzi, F., et al., *Dermato-Endocrinology* 2008, 3 (1), pp. 32-36), head and neck cancer (Yilmaz, T., et al., *Cancer Biology and Therapy* 2010, 10 (6), pp. 644-653), gastric carcinoma (Du, J. et al., *World Journal of Gastroenterology* 2003, 9 (7), pp. 1431-1434), lung carcinoma (Ricci A., et al., *American Journal of Respiratory Cell and Molecular Biology* 25 (4), pp. 439-446), breast cancer (Jin, W., et al., *Carcinogenesis* 2010, 31 (11), pp. 1939-1947), Glioblastoma (Wadhwa, S., et al., *Journal of Biosciences* 2003, 28 (2), pp. 181-188), medulloblastoma (Gruber-Olipitz, M., et al., *Journal of Proteome Research* 2008, 7 (5), pp. 1932-1944), secratory breast cancer (Euthus, D. M., et al., *Cancer Cell* 2002, 2 (5), pp. 347-348), salivary gland cancer (Li, Y.-G., et al., *Chinese Journal of Cancer Prevention and Treatment* 2009, 16 (6), pp. 428-430), papillary thyroid carcinoma (Greco, A., et al., *Molecular and Cellular Endocrinology* 2010, 321 (1), pp. 44-49) and adult myeloid leukemia (Eguchi, M., et al., *Blood* 1999, 93 (4), pp. 1355-1363). In preclinical models of cancer, non-selective small molecule inhibitors of TrkA, B and C were efficacious in both inhibiting tumor growth and stopping tumor metastasis (Nakagawara, A. (2001) *Cancer Letters* 169:107-114; Meyer, J. et al. (2007) *Leukemia,* 1-10; Pierottia, M. A. and Greco A., (2006) *Cancer Letters* 232:90-98; Eric Adriaenssens, E., et al. *Cancer Res* (2008) 68:(2) 346-351).

In addition, inhibition of the neurotrophin/Trk pathway has been shown to be effective in treatment of pre-clinical models of inflammatory diseases with NGF antibodies or non-selective small molecule inhibitors of TrkA. For example, inhibition of the neurotrophin/Trk pathway has been implicated in preclinical models of inflammatory lung diseases including asthma (Freund-Michel, V; Frossard, N., *Pharmacology & Therapeutics* (2008) 117(1), 52-76), interstitial cystitis (Hu Vivian Y; et. al. *The Journal of Urology* (2005), 173(3), 1016-21), bladder pain syndrome (Liu, H.-T., et al., (2010) BJU International, 106 (11), pp. 1681-1685), inflammatory bowel diseases including ulcerative colitis and Crohn's disease (Di Mola, F. F, et. al., *Gut* (2000) 46(5), 670-678) and inflammatory skin diseases such as atopic dermatitis (Dou, Y.-C., et. al. *Archives of Dermatological Research* (2006) 298(1), 31-37), eczema and psoriasis (Raychaudhuri, S. P., et al., *J. Investigative Dermatology* (2004) 122(3), 812-819).

The TrkA receptor is also thought to be critical to the disease process of the parasitic infection of *Trypanosoma cruzi* (Chagas disease) in human hosts (de Melo-Jorge, M. et al., *Cell Host & Microbe* (2007) 1(4), 251-261).

Trk inhibitors may also find use in treating disease related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA receptors has been observed in the bone-forming area in mouse models of bone fracture (K. Asaumi, et al., *Bone* (2000) 26(6) 625-633). In addition, localization of NGF was observed in almost all bone-forming cells (K. Asaumi, et al.). Recently, it was demonstrated that a Trk inhibitor inhibits the signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Trk inhibitors may also find use in treating diseases and disorders such as Sjogren's syndrome (Fauchais, A. L., et al., (2009) Scandinavian Journal of Rheumatology, 38(1), pp. 50-57), endometriosis (Barcena De Arellano, M. L., et al., (2011) Reproductive Sciences, 18(12), pp. 1202-1210; Barcena De Arellano, et al., (2011) Fertility and Sterility, 95(3), pp. 1123-1126; Cattaneo, A., (2010) Current Opinion in Molecular Therapeutics, 12(1), pp. 94-106), diabetic peripheral neuropathy (Kim, H. C., et al., (2009) Diabetic Medicine, 26 (12), pp. 1228-1234; Siniscalco, D., et al., (2011) Current Neuropharmacology, 9(4), pp. 523-529; Ossipov, M. H., (2011) Current Pain and Headache Reports, 15(3), pp. 185-192), and prostatitis and pelvic pain syndrome (Watanabe, T., et al., (2011) BJU International, 108 (2), pp. 248-251; and Miller, L. J., et al., (2002) Urology, 59(4), pp. 603-608).

Several classes of small molecule inhibitors of Trk kinases said to be useful for treating pain or cancer are known (*Expert Opin. Ther. Patents* (2009) 19(3), 305-319).

International application publication WO 2010/032856 describes compounds represented by the formula

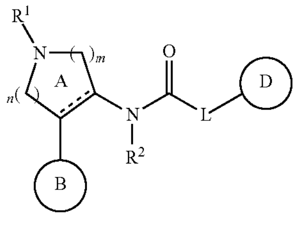

wherein ring B is an aromatic ring, ring D is an aromatic ring, and L is $NR^3$, $NR^3C(R^{4a}R^{4b})$, O or $OC(R^{4a}R^{4b})$, which are asserted to be tachykinin receptor antagonists.

SUMMARY OF THE INVENTION

It has now been found that pyrrolidinyl urea, thiourea, guanidine and cyanoguanidine compounds are inhibitors of TrkA, and useful for treating disorders and diseases such as pain, including chronic and acute pain. Compounds of the invention useful in the treatment of multiple types of pain including inflammatory pain, neuropathic pain, and pain associated with cancer, surgery, or bone fracture. In addition, compounds of the invention are useful for treating cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

More specifically, provided herein are compounds of Formula I:

I

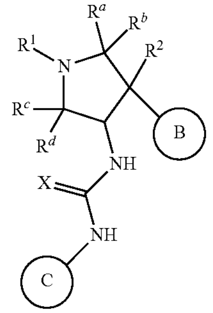

or stereoisomers, tautomers, or pharmaceutically acceptable salts, solvates or prodrugs thereof, wherein Ring B and the NH—C(═X)—NH moiety are in the trans configuration and $R^1$, $R^2$, $R^a$, $R^b$, $R^c$, $R^d$, X, Ring B and Ring C are as defined herein.

Another aspect of the present invention provides methods of treating a disease or disorder modulated by TrkA, comprising administering to a mammal in need of such treatment an effective amount of a compound of this invention or a stereoisomer, solvate or pharmaceutically acceptable salt thereof. In one embodiment, the disease and disorders include chronic and acute pain, including but not limited to inflammatory pain, neuropathic pain, and pain associated with cancer, surgery, or bone fracture. In another embodiment, the disease and disorders include, but are not limited to, cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases. In one embodiment, the treatment includes treating the mammal with a compound of this invention in combination with an additional therapeutic agent.

Another aspect of the present invention provides a pharmaceutical composition comprising a compound of the present invention or a pharmaceutically acceptable salt thereof.

Another aspect of the present invention provides the compounds of the present invention for use in therapy.

Another aspect of the present invention provides the compounds of the present invention for use in the treatment of disease and disorders such as chronic and acute pain, including but not limited to inflammatory pain, neuropathic pain, and pain associated with cancer, surgery, or bone fracture. Another aspect of the present invention provides the compounds of the present invention for use in the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides the use of a compound of this invention in the manufacture of a medicament for the treatment of disease and disorders such as chronic and acute pain including, but not limited to, inflammatory pain, neuropathic pain, and pain associated with cancer, surgery, or bone fracture.

Another aspect of the present invention provides the use of a compound of this invention in the manufacture of a medicament for the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides intermediates for preparing compounds of Formula I.

Another aspect of the present invention includes methods of preparing, methods of separation, and methods of purification of the compounds of this invention.

DETAILED DESCRIPTION OF THE INVENTION

Provided herein are compounds, and pharmaceutical formulations thereof, that are useful in the treatment of diseases, conditions and/or disorders modulated by TrkA.

A representative compound of the invention (See Table B below), was found to be highly selective for TrkA over a panel of about 230 other kinases at 10 μM concentration. In addition, compounds of the invention such as those shown in Table A below, were found to be at least 1000 fold more selective for TrkA versus p38α.

One embodiment provides a compound of Formula I:

I

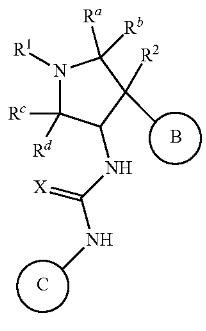

or stereoisomers, tautomers, or pharmaceutically acceptable salts, solvates or prodrugs thereof, wherein:

Ring B and the NH—C(═X)—NH moiety are in the trans configuration;

$R^a$, $R^b$, $R^c$ and $R^d$ are independently selected from H and (1-3C)alkyl, or $R^c$ and $R^d$ are independently selected from H and (1-3C)alkyl, and $R^a$ and $R^b$ together with the atom to which they are attached form a cyclopropyl ring;

X is O, S, NH or N—CN;

$R^1$ is (1-3C alkoxy)(1-6C)alkyl, (trifluoromethoxy)(1-6C) alkyl, (1-3C sulfanyl)(1-6C)alkyl, monofluoro(1-6C)alkyl, difluoro(1-6C)alkyl, trifluoro(1-6C)alkyl, tetrafluoro(2-6C) alkyl, pentafluro(2-6C)alkyl, cyano(1-6C)alkyl, aminocarbonyl(1-6C)alkyl, hydroxy(1-6C)alkyl, dihydroxy(2-6C) alkyl, (1-6C)alkyl, (1-3Calkylamino)(1-3C)alkyl, (1-4C alkoxycarbonyl)(1-6C)alkyl, amino(1-6C)alkyl, hydroxy(1-3C alkoxy)(1-6C)alkyl, di(1-3C alkoxy)(1-6C)alkyl, (1-3C alkoxy)trifluoro(1-6C)alkyl, hydroxytrifluoro(1-6C)alkyl, (1-4C alkoxycarbonyl)(1-3C alkoxy)(1-6C)alkyl, or hydroxycarbonyl(1-3C alkoxy)(1-6C)alkyl;

$R^2$ is H, F, or OH;

Ring B is $Ar^1$ or $hetAr^1$;

$Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN;

$hetAr^1$ is a 5-6 membered heteroaryl having 1-3 ring heteroatoms independently selected from N, S and O, and optionally substituted with one or more groups independently selected from (1-6C)alkyl, halogen, OH, $CF_3$, $NH_2$ and hydroxy(1-2C)alkyl;

Ring C is selected from formulas C-1 through C-9

C-1

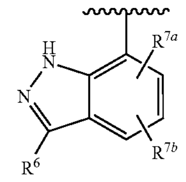

C-2

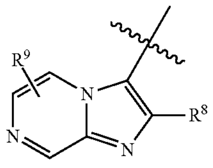

C-3

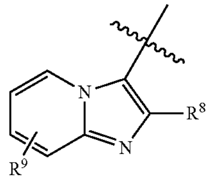

C-4

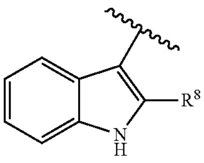

C-5

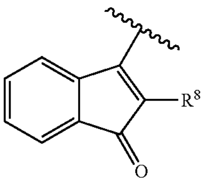

C-6

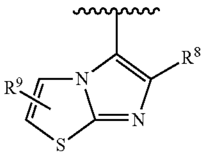

-continued

C-7

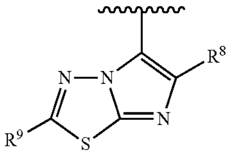

C-8

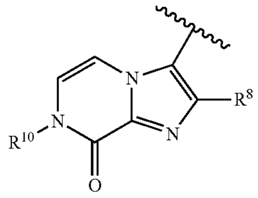

C-9

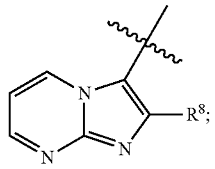

$R^6$ is H, halogen, or phenyl [optionally substituted with one or more substituents independently selected from halogen and (1-3C)alkyl];

$R^{7a}$ and $R^{7b}$ are independently H, (1-6C)alkyl, or phenyl [optionally substituted with one or more substituents independently selected from halogen and (1-3C)alkyl], wherein only one of $R^{7a}$ and $R^{7b}$ can be phenyl optionally substituted with one or more substituents independently selected from halogen and (1-3C)alkyl;

$R^8$ is phenyl optionally substituted with one or more substituents independently selected from halogen, (1-3C) alkyl and (3-6C)cycloalkyl;

$R^9$ is H, halogen, (1-6C)alkyl [optionally substituted with one to five fluoros] or (1-6C)alkoxy; and $R^{10}$ is H or (1-6C)alkyl.

It is to be understood that in instances where two or more radicals are used in succession to define a substituent attached to a structure, the first named radical is considered to be terminal and the last named radical is considered to be attached to the structure in question. Thus, for example, the radical "alkoxyalkyl" is attached to the structure in question by the alkyl group.

The terms "(1-6C)alkyl", "(1-4C)alkyl" and "(1-3C) alkyl" as used herein refer to saturated linear monovalent hydrocarbon radicals of one to six carbon atoms, one to four carbon atoms, and one to three carbon atoms, respectively, or a branched saturated monovalent hydrocarbon radical of three to six carbon atoms, three to four carbon atoms, or three carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

"(1-4C)Alkoxy", and "(1-6C)alkoxy" refer to an —OR radical where R is (1-4C)alkyl, or (1-6C)alkyl, respectively, as defined above. Examples include methoxy, ethoxy, and the like.

"(1-3C Alkoxy)(1-6C)alkyl" means a linear saturated monovalent hydrocarbon radical of one to six carbon atoms, or a branched saturated monovalent hydrocarbon radical of three to six carbon atoms, wherein one of the carbon atoms is substituted with one (1-3C)alkoxy group as defined herein.

"(1-4C Alkoxycarbonyl)(1-6C)alkyl" means a (1-6C) alkyl group as defined herein, wherein one of the carbons is substituted with a (1-4C alkoxy)carbonyl group as defined herein.

"(1-3C Alkoxy)trifluoro(1-6C)alkyl" means a (1-6C)alkyl group as defined herein, wherein one of the carbons is substituted with three fluoros, and another carbon is substituted with a (1-3C)alkoxy group as defined herein.

"(1-4C Alkoxycarbonyl)(1-3C alkoxy)(1-6C)alkyl" means a (1-3C alkoxy)(1-6C)alkyl group as defined herein wherein one of the carbon atoms is substituted with one (1-4C alkoxycarbonyl group, i.e., an alkyl-O—C(=O)— group.

"Amino(1-6C)alkyl" means a linear saturated monovalent hydrocarbon radical of one to six carbon atoms or a branched saturated monovalent hydrocarbon radical of three to six carbon atoms, wherein one of the carbon atoms is substituted with one —NRR' group where R and R' are independently selected from hydrogen or (1-3C)alkyl as defined herein. Examples include aminomethyl, methylaminoethyl, 2-ethylamino-2-methylethyl, and the like.

"Aminocarbonyl" means a RR'NCO— radical where R and R' are independently hydrogen or (1-6C)alkyl as defined herein. Examples include $H_2NCO$—, dimethylaminocarbonyl, and the like.

"Aminocarbonyl(1-6C)alkyl" means a linear saturated hydrocarbon radical of one to six carbon atoms or a branched saturated monovalent hydrocarbon radical of three to six carbons wherein one of the carbon atoms is substituted with one aminocarbonyl group as defined herein, e.g., 2-aminocarbonylethyl, 1-, 2-, or 3-dimethylaminocarbonylpropyl, and the like.

"Hydroxycarbonyl" means HOC(=O)—.

"Cyano(1-6C)alkyl" means a linear saturated hydrocarbon radical of one to six carbon atoms or a branched saturated monovalent hydrocarbon radical of three to six carbons substituted with a cyano (CN) group.

"(3-6C)Cycloalkyl" means a cyclic saturated monovalent hydrocarbon radical of three to six carbon atoms, e.g., cyclopropyl, cyclobutyl, cyclopentyl, or cyclohexyl.

"Di(1-3C alkoxy)(1-6C)alkyl" means a (1-6C)alkyl group as defined herein, wherein two carbons are each substituted with one (1-3C)alkoxy group as defined herein.

"Dihydroxy(2-6C)alkyl" means a linear saturated hydrocarbon radical of two to six carbon atoms or a branched saturated monovalent hydrocarbon radical of three to six carbons substituted with two hydroxy (OH) groups, provided that two hydroxy groups are not both on the same carbon atom.

"Halogen" as used herein means F, Cl, Br or I.

"Heteroaryl" refers to a 5-6 membered unsaturated ring system having one or more ring heteroatoms as recited for the specific heteroaryl group, wherein the heteroaryl is optionally substituted with substituents as defined for that particular heteroaryl group.

"Hydroxy(1-6C)alkyl" and "hydroxy(1-4C)alkyl" means a linear saturated hydrocarbon radical of one to six carbon atoms or one to four carbon atoms, respectively, or a branched saturated monovalent hydrocarbon radical of three to six carbon atoms or three to four carbon atoms, respectively, wherein one of the carbon atoms is substituted with a hydroxy (OH) group.

"Hydroxy(1-3C alkoxy)(1-6C)alkyl" means a (1-3C alkoxy)(1-6C)alkyl group as defined herein, wherein one of the carbons is substituted with a hydroxy group.

"(Trifluoromethoxy)(1-6C)alkyl" means a linear saturated hydrocarbon radical of one to six carbon atoms or a branched saturated monovalent hydrocarbon radical of three to six carbons substituted with one $CF_3O$— group.

It should be noted that compounds of the invention may contain groups that may exist in tautomeric forms, such as heteroatom substituted heteroaryl or heterocyclic groups and the like, which are illustrated in the following general and specific examples:

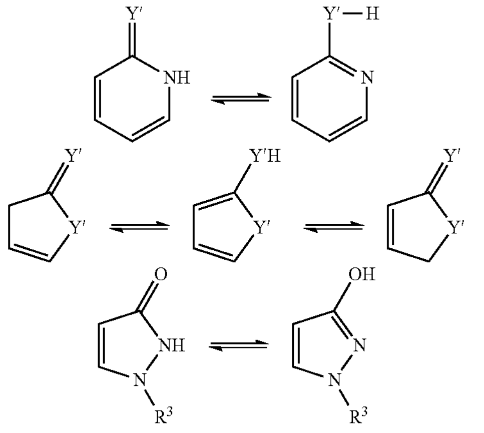

where Y'═O, S, or NR, and though one form is named, described, displayed and/or claimed herein, all the tautomeric forms are intended to be inherently included in such name, description, display and/or claim.

In one embodiment of Formula I, $R^a$, $R^b$, $R^c$ and $R^d$ are independently selected from H and methyl. In one embodiment, $R^a$, $R^b$, $R^c$ and $R^d$ are hydrogen. In one embodiment, $R^a$ is methyl and $R^b$, $R^c$ and $R^d$ are hydrogen. In one embodiment, $R^a$ and $R^b$ are methyl and $R^c$ and $R^d$ are hydrogen. In one embodiment, $R^a$, $R^b$ and $R^c$ are hydrogen and $R^d$ is methyl. In one embodiment, $R^a$ and $R^b$ are hydrogen and $R^c$ and $R^d$ are methyl.

In one embodiment, $R^c$ and $R^d$ are independently selected from H and (1-3C)alkyl, and $R^a$ and $R^b$ together with the atom to which they are attached form a cyclopropyl ring. In one embodiment, $R^c$ and $R^d$ are H, and $R^a$ and $R^b$ together with the atom to which they are attached form a cyclopropyl ring.

In one embodiment, X is O.

In one embodiment, X is S.

In one embodiment, X is NH.

In one embodiment, X is N—CN.

In one embodiment, $R^1$ is (1-3C alkoxy)(1-6C)alkyl, for example, methoxyethyl, methoxypropyl, ethoxyethyl and 2-methoxypropyl. In one embodiment, $R^1$ is 2-methoxyethyl or 2-methoxypropyl having the structures:

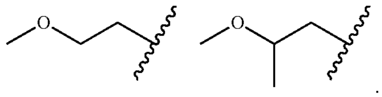

.

In one embodiment, $R^1$ is 2-methoxyethyl.

In one embodiment, $R^1$ is (trifluoromethoxy)(1-6C)alkyl, for example, trifluoromethoxyethyl, trifluoromethoxypropyl, and the like. In one embodiment, $R^1$ is trifluoromethoxyethyl.

In one embodiment, $R^1$ is (1-3C sulfanyl)(1-6C)alkyl, for example methylsulfanylethyl, ethylsulfanylethyl, and the like. In one embodiment, $R^1$ ismethylsulfanylethyl.

In one embodiment, $R^1$ is monofluoro(1-6C)alkyl, difluoro(1-6C)alkyl or trifluoro(1-6C)alkyl. In one embodiment, $R^1$ is 1,3-difluoroprop-2-yl, 2,2-difluoroethyl, 4,4,4-trifluorobutyl or 2,2,2-trifluoroethyl having the structures:

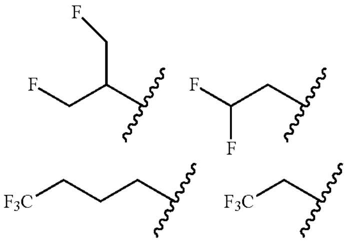

.

In one embodiment, $R^1$ is tetrafluoro(2-6C)alkyl or pentafluoro(2-6C)alkyl. In one embodiment, $R^1$ is 3,3,4,4,4-pentafluorobutyl.

In one embodiment, $R^1$ is cyano(1-6C)alkyl. In one embodiment, $R^1$ is 2-cyanoethyl.

In one embodiment, $R^1$ is aminocarbonyl(1-6C)alkyl. In one embodiment, $R^1$ is aminocarbonylmethyl or methylaminocarbonylmethyl.

In one embodiment, $R^1$ is hydroxy(1-6C)alkyl. In one embodiment, $R^1$ is 2-hydroxyethyl or 2-hydroxypropyl.

In one embodiment, $R^1$ is dihydroxy(2-6C)alkyl. In one embodiment, $R^1$ is the structure:

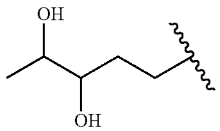

.

In one embodiment, $R^1$ is (1-6C)alkyl. In one embodiment, $R^1$ is methyl, ethyl, or propyl.

In one embodiment, $R^1$ is (1-3Calkylamino)(1-3C)alkyl, that is, a (1-3C)alkyl group which is substituted with a (1-3C alkyl)amino group, for example a (1-3Calkyl)NH— group such as methylamino. In one embodiment, $R^1$ is (2-methylamino)ethyl.

In one embodiment, $R^1$ is (1-4C alkoxycarbonyl)(1-6C) alkyl. In one embodiment, $R^1$ is methoxycarbonylmethyl, having the structure:

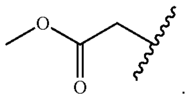

.

In one embodiment, $R^1$ is amino(1-6C)alkyl, such as methylamino(1-6C)alkyl. In one embodiment, $R^1$ is 2-methylaminoethyl.

In one embodiment, $R^1$ is hydroxy(1-3C alkoxy)(1-6C) alkyl. In one embodiment, $R^1$ is hydroxymethoxy(1-6C) alkyl. In one embodiment, $R^1$ is selected from the structures:

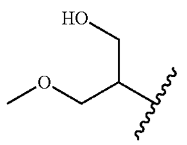

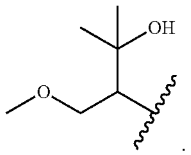

In one embodiment, $R^1$ is di(1-3C alkoxy)(1-6C)alkyl. In one embodiment, $R^1$ is dimethoxy(1-6C)alkyl. In one embodiment, $R^1$ is 1,3-dimethoxyprop-2-yl having the structure:

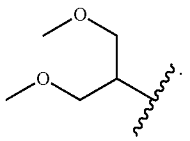

In one embodiment, $R^1$ is (1-3C alkoxy)trifluoro(1-6C)alkyl. Examples include methoxytrifluoro(1-6C)alkyl. In one embodiment, $R^1$ is 3,3,3-trifluoro-2-methoxypropyl.

In one embodiment, $R^1$ is hydroxytrifluoro(1-6C)alkyl. In one embodiment, $R^1$ is 3,3,3-trifluoro-2-hydroxypropyl.

In one embodiment, $R^1$ is (1-4C alkoxycarbonyl)(1-3C alkoxy)(1-6C)alkyl. In one embodiment, $R^1$ is (methoxycarbonyl)methoxy(1-6C)alkyl. In one embodiment, $R^1$ is the structure:

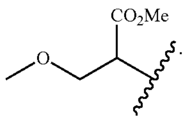

In one embodiment, $R^1$ is hydroxycarbonyl(1-3C alkoxy)(1-6C)alkyl. In one embodiment, $R^1$ is (methoxycarbonyl)hydroxy(1-6C)alkyl. In one embodiment, $R^1$ is the structure:

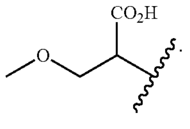

In one embodiment, $R^1$ is selected from (1-3C alkoxy)(1-6C)alkyl, difluoro(1-6C)alkyl and trifluoro(1-6C)alkyl.

In one embodiment, $R^2$ is H.

In one embodiment, $R^2$ is F.

In one embodiment, $R^2$ is OH.

In one embodiment of Formula I, Ring B is $Ar^1$, where $Ar^1$ is phenyl optionally substituted with one or more substituents independently selected from halogen, $CF_3$, $CF_3O$—, (1-4C)alkoxy, hydroxy(1-4C)alkyl, (1-6C)alkyl, and CN. In one embodiment, $Ar^1$ is phenyl optionally substituted with one or more substituents independently selected from halogen, $CF_3$, (1-4C)alkoxy and CN. In one embodiment, $Ar^1$ is phenyl optionally substituted with one or more substituents independently selected from F, Cl, $CF_3$, MeO and CN.

In one embodiment of Formula I, Ring B when represented by $Ar^1$ is phenyl, 2-fluorophenyl, 3-fluorophenyl, 4-fluorophenyl, 3,4-difluorophenyl, 3,5-difluorophenyl, 2,4-difluorophenyl, 2,5-difluorophenyl, 3,4,5-trifluorophenyl, 2-chlorophenyl, 3-chlorophenyl, 4-chlorophenyl, 3-trifluoromethylphenyl 3-methoxyphenyl, 3-chloro-4-fluorophenyl, 4-chloro-3-fluorophenyl, 3-chloro-5-fluorophenyl, 3-cyano-5-fluorophenyl, 2-cyanophenyl, 4-cyanophenyl or 3-cyano-4-fluorophenyl.

In one embodiment, Ring B is $Ar^1$, wherein $Ar^1$ is phenyl optionally substituted with one or more halogens. In one embodiment, $Ar^1$ is phenyl optionally substituted with one or more F or Cl. In one embodiment, $Ar^1$ is phenyl, 3-fluorophenyl, 4-fluorophenyl, 3,4-difluorophenyl, 3,5-difluorophenyl, 3,4,5-trifluorophenyl, 3-chloro-4-fluorophenyl, 3-chloro-5-fluorophenyl, or 4-chloro-3-fluorophenyl.

In one embodiment of Formula I, Ring B is $hetAr^1$, where $hetAr^1$ is a 5-6 membered heteroaryl having 1-3 ring heteroatoms independently selected from N, S and O, and is optionally substituted with one or more groups independently selected from (1-6C)alkyl, halogen, OH, $CF_3$, $NH_2$ and hydroxy(1-2C)alkyl. In one embodiment, Ring B is $hetAr^1$, wherein $hetAr^1$ is a 5-6 membered heteroaryl having 1-2 ring heteroatoms independently selected from N, S and O, and optionally substituted with 1-2 groups independently selected from (1-6C)alkyl, halogen, OH, $CF_3$, $NH_2$ and hydroxy(1-2C)alkyl. Examples of Ring B include pyridyl, thiophenyl, thiazolyl, oxazolyl, and isoxazolyl rings optionally substituted with 1-2 groups independently selected from (1-6C)alkyl, halogen, OH, $CF_3$, $NH_2$ and hydroxy(1-2C) alkyl. In one embodiment, Ring B is a pyridyl, thiophenyl, thiazolyl, oxazolyl, or isoxazolyl ring optionally substituted with 1-2 groups independently selected from halogen and (1-6C)alkyl.

In one embodiment, Ring B when represented by $hetAr^1$ is pyrid-4-yl, pyrid-3-yl, pyrid-2-yl, 5-fluoropyrid-3-yl, thien-2-yl, thiazol-2-yl, 2,4-dimethylthiazol-5-yl, oxazol-5-yl, isoxazol-5-yl, 5-chloropyrid-3-yl, 5-fluoropyrid-2-yl, 3-fluoropyrid-4-yl or 1-methylpyrazol-4-yl having the structures:

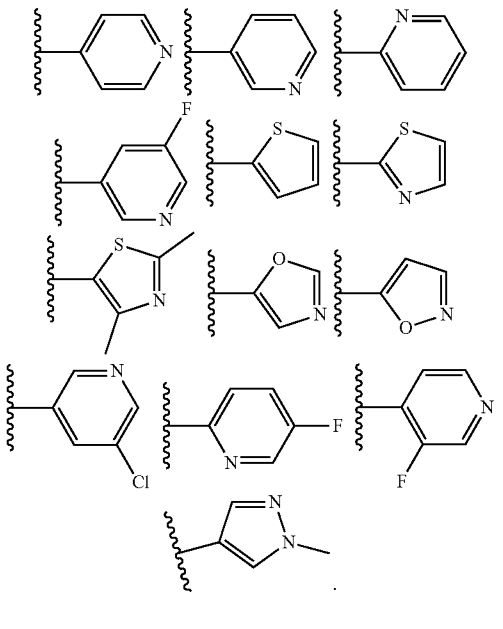

In one embodiment of Formula I, Ring B is a pyridyl ring optionally substituted with 1-2 groups independently selected from (1-6C)alkyl and halogen.

In one embodiment of Formula I, $R^6$ is H.

In one embodiment of Formula I, $R^6$ is halogen. In one embodiment, $R^6$ is F, Cl or Br.

In one embodiment of Formula I, $R^6$ is phenyl optionally substituted with one or more substituents independently selected from halogen and (1-3C)alkyl. In one embodiment, $R^6$ is phenyl.

In one embodiment of Formula I, $R^{7a}$ is H and $R^{7b}$ is H, (1-6C)alkyl, or phenyl [optionally substituted with one or more substituents independently selected from halogen and (1-3C)alkyl].

In one embodiment of Formula I, $R^{7a}$ is H and $R^{7b}$ is H or (1-6C)alkyl.

In one embodiment of Formula I, $R^8$ is phenyl optionally substituted with one to three substituents independently selected from halogen, (1-3C)alkyl and (3-6C)cycloalkyl. In one embodiment, $R^8$ is phenyl optionally substituted with one to three substituents independently selected from halogen, (1-3C)alkyl, cyclopropyl and cyclobutyl. In one embodiment, $R^8$ is phenyl.

In one embodiment of Formula I, $R^{8a}$ is H

In one embodiment of Formula I, $R^{8a}$ is phenyl optionally substituted with one or more substituents independently selected from halogen, (1-3C)alkyl and (3-6C)cycloalkyl. In one embodiment, $R^{8a}$ is phenyl.

In one embodiment of Formula I, $R^9$ is H.

In one embodiment of Formula I, In one embodiment, $R^9$ is F, Cl or Br.

In one embodiment of Formula I, $R^9$ is (1-6C)alkyl optionally substituted with one to five fluoros. In one embodiment, $R^9$ is methyl, ethyl, isopropyl or trifluoromethyl.

In one embodiment of Formula I, $R^9$ is (1-6C)alkoxy. In one embodiment, $R^9$ is methoxy or ethoxy.

In one embodiment of Formula I, $R^{10}$ is H.

In one embodiment of Formula I, $R^{10}$ is (1-6C)alkyl. In one embodiment, $R^{10}$ is methyl, ethyl or isopropyl.

In one embodiment of Formula I, Ring C is formula C-1

C-1

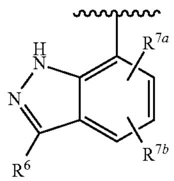

where $R^6$, $R^{7a}$ and $R^{7b}$ are as defined for Formula I.

In one embodiment of formula C-1, $R^6$ is H.

In one embodiment of formula C-1, $R^6$ is halogen. In one embodiment, $R^6$ is F, Cl or Br.

In one embodiment of formula C-1, $R^6$ is phenyl optionally substituted with one or more substituents independently selected from halogen and (1-3C)alkyl. In one embodiment, $R^6$ is phenyl.

In one embodiment of formula C-1, $R^{7a}$ is H and $R^{7b}$ is H, (1-6C)alkyl, or phenyl [optionally substituted with one or more substituents independently selected from halogen and (1-3C)alkyl].

In one embodiment of formula C-1, $R^{7a}$ is H and $R^{7b}$ is H or (1-6C)alkyl.

In one embodiment, formula C-1 is selected from the structures:

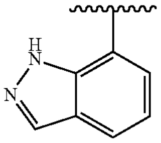
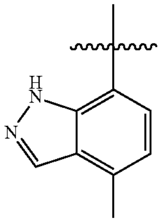
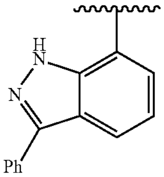

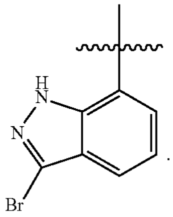
.

In one embodiment of Formula I, ring C is C-2:

C-2

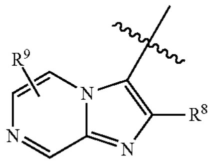

where $R^8$ and $R^9$ are as defined for Formula I.

In one embodiment of formula C-2, $R^8$ is phenyl optionally substituted with one to three substituents independently selected from halogen, (1-3C)alkyl and (3-6C)cycloalkyl.

In one embodiment of formula C-2, $R^8$ is phenyl optionally substituted with one to three substituents independently selected from halogen, (1-3C)alkyl, cyclopropyl and cyclobutyl. In one embodiment, $R^8$ is phenyl.

In one embodiment of formula C-2, $R^9$ is H.

In one embodiment of formula C-2, $R^9$ is halogen. In one embodiment, $R^9$ is F, Cl or Br.

In one embodiment of formula C-2, $R^9$ is (1-6C)alkyl optionally substituted with one to five fluoros. In one embodiment, $R^9$ is methyl, ethyl, isopropyl or trifluoromethyl.

In one embodiment of formula C-2, $R^9$ is (1-6C)alkoxy. In one embodiment, $R^9$ is methoxy or ethoxy.

In one embodiment, formula C-2 is selected from the structures:

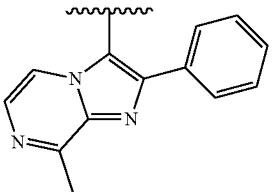
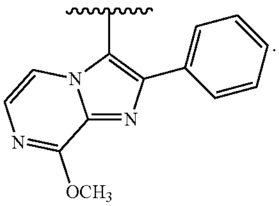
.

In one embodiment of Formula I, Ring C is formula C-3

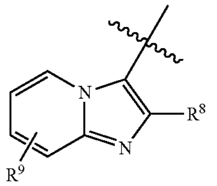

where $R^8$ and $R^9$ are as defined for Formula I.

In one embodiment of formula C-3, $R^8$ is phenyl optionally substituted with one to three substituents independently selected from halogen, (1-3C)alkyl and (3-6C)cycloalkyl.

In one embodiment of formula C-3, $R^8$ is phenyl optionally substituted with one to three substituents independently selected from halogen, (1-3C)alkyl, cyclopropyl and cyclobutyl. In one embodiment, $R^8$ is phenyl.

In one embodiment of formula C-3, $R^9$ is H.

In one embodiment of formula C-3, $R^9$ is halogen. In one embodiment of formula C-3, $R^9$ is F, Cl or Br.

In one embodiment of formula C-3, $R^9$ is (1-6C)alkyl optionally substituted with one to five fluoros. In one embodiment, $R^9$ is methyl, ethyl, isopropyl or trifluoromethyl.

In one embodiment of formula C-3, $R^9$ is (1-6C)alkoxy. In one embodiment, $R^9$ is methoxy or ethoxy.

In one embodiment, formula C-3 is selected from the structures:

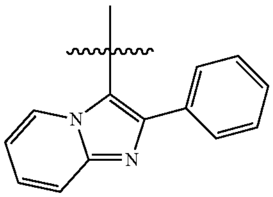

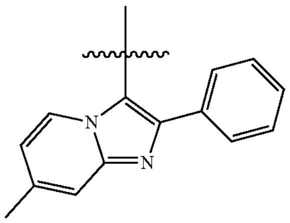

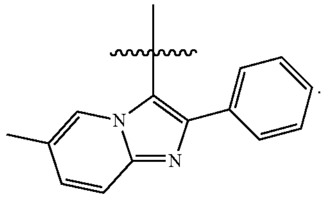

In one embodiment of Formula I, Ring C is formula C-4

C-4

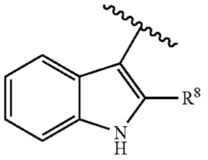

where $R^8$ is as defined for Formula I. In one embodiment, $R^8$ is phenyl optionally substituted with one to three substituents independently selected from halogen, (1-3C)alkyl, cyclopropyl and cyclobutyl. In one embodiment, $R^8$ is phenyl.

In one embodiment, formula C-4 is selected from the structures:

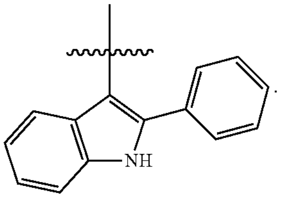 [SMILES: *c1c(-c2ccccc2)[nH]c2ccccc12]

In one embodiment of Formula I, Ring C is formula C-5

C-5

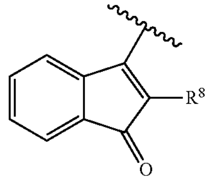

where $R^8$ is as defined for Formula I.

In one embodiment of formula C-5, $R^8$ is phenyl optionally substituted with one to three substituents independently selected from halogen, (1-3C)alkyl and (3-6C)cycloalkyl. In one embodiment, $R^{8a}$ is phenyl.

In one embodiment, formula C-5 has the structures:

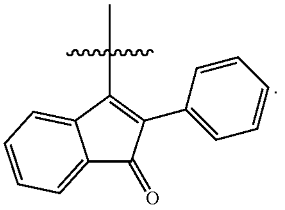 [SMILES: *C1=C(c2ccccc2)C(=O)c2ccccc21]

In one embodiment of Formula I, Ring C is formula C-6

C-6

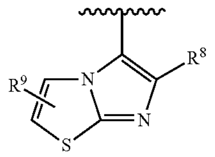

where $R^8$ and $R^9$ are as defined for Formula I.

In one embodiment of formula C-6, $R^8$ is phenyl optionally substituted with one to three substituents independently selected from halogen, (1-3C)alkyl and (3-6C)cycloalkyl. In one embodiment, $R^8$ is phenyl optionally substituted with one to three substituents independently selected from halogen, (1-3C)alkyl, cyclopropyl and cyclobutyl. In one embodiment, $R^8$ is phenyl.

In one embodiment of formula C-6, $R^9$ is H.

In one embodiment of formula C-6, $R^9$ is halogen. In one embodiment of formula C-6, $R^9$ is F, Cl or Br.

In one embodiment of formula C-6, $R^9$ is (1-6C)alkyl optionally substituted with one to five fluoros. In one embodiment, $R^9$ is methyl, ethyl, isopropyl or trifluoromethyl.

In one embodiment of formula C-6, $R^9$ is (1-6C)alkoxy. In one embodiment, $R^9$ is methoxy or ethoxy.

In one embodiment, formula C-6 is selected from the structures:

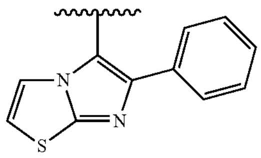

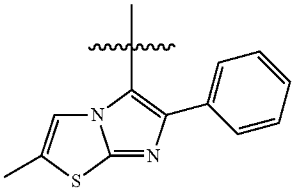

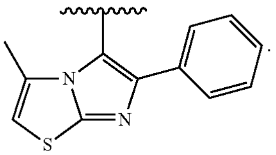

In one embodiment of Formula I, Ring C is formula C-7

C-7

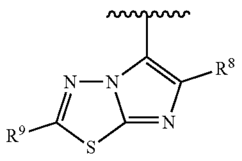

where $R^8$ and $R^9$ are as defined for Formula I.

In one embodiment of formula C-7, $R^8$ is phenyl optionally substituted with one to three substituents independently selected from halogen, (1-3C)alkyl and (3-6C)cycloalkyl. In one embodiment, $R^8$ is phenyl optionally substituted with one to three substituents independently selected from halogen, (1-3C)alkyl, cyclopropyl and cyclobutyl. In one embodiment, $R^8$ is phenyl.

In one embodiment of formula C-7, $R^9$ is H.

In one embodiment of formula C-7, $R^9$ is halogen. In one embodiment of formula C-7, $R^9$ is F, Cl or Br.

In one embodiment of formula C-7, $R^9$ is (1-6C)alkyl optionally substituted with one to five fluoros. In one embodiment, $R^9$ is methyl, ethyl, isopropyl or trifluoromethyl.

In one embodiment of formula C-7, $R^9$ is (1-6C)alkoxy. In one embodiment, $R^9$ is methoxy or ethoxy.

In one embodiment, formula C-7 is selected from the structures:

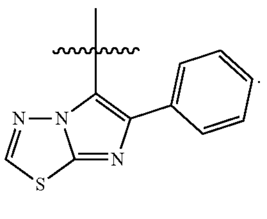 [SMILES: *c1c(-c2ccccc2)nc2scnn12]

In one embodiment of Formula I, Ring C is formula C-8

C-8

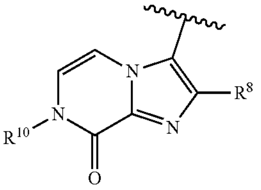

where $R^8$ and $R^{10}$ are as defined for Formula I.

In one embodiment of formula C-8, $R^8$ is phenyl optionally substituted with one to three substituents independently selected from halogen, (1-3C)alkyl and (3-6C)cycloalkyl.

In one embodiment of formula C-8, $R^8$ is phenyl optionally substituted with one to three substituents independently selected from halogen, (1-3C)alkyl, cyclopropyl and cyclobutyl.

In one embodiment of formula C-8, $R^{10}$ is H.

In one embodiment of formula C-8, $R^{10}$ is (1-6C)alkyl. In one embodiment, $R^{10}$ is methyl, ethyl or isopropyl.

In one embodiment, formula C-8 is selected from the structures:

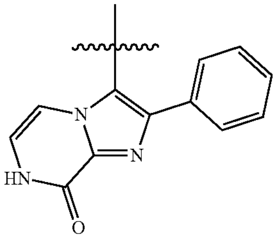

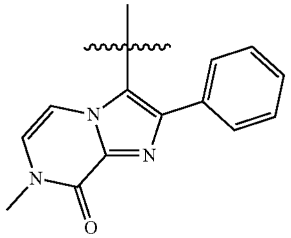

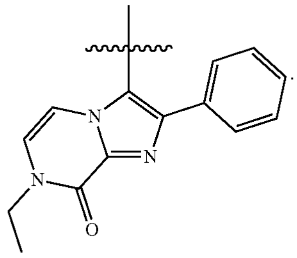

In one embodiment of Formula I, Ring C is formula C-9

C-9

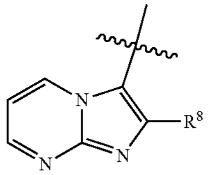

where $R^8$ is as defined for Formula I.

In one embodiment of formula C-9, $R^8$ is phenyl optionally substituted with one to three substituents independently selected from halogen, (1-3C)alkyl and (3-6C)cycloalkyl.

In one embodiment of formula C-9, $R^8$ is phenyl optionally substituted with one to three substituents independently selected from halogen, (1-3C)alkyl, cyclopropyl and cyclobutyl.

In one embodiment, formula C-9 has the structure:

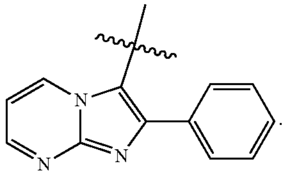 [SMILES: *c1c(-c2ccccc2)nc2ncccn12]

In one embodiment, Formula I comprises compounds of Formula I-a, wherein:

Ring B and the NH—C(=X)—NH moiety are in the trans configuration;

$R^a$, $R^b$, $R^c$ and $R^d$ are H;

X is O;

$R^1$ is (1-3C alkoxy)(1-6C)alkyl;

$R^2$ is H;

Ring B is $Ar^1$;

$Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN;

Ring C is selected from formulas C-1 to C-9; and $R^6$, $R^7$, $R^8$, $R^{8a}$, $R^9$ and $R^{10}$ are as defined for Formula I.

As noted, Ring B and the —NH—C(=X)—NH— moiety of Formulas I, IA and IB are in the trans configuration on the pyrrolidine ring, which relative stereochemistry can be illustrated by either generic structure A or B:

A

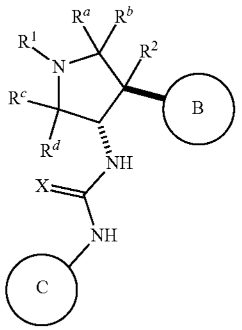

B

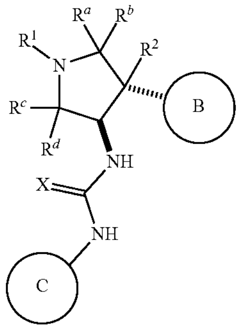

in which the straight thick bars (▬) and straight dashed bars (⦙⦙⦙⦙) indicate relative stereochemistry.

In one embodiment of Formulas I, IA and IB, Ring B and the —NH—C(=X)—NH— moiety trans in the absolute configuration which can be illustrated by generic structure C and D:

C

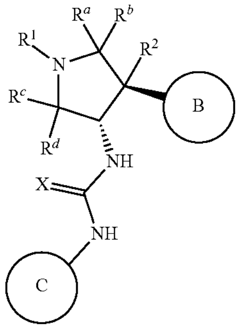

D

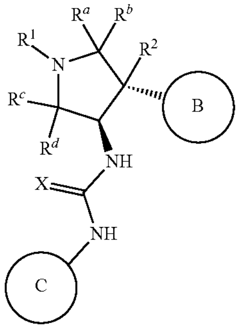

in which the solid wedges (◀) and dashed wedges (⦙⦙⦙⦙) indicate absolute stereochemistry.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention. For example, compounds of Formula I can exist in unsolvated as well as solvated forms with pharmaceutically acceptable solvents such as water, ethanol, and the like.

The compounds of Formula I include pharmaceutically acceptable salts thereof. In addition, the compounds of Formula I also include other salts of such compounds which are not necessarily pharmaceutically acceptable salts, and which are useful as intermediates for preparing and/or purifying compounds of Formula I and/or for separating enantiomers of compounds of Formula I. Particular examples of salts include hydrochloride salts and trifluoroacetate salts.

In one embodiment, the compounds of Formula I include the free base form of compounds of Examples 1-28, or a pharmaceutically acceptable salt thereof.

In one embodiment, the compounds of Formula I include the hydrochloride salts of compounds of Examples 1-28.

In one embodiment, the compounds of Formula I include the trifluoroacetate salts of compounds of Examples 1-28.

The term "pharmaceutically acceptable" indicates that the substance or composition is compatible chemically and/or toxicologically, with the other ingredients comprising a formulation, and/or the mammal being treated therewith.

The present invention also provides a process for the preparation of a compound of Formula I or a salt thereof as defined herein, which comprises:

(a) for a compound of Formula I where X is O, coupling a corresponding compound having the formula II

II

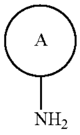

with a corresponding compound having the formula III

III

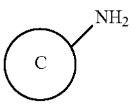

in the presence carbonyldiimidazole or triphosgene and a base; or (b) for a compound of Formula I where X is S, coupling a corresponding compound having the formula II

II

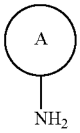

with a corresponding compound having the formula III

III

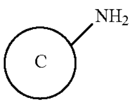

in the presence di(1H-imidazol-2-yl)methanethione and a base; or (c) for a compound of Formula I where X is O, coupling a corresponding compound having the formula II

II

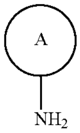

with a corresponding compound having the formula IV

IV

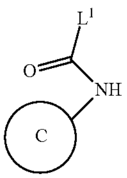

where $L^1$ is a leaving group, in the presence of a base; or (d) for a compound of Formula I where X is O, coupling a corresponding compound having the formula V

V

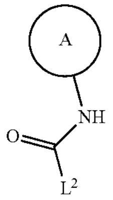

where $L^2$ is a leaving group, with a corresponding compound having the formula III

III

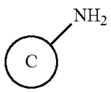

in the presence of a base; or (e) for a compound of Formula I where X is O, activating a corresponding compound having the formula VI

VI

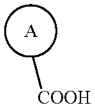

with diphenylphosphoryl azide followed by coupling the activated intermediate with a corresponding compound having the formula III

III

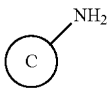

in the presence a base; or (f) for a compound of Formula I where X is O, coupling a corresponding compound having the formula II

II

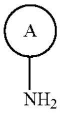

with a corresponding compound having the formula VII

VII

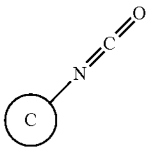

in the presence of a base; or (g) for a compound of Formula I where X is O, coupling a corresponding compound having the formula VIII

VIII

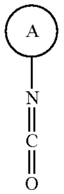

with a corresponding compound having the formula III

III

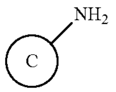

in the presence of a base; and optionally removing protecting groups and optionally preparing a pharmaceutically acceptable salt thereof, wherein in any of the above methods (a), (b), (c), (d), (e), (f), or (g), the ring A is

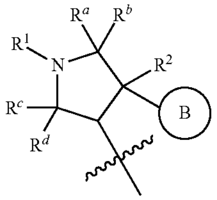

where $R^1$, $R^2$, Ring B, $R^a$, $R^b$, $R^c$ and $R^d$ are as defined for Formula I.

In the above methods, the term "corresponding" means that the definitions for the "corresponding compound" are as defined for Formula I unless stated otherwise.

Referring to method (a), the base may be an amine base, such as triethylamine or diisopropylethylamine. Suitable solvents include dichloromethane, dichloroethane, THF, DMA and DMF. The reaction is conveniently performed at ambient temperature.

Referring to method (b), the base may be an amine base, such as triethylamine or diisopropylethylamine. Suitable solvents include dichloromethane, dichloroethane, THF, DMA and DMF. The reaction is conveniently performed at ambient temperature.

Referring to method (c), the leaving group may be, for example, phenoxy or 4-nitrophenoxy. The base may be an amine base, such as triethylamine or diisopropylethylamine. Suitable solvents include DMA, DMF and DCE. The reaction is conveniently performed at ambient temperature.

Referring to method (d), the leaving group may be, for example, phenoxy or 4-nitrophenoxy. The base may be an amine base, such as triethylamine or diisopropylethylamine. Suitable solvents include DCE, DMA and DMF. The reaction is conveniently performed at ambient temperature.

Referring to method (e), the base may be an amine base, such as triethylamine or diisopropylethylamine. Suitable solvents include toluene and DMF. The reaction is conveniently performed at elevated temperatures, for example the reflux temperature of the solvent.

Referring to methods (f) and (g), the base may be an amine base, such as triethylamine or diisopropylethylamine. Suitable solvents include DCM, DCE, DMF and THF. The reaction is conveniently performed at temperatures between about 0° C. and ambient temperature.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC) and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include benzyl, trityl, silyl ethers, and the like.

The compounds of the formulas II, III, IV, V, VI and VII are also provided as further aspects of the invention. In one embodiment, the compounds of the formulas II, III, IV, V, VI and VII are useful as intermediates for the preparation of compounds of Formula I.

In the above methods, the term "corresponding" means that the definitions for the "corresponding compound" are as defined for Formula I unless stated otherwise.

Referring to method (a), the base may be an amine base, such as triethylamine or diisopropylethylamine. Suitable solvents include dichloromethane, dichloroethane, THF, DMA and DMF. The reaction is conveniently performed at ambient temperature.

Referring to method (b), the base may be an amine base, such as triethylamine or diisopropylethylamine. Suitable solvents include dichloromethane, dichloroethane, THF, DMA and DMF. The reaction is conveniently performed at ambient temperature.

Referring to method (c), the leaving group may be, for example, phenoxy or 4-nitrophenoxy. The base may be an amine base, such as triethylamine or diisopropylethylamine. Suitable solvents include DMA, DMF and DCE. The reaction is conveniently performed at ambient temperature.

Referring to method (d), the leaving group may be, for example, phenoxy or 4-nitrophenoxy. The base may be an amine base, such as triethylamine or diisopropylethylamine. Suitable solvents include DCE, DMA and DMF. The reaction is conveniently performed at ambient temperature.

Referring to method (e), the base may be an amine base, such as triethylamine or diisopropylethylamine. Suitable solvents include toluene and DMF. The reaction is conveniently performed at elevated temperatures, for example the reflux temperature of the solvent.

Referring to method (f), the base may be an amine base, such as triethylamine or diisopropylethylamine. Suitable solvents include DCM, DCE, DMF and THF. The reaction is conveniently performed at temperatures between about 0° C. and ambient temperature.

A compound of Formula VII may be prepared by reacting a compound of Formula III with bis(trichloromethyl) carbonate in the presence of a base, such as an amine base.

Referring to method (g), the base may be an amine base, such as triethylamine or diisopropylethylamine. Suitable solvents include DMF, DMA and THF. The reaction is conveniently performed at temperatures between ambient temperature and 60° C.

The compounds of the formulas II, III, III, IV, V, VI, VII, and VIII are provided as further aspects of the invention. In one embodiment, formulas II, III, III, IV, V, VI, VII, and VIII are useful as intermediates for the preparation of compounds of Formula I.

In one embodiment of the above-described processes (a), (b), (c), and (f), where ring B is $Ar^1$ and $R^a$, $R^b$, $R^c$, $R^d$ and $R^2$ are hydrogen, a single enantiomer of intermediate II, namely enantiomer 1 of II-A is prepared by chiral crystallization prior to use. Accordingly, in one embodiment, a process for preparing enantiomer 1 of II-A comprises:

preparing racemic trans II-A

II-A

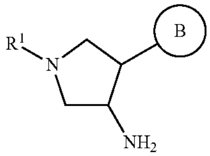

where Ring B and the $NH_2$ group are in the trans configuration; Ring B is $Ar^1$ or $hetAr^1$; $Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN; and $hetAr^1$ is a 5-6 membered heteroaryl having 1-3 ring heteroatoms independently selected from N, S and O, and optionally substituted with 1-2 groups independently selected from (1-6C) alkyl, halogen, OH, $CF_3$, $NH_2$ and hydroxy(1-2C)alkyl; said method comprising:

treating racemic trans II-A with di-p-toluoyl-D-tartaric acid to provide the di-p-toluoyl-D-tartaric acid salt of racemic trans II-A;

recrystallizing the di-p-toluoyl-D-tartaric acid salt of trans II-A to provide the di-p-toluoyl-D-tartaric acid salt of enantiomer 1 of trans II-A; and treating the di-p-toluoyl-D-tartaric acid salt of enantiomer 1 of trans II-A with an inorganic base to provide free base of enantiomer 1 of trans II-A having the absolute configuration as illustrated:

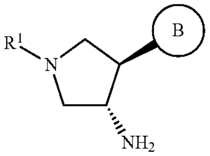

enantiomer 1 of II-A

In one embodiment of enantiomer 1 of trans II-A, $R^1$ is 2-methoxyethoxy and Ring B is 4-fluorophenyl, and racemic trans II-A is prepared by the process comprising:

reacting 4-fluorobenzaldehyde with nitromethane in the presence of acetic acid and ammonium acetate to provide (E)-1-fluoro-4-(2-nitrovinyl)benzene

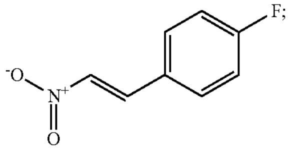

reacting (E)-1-fluoro-4-(2-nitrovinyl)benzene with 2-methoxy-N-(methoxymethyl)-N-((trimethylsilyl)methyl) ethanamine in the presence of a catalytic amount of an acid (such as TFA) to provide trans-3-(4-fluorophenyl)-1-(2-methoxyethyl)-4-nitropyrrolidine

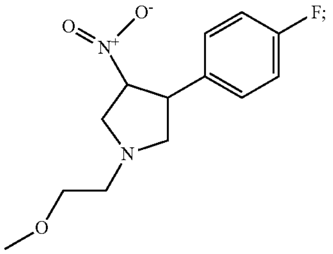 [SMILES: COCCN1CC(c2ccc(F)cc2)C([N+](=O)[O-])C1]

and treating trans-3-(4-fluorophenyl)-1-(2-methoxyethyl)-4-nitropyrrolidine with platinum (IV) oxide or Raney Nickel in a hydrogen atmosphere to provide trans-4-(4-fluorophenyl)-1-(2-methoxyethyl)pyrrolidin-3-amine

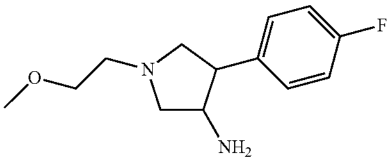 [SMILES: COCCN1CC(N)C(c2ccc(F)cc2)C1]

wherein the 4-fluorophenyl and amino group are in the trans configuration.

In one embodiment of enantiomer 1 of trans II-A, $R^1$ is 2-methoxyethoxy and Ring B is 3,4-difluorophenyl.

In one embodiment of the method for preparing racemic trans II-A, the inorganic base is an alkali metal hydroxide such as sodium hydroxide.

A similar process as above may be used utilizing di-p-toluoyl-L-tartaric acid to provide enantiomer 2 of II-A:

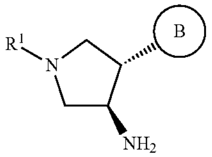

enantiomer 2 of II-A where $R^1$ and Ring B are as defined for Formula I. In one embodiment of enantiomer 2 of trans II-A, $R^1$ is 2-methoxyethoxy and Ring B is 4-fluorophenyl. In one embodiment of enantiomer 2 of trans II-A, $R^1$ is 2-methoxyethoxy and Ring B is 3,4-difluorophenyl.

In one embodiment, the inorganic base is an alkali metal hydroxide such as sodium hydroxide.

A similar process as above may be used utilizing di-p-toluoyl-L-tartaric acid to provide enantiomer 2 of II-A:

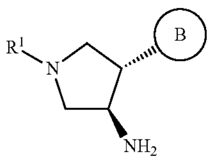

enantiomer 2 of II-A

The ability of compounds of the invention to act as TrkA inhibitors may be demonstrated by the assay described in Example A.

Compounds of Formula I are useful in the treatment of pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

In one embodiment, compounds of Formula I are useful for treating pain, including chronic and acute pain. For example, compounds of Formula I are useful in the treatment of multiple types of pain including inflammatory pain, neuropathic pain, and pain associated with cancer, surgery or bone fracture.

In one embodiment, compounds of Formula I are useful for treating acute pain. Acute pain, as defined by the International Association for the Study of Pain, results from disease, inflammation, or injury to tissues. This type of pain generally comes on suddenly, for example, after trauma or surgery, and may be accompanied by anxiety or stress, and is confined to a given period of time and severity. In some instances, it can become chronic.

In one embodiment, compounds of Formula I are useful for treating chronic pain. Chronic pain, as defined by the International Association for the Study of Pain, is widely believed to represent a disease in itself. It can be made much worse by environmental and psychological factors. Chronic pain persists over a longer period than acute pain and is resistant to most medical treatments, generally over 3 months or more. It can and often does cause severe problems for patients.

Compounds of Formula I are also useful for treating cancer. Particular examples include neuroblastoma, ovarian, pancreatic, colorectal and prostate cancer.

Compounds of Formula I are also useful for treating inflammation and certain infectious diseases. For example, compounds of Formula I may be used to treat interstitial cystitis (IC), painful bladder syndrome (PBS), urinary incontinence, asthma, atopic dermatitis, and psoriasis.

Compounds of Formula I are also useful for treating a neurodegenerative disease in a mammal, comprising administering to said mammal one or more compounds of Formula I or a pharmaceutically acceptable salt thereof in an amount effective to treat said neurodegenerative disease. In one embodiment, compounds of Formula I may also be used to treat demyelination and dysmyelination by promoting myelination, neuronal survival, and oligodendrocyte differentiation via blocking Sp35-TrkA interaction. In one embodiment, the neurodegenerative disease is multiple sclerosis. In one embodiment, the neurodegenerative disease is Parkinson's disease. In one embodiment, the neurodegenerative disease is Alzheimer's disease.

Compounds of Formula I are also useful for treating certain infectious diseases such as *Trypanosoma cruzi* infection in a mammal.

Compounds of Formula I are also useful for treating Sjogren's syndrome in a mammal.

Compounds of Formula I are also useful for treating endometriosis in a mammal.

Compounds of Formula I are also useful for treating diabetic peripheral neuropathy in a mammal.

Compounds of Formula I are also useful for treating prostatitis in a mammal.

Compounds of Formula I are also useful for treating pelvic pain syndrome in a mammal.

Compounds of Formula I are also useful in treating diseases related to an imbalance of the regulation of bone remodeling, such as osteoporosis, rheumatoid arthritis, and bone metastases.

As used herein, terms "treat" or "treatment" refer to therapeutic or palliative measures. Beneficial or desired clinical results include, but are not limited to, alleviation, in whole or in part, of symptoms associated with a disorder or condition, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

In certain embodiments, compounds of Formula I are useful for preventing diseases and disorders as defined herein. The term "preventing" as used herein means the prevention of the onset, recurrence or spread, in whole or in part, of the disease or condition as described herein, or a symptom thereof, and includes to the administration of a compound of Formula I prior to the onset of symptoms.

Accordingly, one embodiment of this invention provides a method of treating pain in a mammal, comprising administering to said mammal in need thereof one or more compounds of Formula I or a pharmaceutically acceptable salt thereof in an amount effective to treat said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of preventing pain in a mammal, comprising administering to said mammal in need thereof one or more compounds of Formula I or a pharmaceutically acceptable salt thereof in an amount effective to prevent said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of treating cancer in a mammal, comprising administering to said mammal in need thereof one or more compounds of Formula I or a pharmaceutically acceptable salt thereof in an amount effective to treat said cancer.

In one embodiment, provided herein is a method for treating a patient diagnosed with a cancer having a dysregulation of TrkA, comprising administering to the patient a therapeutically effective amount of a compound of the invention or a pharmaceutically acceptable salt thereof.

In one embodiment, the dysregulation of TrkA comprises overexpression of wild-type TrkA (autocrine activation).

In one embodiment, the dysregulation of TrkA comprises one or more chromosome translocations or inversions resulting in TrkA gene fusions. In one embodiment, the dysregulation is a result of genetic translocations in which the expressed protein is a fusion protein containing residues from non-TrkA and TrkA proteins, and at a minimum the TrkA kinase domain. In one embodiment, the TrkA fusion protein is LMNA-TrkA, TFG-TrkA, TPM3-TrkA, CD74-TrkA, NFASC-TrkA, MPRIP-TrkA, BCAN-TrkA, or TPR-TrkA, where:

LMNA=Prelamin-A/C;

TFG=TRK-fused gene protein;

TPM3=Tropomysin alpha-3;

CD74=HLA class II histocompatibility antigen gamma chain;

NFASC=Neurofascin;

MPRIP=MPRIP protein;

BCAN=Brevican core protein; and

TPR=Nucleoprotein TPR

In one embodiment, the dysregulation of TrkA comprises one or more deletions, insertions or mutations in the TrkA protein. In one embodiment, the dysregulation comprises a deletion of one or more residues from the TrkA protein, resulting in constitutive activity of TrkA kinase. In one embodiment the deletion includes deletion of residues 303-377 in TrkA Isoform 2.

In one embodiment, the dysregulation of TrkA comprises a splice variation in which the expressed protein is an alternatively spliced variant of TrkA having one or more residues deleted resulting in constitutive activity of TrkA kinase. In one embodiment, an alternatively spliced form of TrkA with constitutive activity has deletions of exons 8, 9, and 11 resulting in an expressed protein missing residues 192-284 and 393-398 relative to TrkA Isoform 2.

Cancers identified as having dysregulation of TrkA (see literature references below; also see www.cancer.gov and www.nccn.org) include:

(A) Cancers wherein the dysregulation of TrkA comprises one or more chromosome translocations or inversions resulting in TrkA gene fusions, including:

| Cancer | Literature reference(s) | Standard of Care |
|---|---|---|
| Non-Small Cell Lung Cancer | Vaishnavi et al. 2013: Nature Medicine 19, 1469-1472 | radiotherapy (e.g. radioiodide therapy, external-beam radiation, radium 223 therapy), chemotherapeutics as single agents (e.g. afatinib dimaleate, bevacizumab, carboplatin, cetuximab, cisplatin, crizotinib, erlotinib, gefitinib, gemcitabine, methotrexate, paclitaxel, pemetrexed) or combinations (e.g. carboplatin-paclitaxel, gemcitabine-paclitaxel, chemoradiation) |
| Papillary Thyroid Carcinoma | Caria et al. 2010: Cancer Genetics and Cytogenetics 203: 21-29 | Radiotherapies (e.g. radioiodide therapy, external-beam radiation) and chemotherapeutics (e.g. sorafenib, sunitinib, pazopanib) |
| Glioblastoma Multiforme | Frattini et al. 2013: Nature Genet. 45(10): 1141-9 | Chemotherapeutics (e.g. bevacizumab, everolimus, lomustine, temozolomide) |
| Colorectal Carcinoma | Martin-Zanca et al. 1986: Nature 319: 743 | Chemotherapeutics as single agents (aflibercept, bevacizumab, capecitabine, cetuximab, fluorouracil, irinotecan, leucovorin, oxaliplatin, panitumumab, regorafenib) or combinations (e.g. folfox, folfiri, capox, folfiri-bevacizumab, folfiri-cetuximab, xelox) |

-continued

| Cancer | Literature reference(s) | Standard of Care |
|---|---|---|
| Melanoma | WO 2013/059740 A1 | Chemotherapeutics (e.g. aldesleukin, dabrafenib, dacarbazine, interferon alfa-2b, ipilimumab, peginterferon alfa-2b, trametinib, vemurafenib) |

(B) Cancers wherein the dysregulation of TrkA comprises one or more deletions, insertions or mutations in the TrkA protein, including:

| Cancer | Literature reference(s) | Standard of care |
|---|---|---|
| Acute Myeloid leukemia | Meyer 2007: Leukemia 21: 2171-2180 Reuther et al. 2000: Mol Cell Biol 20: 8655-8666 | Chemotherapeutics as single agents (e.g. arsenic trioxide, cyclophosphamide, cytarabine, daunorubicin, doxorubicin, vincristine) or combinations (e.g. ADE) |
| Large Cell Neuroendocrine Carcinoma | Marchetti et al 2008: Human Mutation 29(5): 609-616 | Radiotherapy (e.g. radioiodide therapy, external-beam radiation, radium 223 therapy) and/or chemotherapeutics (e.g. cisplatin, carboplatin, etoposide) |
| Neuroblastoma | Tacconelli et al 2004: Cancer Cell 6: 347 | Chemotherapeutics (e.g. cyclophosphamide, doxorubicin, vincristine) |

(C) Cancers driven by overexpression of wild-type TrkA (autocrine activation), including:

| Cancer | Literature Reference(s) | Standard of care |
|---|---|---|
| Prostate Carcinoma | Walch et al: Clinical & Experimental Metastasis 17: 307-314 Papatsoris et al 2007: Expert Opinion on Investigational Drugs 16(3): 303-309 | Radiotherapy (e.g. radium 223 therapy) or chemotherapeutics (e.g. abiraterone, cabazitaxel, degarelix, denosumab, docetaxel, enzalutamide, leuprolide, prednisone, sipuleucel-T) |
| Neuroblastoma | Van Noesel et al 2004: Gene 325: 1-15 | Chemotherapeutics (e.g. cyclophosphamide, doxorubicin, vincristine) |
| Pancreatic Carcinoma | Zhang et al 2005: Oncology Reports 14: 161-171 | Chemotherapeutics as single agents (e.g. erlotinib, fluorouracil, gemcitabine, mitomycin C) or combinations (e.g. gemcitabine-oxaliplatin) |
| Melanoma | Truzzi et al 2008: Journal of Investigative Dermatology 128(8): 2031 | Chemotherapeutics (e.g. aldesleukin, dabrafenib, dacarbazine, interferon alfa-2b, ipilimumab, peginterferon alfa-2b, trametinib, vemurafenib) |
| Head and Neck Squamous Cell Carcinoma | Kolokythas et al 2010: Journal of Oral and Maxillofacial Surgery 68(6): 1290-1295 | Radiotherapy and/or chemotherapeutics (e.g. bleomycin, cetuximab, cisplatin, docetaxel, fluorouracil, methotrexate) |
| Gastric Carcinoma | Ni et al 2012: Asian Pacific Journal of Cancer Prevention 13: 1511 | Chemotherapeutics (e.g. docetaxel, doxorubucin, fluorouracil, mitomycin C, trastuzumab) |

In one embodiment, provided herein is a method for treating a patient diagnosed with a cancer having a dysregulation of TrkA, comprising administering to the patient a therapeutically effective amount of a compound of the invention, or a pharmaceutically acceptable salt thereof, wherein the cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

In one embodiment, the compounds of the present invention are useful for treating cancer in combination with one or more additional therapeutic agents or therapies that work by the same or a different mechanism of action.

In one embodiment, the additional therapeutic agent(s) is selected from receptor tyrosine kinase-targeted therapeutic agents, including cabozantinib, crizotinib, erlotinib, gefitinib, imatinib, lapatinib, nilotinib, pazopanib, pertuzumab, regorafenib, sunitinib, and trastuzumab.

In one embodiment, the additional therapeutic agent(s) is selected from signal transduction pathway inhibitors, including Ras-Raf-MEK-ERK pathway inhibitors (e.g. sorafenib, trametinib, vemurafenib), PI3K-Akt-mTOR-S6K pathway inhibitors (e.g. everolimus, rapamycin, perifosine, temsirolimus) and modulators of the apoptosis pathway (e.g. obataclax).

In one embodiment, the additional therapeutic agent(s) is selected from cytotoxic chemotherapeutics, including arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In one embodiment, the additional therapeutic agent(s) is selected from angiogenesis-targeted therapies, including aflibercept and bevacizumab.

In one embodiment, the additional therapeutic agent(s) is selected from immune-targeted agents, including aldesleukin, ipilimumab, lambrolizumab, nivolumab, sipuleucel-T.

In one embodiment, the additional therapeutic agent(s) is selected from agents active against the TrkA pathway, including NGF-targeted biopharmaceuticals such as NGF antibodies, and panTrk inhibitors.

In one embodiment, the additional therapeutic agent or therapy is radiotherapy, including radioiodide therapy, external-beam radiation and radium 223 therapy.

In one embodiment, the additional therapeutic agent(s) includes any one of the above listed therapies or therapeutic agents which are standards of care in cancers wherein the cancer has a dysregulation of TrkA.

In one embodiment, provided herein is a method of treating cancer in a patient, comprising administering to said patient a compound of the invention or a pharmaceutically acceptable salt thereof, in combination with at least one additional therapy or therapeutic agent selected from radiotherapy (e.g. radioiodide therapy, external-beam radiation, radium 223 therapy), cytotoxic chemotherapeutics (e.g. arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, vincristine), tyrosine kinase targeted-therapeutics (e.g. afatinib, cabozantinib, cetuximab, crizotinib, dabrafenib, erlotinib, gefitinib, imatinib, lapatinib, nilotinib, pazopanib, panitumumab, pertuzumab, regorafenib, sunitinib, trastuzumab), apoptosis modulators and signal transduction inhibitors (e.g. everolimus, perifosine, rapamycin, sorafenib, temsirolimus, trametinib, vemurafenib), immune-targeted therapies (e.g. aldesleukin, interferon alfa-2b, ipilimumab, lambrolizumab, nivolumab, prednisone, sipuleucel-T) and angiogenesis-targeted therapies (e.g. aflibercept, bevacizumab), wherein the amount of the compound of the invention or a pharmaceutically acceptable salt thereof is, in combination with the additional therapy or therapeutic agent, is effective in treating said cancer. These additional therapeutic agents may be administered with one or more compounds of the invention as part of the same or separate dosage forms, via the same or different routes of administration, and on the same or different administration schedules according to standard pharmaceutical practice known to one skilled in the art.

Also provided herein is (i) a pharmaceutical combination for treating cancer in a patient in need thereof, which comprises (a) a compound of the invention or a pharmaceutically acceptable salt thereof, (b) an additional therapeutic agent and (c) optionally at least one pharmaceutically acceptable carrier for simultaneous, separate or sequential use for the treatment of a tumor disease, wherein the amounts of the compound or salt thereof and of the additional therapeutic agent are together effective in treating said cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer a patient in need thereof.

In one embodiment, the combination therapy is for treating a cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

Another embodiment of this invention provides a method of treating inflammation or an inflammatory disease or disorder in a mammal, comprising administering to said mammal in need thereof one or more compounds of Formula I or a pharmaceutically acceptable salt thereof in an amount effective to treat said inflammation. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In one embodiment, the method of treating inflammation or an inflammatory disease or disorder comprises administering a compound of the invention in combination with one or more additional agents. Examples of additional agents include anti-TNF treatments (for example monoclonal antibody such as infliximab (Remicade), adalimumab (Humira), certolizumab pegol (Cimzia), and golimumab (Simponi), or a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

Another embodiment of this invention provides a method of treating *Trypanosoma cruzi* infection in a mammal, comprising administering to said mammal in need thereof one or more compounds of Formula I or a pharmaceutically acceptable salt thereof in an amount effective to treat said *Trypanosoma cruzi* infection.

Another embodiment of this invention provides a method of treating Sjogren's syndrome in a mammal, comprising administering to said mammal in need thereof one or more compounds of Formula I or a pharmaceutically acceptable salt thereof in an amount effective to treat said syndrome.

Another embodiment of this invention provides a method of treating endometriosis in a mammal, comprising administering to said mammal in need thereof one or more compounds of Formula I or a pharmaceutically acceptable salt thereof in an amount effective to treat said endometriosis.

Another embodiment of this invention provides a method of treating diabetic peripheral neuropathy in a mammal, comprising administering to said mammal in need thereof one or more compounds of Formula I or a pharmaceutically acceptable salt thereof in an amount effective to treat said diabetic peripheral neuropathy.

Another embodiment of this invention provides a method of treating prostatitis in a mammal, comprising administering to said mammal in need thereof one or more compounds of Formula I or a pharmaceutically acceptable salt thereof in an amount effective to treat said prostatitis.

Another embodiment of this invention provides a method of treating pelvic pain syndrome in a mammal, comprising administering to said mammal in need thereof one or more compounds of Formula I or a pharmaceutically acceptable salt thereof in an amount effective to treat said pelvic pain syndrome.

Another embodiment of this invention provides a method of treating a neurodegenerative disease in a mammal, comprising administering to said mammal in need thereof one or more compounds of Formula I or a pharmaceutically acceptable salt thereof in an amount effective to treat said neurodegenerative disease.

Another embodiment of this invention provides a method of treating diseases related to an imbalance of the regulation of bone remodeling in a mammal, comprising administering to said mammal in need thereof one or more compounds of Formula I or a pharmaceutically acceptable salt thereof in an amount effective to treat said disease. In one embodiment, the disease is osteoporosis, rheumatoid arthritis, and bone metastases.

In one embodiment, the method for treating diseases related to an imbalance of the regulation of bone remodeling in a mammal comprises administering a TrkA inhibitor of the invention in combination with one or more additional therapeutic agents or therapies. Examples of additional therapeutic agents or therapies include anti-TNF treatments (for example monoclonal antibody such as infliximab (Remicade), adalimumab (Humira), certolizumab pegol (Cimzia), and golimumab (Simponi), or with a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

As used herein, an "effective amount" means an amount of compound that, when administered to a mammal in need of such treatment, is sufficient to (i) treat a particular disease, condition, or disorder which can be treated with a compound of Formula I, or (ii) attenuate, ameliorate, or eliminate one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

The compounds of the present invention can be used in combination with one or more additional therapeutic agents that work by the same or a different mechanism of action. Examples of additional therapeutic agents include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

Also provided herein is a pharmaceutical combination comprising an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), for use in the treatment of pain in a mammal, wherein (a) and (b) can be in separate dosage forms or in the same dosage form.

The term "pharmaceutical combination" as used herein refers to a pharmaceutical therapy resulting from the mixing or combining of more than one active ingredient and includes both fixed and non-fixed combinations of the active ingredients. The term "fixed combination" means that at least one of the compounds of Formula I, and at least one additional therapeutic agent are both administered to a patient simultaneously in the form of a single entity or dosage. The term "non-fixed combination" means that at least one of the compounds of Formula I, and at least one additional therapeutic agent, are administered to a patient as separate entities either simultaneously or sequentially with variable intervening time limits, wherein such administration provides effective levels of the two or more compounds in the body of the patient. These also apply to cocktail therapies, e.g. the administration of three or more active ingredients.

Also provided herein is a method of treating pain in a mammal, comprising co-administering to a mammal in need thereof an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), opioids (such as morphine), calcitonin gene-related peptide receptor antagonists, subtype-selective ion channel modulators, anticonvulsants (for example Pregabalin and gabapentin), dual serotonin-norepinephrin reuptake inhibitors (for example duloxetine, venlafaxine and milnacipran), and tricyclic antidepressants (such as amitriptyline, nortriptyline and desipramine).

The term "co-administering" is meant to encompass administration of the selected therapeutic agents to a single patient, and is intended to include treatment regimens in which the agents are administered by the same or different route of administration or at the same or different times. This term encompasses administration of two or more agents to a mammal so that both agents and/or their metabolites are present in the mammal at the same time. It includes simultaneous administration in separate compositions, administration at different times in separate compositions, and/or administration in a composition in which both agents are present. In some embodiments, the compound(s) of the invention and the other therapeutic agent(s) are administered in a single composition. In some embodiments, compound(s) of the invention and the other agent(s) are admixed in the composition.

Also provided herein is a medicament containing a compound of Formula I for treatment of pain in a mammal in combination with an additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine).

Also provided herein is a medicament containing a therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine) for treatment of pain in a mammal in combination with a compound of Formula I.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Another formulation may be prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

Accordingly, another aspect of the present invention provides a pharmaceutical composition, which comprises a compound of Formula I or a pharmaceutically acceptable salt thereof, as defined hereinabove, together with a pharmaceutically acceptable diluent or carrier.

According to another embodiment, the present invention provides a compound of Formula I or a pharmaceutically acceptable salt thereof, for use in the treatment of pain in a mammal. In one embodiment, the pain is chronic pain. In one embodiment the pain is acute pain. In one embodiment, the pain is inflammatory pain, neuropathic pain, or pain associated with cancer, surgery, or bone fracture.

According to another embodiment, the present invention provides a compound of Formula I or a pharmaceutically acceptable salt thereof, for use in the treatment of cancer in a mammal.

In another embodiment, the present invention provides a compound of Formula I or a pharmaceutically acceptable salt thereof, for use in the treatment of inflammation or an inflammatory disease or disorder in a mammal. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In another embodiment, the present invention provides a compound of Formula I or a pharmaceutically acceptable salt thereof, for use in the treatment of infectious diseases, for example *Trypanosoma cruzi* infection, in a mammal.

In another embodiment, the present invention provides a compound of Formula I or a pharmaceutically acceptable salt thereof, for use in the treatment of Sjogren's syndrome in a mammal.

In another embodiment, the present invention provides a compound of Formula I or a pharmaceutically acceptable salt thereof, for use in the treatment of endometriosis in a mammal.

In another embodiment, the present invention provides a compound of Formula I or a pharmaceutically acceptable salt thereof, for use in the treatment of diabetic peripheral neuropathy in a mammal, In another embodiment, the present invention provides a compound of Formula I or a pharmaceutically acceptable salt thereof, for use in the treatment of prostatitis in a mammal, In another embodiment, the present invention provides a compound of Formula I or a pharmaceutically acceptable salt thereof, for use in the treatment of pelvic pain syndrome in a mammal, In another embodiment, the present invention provides a compound of Formula I or a pharmaceutically acceptable salt thereof, for use in the treatment of a neurodegenerative disease in a mammal.

According to a further aspect, the present invention provides the use of a compound of Formula I or a pharmaceutically acceptable salt thereof, in the manufacture of a medicament for the treatment of a condition selected from pain, cancer, inflammation, neurodegenerative disease or *Trypanosoma cruzi* infection. In one embodiment, the condition is chronic pain. In one embodiment, the condition is acute pain. In one embodiment, the pain is inflammatory pain, neuropathic pain, or pain associated with cancer, surgery, or bone fracture. In one embodiment, the condition is cancer. In one embodiment, the condition is inflammation. In one embodiment, the condition is a neurodegenerative disease. In one embodiment, the condition is *Trypanosoma cruzi* infection. In one embodiment, the condition is Sjogren's syndrome. In one embodiment, the condition is endometriosis. In one embodiment, the condition is diabetic peripheral neuropathy. In one embodiment, the condition is prostatitis. In one embodiment, the condition is pelvic pain syndrome.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel or C-18 reverse phase column, or on a silica SepPak cartridge (Waters).

Biological Assays

Example A-1

TrkA Kinase Binding Assay

TrkA binding activity was determined in a TrkA LanthaScreen™ Eu Kinase Binding Assay. 5 nM His-tagged recombinant human TrkA (6HIS tagged cytoplasmic domain from Invitrogen, Catalog No. PV3144) was incubated with 4 nM Alexa-Fluor® Tracer 236 (Invitrogen Cat. No. PV5592), 2 nM biotinylated anti-His (Invitrogen Cat. No. PV6090), and 2 nM europium-labeled Streptavidin (Invitrogen Cat. No. PV5899), in buffer (25 mM MOPS, pH 7.5, 5 mM $MgCl_2$, 0.005% Triton X-100). Three fold serial dilutions of compounds of the invention in DMSO were added to a final percentage of 2% DMSO. After 60-minute incubation at 22° C., the reaction was measured using the EnVision mutlimode plate reader (PerkinElmer) via TR-FRET dual wavelength detection at 615 nM and 665 nM. The percent of control was calculated using a ratiometric emission factor. The $IC_{50}$ values were determined by fitting a four parameter model to the percent of control data.

Table A provides averaged $IC_{50}$ values for compounds of the invention when tested in the assay of Example A, where A represents an averaged $IC_{50}$ value <100 nM; and B represents an averaged $IC_{50}$ value from 100 to 1,000 nM.

TABLE A

| Ex. # | TrkA enzyme $IC_{50}$ (nM) |
|---|---|
| 1 | B |
| 2 | B |
| 3 | A |
| 4 | A |
| 5 | B |
| 6 | A |
| 7 | A |
| 8 | A |
| 9 | A |
| 10 | A |
| 11 | A |
| 12 | A |
| 13 | B |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | B |

Example A-2 p38 Kinase Binding Assay p38α binding activity was determined in a p38α LanthaScreen™ Eu Kinase Binding Assay. 5 nM of inactive, GST-tagged recombinant human p38α (GST-tagged cytoplasmic domain from Invitrogen, Catalog No. PV3305) was incubated with 5 nM Alexa-Fluor® Tracer 199 (Invitrogen Cat. No. PV5830), and 2 nM europium labeled anti-GST antibody (Invitrogen Cat. No. PV5594), in buffer (25 mM [$Na^+$] HEPES pH 7.3, 10 mM $MgCl_2$, 100 μM $NaVO_4$). Three fold serial dilutions of compounds of the invention in DMSO were added to a final percentage of 2% DMSO. After 60-minute incubation at 22° C., the reaction was measured using the EnVision multimode plate reader (PerkinElmer) via TR-FRET dual wavelength detection at 615 nM and 665 nM. The percent of control was calculated using a ratiometric emission factor. The $IC_{50}$ values were determined by fitting a four parameter model to the percent of control data. The compounds of Examples 1-28 were tested in this assay, and all compounds were found to be 1000 fold more potent against TrkA than p38α.

Example B

Off-Target Kinase Profiling

A representative compound of the invention (Example 20) was tested for off-target kinase activity at a concentration of 10 μM by Millipore, Inc. in their KinaseProfiler™ service against all the kinases available in their full kinase panel. The compound was run in duplicate at a concentration of ATP near the Km for each individual kinase according to Millipore's specifications. The results are shown in Table B. Data are reported as percent of control (POC) and are the average of the two replicates.

In the KinaseProfiler™ the compound of Example 20 showed remarkable and unexpected selectivity for inhibiting TrkA and TrkB versus other kinases in the panel. In fact, the compound was largely inactive against off-target kinases at a concentration of 10 μM, and thus would not be expected to inhibit off-target kinases at therapeutic doses in mammals. The ability of compounds of the invention to selectively inhibit the Trk pathway without inhibiting other off-target kinases could translate into drug profiles that are essentially free of side-effects related to inhibition of off-target kinases. Such a drug profile would represent a safer approach to treating pain, inflammation, cancer and certain skin diseases than has been previously reported.

TABLE B

| Kinase | Example 20 Avg. POC |
|---|---|
| Abl | 114 |
| Abl2 | 112.5 |

TABLE B-continued

| Kinase | Example 20 Avg. POC |
|---|---|
| AKT1 | 109 |
| AKT2 | 131 |
| AKT3 | 104 |
| ALK | 114 |
| ALK4 | 98.5 |
| AMPK(A1/B1/G1) | 108.5 |
| ARK5 | 104 |
| AURKA | 118 |
| Axl | 97 |
| BLK_m | 113 |
| Bmx | 103.5 |
| BrSK1 | 112.5 |
| BrSK2 | 116 |
| BTK | 112.5 |
| CAMK1 | 105.5 |
| CAMK1d | 107.5 |
| CAMK2b | 102 |
| CAMK2d | 102 |
| CAMK2g | 113 |
| CAMK4 | 105 |
| CDK1/cyclinB | 99 |
| CDK2/cyclinA | 112 |
| CDK2/cyclinE | 118.5 |
| CDK3/cyclinE | 111 |
| CDK5/p25 | 111 |
| CDK5/p35 | 121 |
| CDK6/cyclinD3 | 103.5 |
| CDK7/cyclinH/MAT1 | 101.5 |
| CDK9/cyclinT1 | 109.5 |
| CHK1 | 103.5 |
| CHK2 | 138 |
| CK1_y | 104 |
| CK1delta | 93 |
| CK1gamma1 | 109 |
| CK1gamma2 | 110 |
| CK1gamma3 | 112 |
| CK2 | 109 |
| CK2alpha2 | 104 |
| CLK2 | 106.5 |
| CLK3 | 107 |
| c-RAF | 118.5 |
| CSK | 104.5 |
| DAPK1 | 103 |
| DAPK2 | 104 |
| DAPK3 | 103 |
| DCAMKL2 | 126.5 |
| DDR2 | 106 |
| DMPK | 105.5 |
| DRAK1 | 107 |
| DYRK2 | 85.5 |
| eEF-2K | 108 |
| EGFR | 107.5 |
| EphA1 | 99 |
| EphA2 | 107.5 |
| EphA3 | 98 |
| EphA4 | 106 |
| EphA5 | 123 |
| EphA7 | 104.5 |
| EphA8 | 98.5 |
| EphB1 | 85 |
| EphB2 | 104 |
| EphB3 | 107 |
| EphB4 | 102 |
| ErbB4 | 97.5 |
| ERK1 | 115 |
| ERK2 | 96 |
| FAK | 109.5 |
| Fer | 91.5 |
| Fes | 113.5 |
| FGFR1 | 102 |
| FGFR2 | 106 |
| FGFR3 | 101 |
| FGFR4 | 90 |
| Fgr | 121 |
| Flt1 | 100 |
| Flt3 | 110 |
| Flt4 | 110.5 |

TABLE B-continued

| Kinase | Example 20 Avg. POC |
|---|---|
| Fms | 87.5 |
| Fyn | 128.5 |
| GRK5 | 108 |
| GRK6 | 110 |
| GRK7 | 96.5 |
| GSK3alpha | 109.5 |
| GSK3beta | 129 |
| Haspin | 93.5 |
| Hck | 110 |
| HIPK1 | 111 |
| HIPK2 | 102 |
| HIPK3 | 105.5 |
| IGF-1R | 73 |
| IGF-1R Activated | 100 |
| IKKalpha | 121 |
| IKKbeta | 107.5 |
| IR | 87.5 |
| IR Activated | 108 |
| IRAK1 | 109.5 |
| IRAK4 | 124 |
| IRR | 96 |
| ITK | 122.5 |
| JAK2 | 117 |
| JAK3 | 115 |
| JNK1alpha1 | 105 |
| JNK2alpha2 | 107.5 |
| JNK3 | 124.5 |
| KDR | 107 |
| KIT | 117.5 |
| Lck | 135.5 |
| LIMK1 | 103 |
| LKB1 | 105 |
| LOK | 108.5 |
| Lyn | 104.5 |
| MAP3K5 | 88 |
| MAP4K2 | 112 |
| MAPKAP-K2 | 106.5 |
| MAPKAP-K3 | 105 |
| MAPKAP-K5 | 88.5 |
| MARK1 | 103.5 |
| MARK2 | 98 |
| MEK1 | 111 |
| MELK | 97.5 |
| Mer | 116.5 |
| Met | 110 |
| MINK | 99 |
| MKK4_m | 113 |
| MKK6 | 83 |
| MKK7beta[1] | −2 |
| MKNK2 | 103 |
| MLK1 | 100 |
| MRCKalpha | 101.5 |
| MRCKbeta | 118.5 |
| MSK1 | 121 |
| MSK2 | 126 |
| MSSK1 | 108.5 |
| MST1 | 89.5 |
| MST2 | 107.5 |
| MST3 | 104 |
| mTOR | 108 |
| mTOR/FKBP12 | 110.5 |
| MuSK | 108.5 |
| MYLK | 110 |
| NEK11 | 109.5 |
| NEK2 | 91 |
| NEK3 | 103 |
| NEK6 | 92.5 |
| NEK7 | 105.5 |
| NLK | 99 |
| p38alpha | 97.5 |
| p38beta | 98.5 |
| p38delta | 105 |
| p38gamma | 105.5 |
| p70S6K | 112 |
| PAK2 | 100.5 |
| PAK3 | 219.5 |
| PAK4 | 97.5 |

TABLE B-continued

| Kinase | Example 20 Avg. POC |
|---|---|
| PAK5 | 105.5 |
| PAK6 | 102 |
| PASK | 111 |
| PDGFRalpha | 105.5 |
| PDGFRbeta | 114 |
| PDK1 | 119.5 |
| PhKgamma2 | 98.5 |
| Pim-1 | 105 |
| Pim-2 | 122.5 |
| Pim-3 | 98 |
| PKAC-alpha | 114 |
| PKCalpha | 103.5 |
| PKCbetaI | 101 |
| PKCbetaII | 106 |
| PKCdelta | 106.5 |
| PKCepsilon | 107.5 |
| PKCeta | 105.5 |
| PKCgamma | 111 |
| PKCiota | 101.5 |
| PKCmu | 100.5 |
| PKCtheta | 111.5 |
| PKCzeta | 104 |
| PKD2 | 113.5 |
| Plk1 | 104 |
| Plk2 | 106 |
| Plk3 | 99.5 |
| PRK2 | 104 |
| PRKG1alpha | 111.5 |
| PRKG1beta | 124 |
| PrKX | 120.5 |
| PTK5 | 111 |
| PTK6 | 114 |
| Pyk2 | 98.5 |
| Ret | 97.5 |
| RIPK2 | 97.5 |
| ROCK-I | 95.5 |
| ROCK-II | 122 |
| Ron | 100 |
| Ros | 95.5 |
| Rse | 102.5 |
| Rsk1 | 115 |
| Rsk2 | 110.5 |
| Rsk3 | 107.5 |
| Rsk4 | 147 |
| SGK1 | 119 |
| SGK2 | 105 |
| SGK3 | 109 |
| SIK | 97.5 |
| SRC | 107 |
| SRPK1 | 113.5 |
| SRPK2 | 100 |
| STK33 | 109.5 |
| Syk | 99.5 |
| TAK1 | 97 |
| TAO1 | 106 |
| TAO2 | 104.5 |
| TAO3 | 103 |
| TBK1 | 114 |
| TEC Activated | 107 |
| Tie2 | 119 |
| TLK2 | 105 |
| TNK2 | 94.5 |
| TrkA | 0 |
| TrkB | 0.5 |
| TSSK1 | 107 |
| TSSK2 | 106 |
| Txk | 130 |
| ULK2 | 109 |
| ULK3 | 108 |
| VRK2 | 117.5 |
| WNK2 | 120 |
| WNK3 | 115.5 |
| Yes | 109 |
| ZAP-70 | 102.5 |

[1]The POC for MKK7beta was verified as a false positive.

Preparation of Synthetic Intermediates

Preparation A

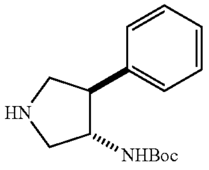

tert-butyl trans-4-phenylpyrrolidin-3-ylcarbamate

Step A: Preparation of trans-1-benzyl-3-nitro-4-phenylpyrrolidine

To a solution of (E)-(2-nitrovinyl)benzene (149 g, 1.00 mol) in dry DCM (2 L) was added TFA (19.5 mL, 0.250 mol) and the mixture was cooled to −15° C. N-methoxymethyl-N-(trimethylsilylmethyl)benzylamine (274 g, 1.00 mol) in dry DCM (500 mL) was added over 3 hours while maintaining the reaction temperature between −15 and −10° C. The reaction was warmed to ambient temperature and stirred for 18 hours. The reaction mixture was washed with 2N NaOH (500 mL) and treated with 2N HCl (1 L). The resulting white suspension was stirred for 1 hour and was filtered. The collected solid was washed with DCM and partitioned into DCM (1 L) and 2N NaOH (750 mL). The organic layer was separated and the aqueous layer was extracted with DCM (2×1 L). The combined organic layers were dried with $MgSO_4$, filtered and concentrated to afford the title product as an off-white solid (205 g, 73% yield). MS (apci) in/z=283.1 (M+H).

Step B: Preparation of trans-1-benzyl-4-phenylpyrrolidin-3-amine

To a suspension of trans-1-benzyl-3-nitro-4-phenyl-pyrrolidine (93.9 g, 333 mmol) in EtOH (1.20 L) was added concentrated HCl (450 mL) followed by zinc dust (173 g, 2.66 mol) in small portions over 1.5 hours while maintaining the temperature between 55-60° C. The reaction mixture was stirred at ambient temperature for 18 hours, cooled in an ice/water bath and treated with concentrated $NH_4OH$ (900 mL). The mixture (pH 10-11) was filtered and the collected zinc was washed with $CHCl_3$. The filtrate was phase-separated, and the aqueous layer was extracted with $CHCl_3$ (2×400 mL). The combined organics were washed with $H_2O$, brine and dried with $MgSO_4$. The dried solution was filtered and concentrated to afford the title compound as an amber oil (85.0 g, 100% yield). MS (apci) m/z=253.2 (M+H).

Step C: Preparation of trans-(1-benzyl-4-phenyl-pyrrolidin-3-yl)-carbamic acid tert-butyl ester To a mixture of trans-1-benzyl-4-phenylpyrrolidin-3-amine (85.0 g, 333 mmol) and triethylamine (69.6 mL, 500 mmol) in dry THF (750 mL) was slowly added $(Boc)_2O$ (72.7 g, 333 mmol) in portions over 30 minutes. The reaction mixture was stirred at ambient temperature for 16 hours and was concentrated under vacuum. The residue was dissolved in $CHCl_3$ and was washed with aqueous $Na_2CO_3$ and brine. The organic layer was dried with $MgSO_4$, filtered and concentrated to afford the title compound as a pale-yellow solid (116 g, 99% yield). MS (apci) m/z=353.0 (M+H).

Step D: Preparation of tert-butyl trans-4-phenylpyrrolidin-3-ylcarbamate

A 2 gallon Parr reactor was charged with trans-(1-benzyl-4-phenyl-pyrrolidin-3-yl)-carbamic acid tert-butyl ester (114 g, 323 mmol), EtOH (2 L) and 10% Pd/C (50 wt. % $H_2O$, 11.0 g). The reactor was purged with $N_2$, filled with $H_2$ to 56-57 psi and the reaction mixture agitated at 80° C. until complete by HPLC analysis. The reaction mixture was filtered and the filtrate concentrated to provide the crude product as a yellow solid. The crude material was triturated with toluene to afford the title product as a white solid (68.4 g, 78% yield). MS (apci) m/z=262.9 (M+H).

Preparation B

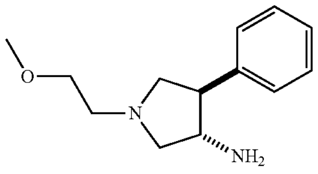

2 HCl trans-1-(2-methoxyethyl)-4-phenylpyrrolidin-3-amine dihydrochloride

Step A: Preparation of tert-butyl trans-1-(2-methoxyethyl)-4-phenylpyrrolidin-3-ylcarbamate To a solution of tert-butyl trans-4-phenylpyrrolidin-3-ylcarbamate (Preparation A, 4.82 g, 17.5 mmol) in dry DMF (50 mL) was added sequentially DIEA (9.12 mL, 52.4 mmol) and 1-bromo-2-methoxyethane (1.97 mL, 20.9 mmol). The mixture was stirred at ambient temperature for 46 hours and poured into $H_2O$ (300 mL). The mixture was extracted with EtOAc (3×150 mL) and the combined extracts were washed with brine, dried over $MgSO_4$/activated charcoal and filtered through a $SiO_2$ plug capped with packed $MgSO_4$ (EtOAc for elution). The solution was concentrated and the residue dried under vacuum to yield the product as a white solid (5.15 g, 92% yield). MS (apci) m/z=321.1 (M+H).

Step B: Preparation of trans-1-(2-methoxyethyl)-4-phenylpyrrolidin-3-amine dihydrochloride To a solution of tert-butyl trans-1-(2-methoxyethyl)-4-phenylpyrrolidin-3-ylcarbamate (5.10 g, 15.9 mmol) in 2:1 EtOAc-MeOH (150 mL) was added 4 N HCl in dioxane (59.7 mL, 239 mmol). The mixture was stirred at ambient temperature for 90 minutes and then concentrated under vacuum. The resulting foam was treated with EtOAc (200 mL), sonicated for 5 minutes and stirred vigorously until a fine white suspension formed. The suspension was filtered, washed with EtOAc and dried under vacuum to afford the title compound as a white powder (5.10 g, 100% yield). MS (apci) m/z=221.1 (M+H).

Preparation C

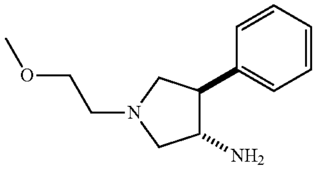

HCl
HCl (3S,4R)-1-(2-methoxyethyl)-4-phenylpyrrolidin-3-amine dihydrochloride

Step A: Preparation of (R)-3-cinnamoyl-4-phenyloxazolidin-2-one

A THF (50 mL) solution of (R)-4-phenyloxazolidin-2-one (5.90 g, 36.2 mmol) was cooled to −78° C. and treated with lithium bis(trimethylsilyl)amide (36.9 mL, 36.9 mmol, 1.0 M in THF) dropwise over 15 minutes. After 15-minute stirring at −78° C., a THF (10 mL) solution of cinnamoyl chloride (6.33 g, 38.0 mmol) was introduced. The mixture was stirred for 1 hour at −78° C. and 2 hours at ambient temperature before it was quenched with saturated $NaHCO_3$ (50 mL) and stirred for 1 hour. The mixture was diluted with EtOAc (200 mL), washed with water and brine, dried over $MgSO_4$, filtered and concentrated to give the product as a pale yellow solid (10.6 g, 99.9% yield). MS (apci) m/z=293.9 (M+H).

Step B: Preparation of (R)-3-((3S,4R)-1-(2-methoxyethyl)-4-phenylpyrrolidine-3-carbonyl)-4-phenyloxazolidin-2-one A solution of (R)-3-cinnamoyl-4-phenyloxazolidin-2-one (8.00 g, 27.3 mmol) and TFA (0.210 mL, 2.73 mmol) in dry toluene (500 mL) was cooled to 5-10° C. and a solution of 2-methoxy-N-(methoxymethyl)-N-((trimethylsilyl)methyl)ethanamine (Preparation D, 8.40 g, 40.9 mmol) in dry toluene (30 mL) was added dropwise. The reaction mixture was warmed to ambient temperature and stirred for 3 hours. The mixture was washed with saturated $NaHCO_3$ and water and dried with $MgSO_4$. The dried solution was filtered, concentrated under vacuum and the crude residue was purified by silica column chromatography (16-20% EtOAc/hexanes) to afford the title product (6.5 g, 60% yield). MS (apci) m/z=395.2 (M+H).

Step C: Preparation of (3S,4R)-1-(2-methoxyethyl)-4-phenylpyrrolidine-3-carboxylic acid 1M aqueous LiOH (41.2 mL, 41.2 mmol) was cooled to 0-5° C. and treated $H_2O_2$ (3.37 mL, 33.0 mmol, 30 wt %) followed by (R)-((3S,4R)-1-(2-methoxyethyl)-4-phenylpyrrolidine-3-carbonyl)-4-phenyloxazolidin-2-one (6.50 g, 16.5 mmol) in THF (100 mL) over 10 minutes. After stirring for 1 hour, 2.0 M aqueous $Na_2SO_3$ (33.0 mL, 65.9 mmol) was introduced and the reaction mixture was warmed to ambient temperature. After stirring for 10 minutes, the mixture was washed with EtOAc (50 mL). The aqueous layer was acidified with 1 N HCl to pH 3-5 and treated with NaCl (10 g). The mixture was extracted with 10% iPrOH/DCM and the the combined organic fractions were dried with $MgSO_4$, filtered and concentrated to give the title product (4.11 g, 100% yield). MS (apci) m/z=250.1 (M+H).

Step D: Preparation of benzyl (3S,4R)-1-(2-methoxyethyl)-4-phenylpyrrolidin-3-ylcarbamate To a solution of (3S,4R)-1-(2-methoxyethyl)-4-phenylpyrrolidine-3-carboxylic acid (4.11 g, 16.5 mmol) in toluene (70 mL) was added TEA (5.74 mL, 41.2 mmol) followed by diphenylphosphoryl azide (4.99 mL, 23.1 mmol). The mixture was stirred at ambient temperature for 1 hour and then heated to reflux for 1 hour. Benzyl alcohol (3.42 mL, 33.0 mmol) was added and the reaction mixture was refluxed for 15 hours. The cooled reaction mixture was treated with EtOAc and was washed with water, dried over $MgSO_4$, filtered and concentrated under vacuum. The crude material was purified by silica column chromatography (1% MeOH/DCM) to afford the title product (2.5 g, 43% yield). MS (apci) m/z=355.2 (M+H).

Step E: Preparation of (3S,4R)-1-(2-methoxyethyl)-4-phenylpyrrolidin-3-amine dihydrochloride A mixture of benzyl (3S,4R)-1-(2-methoxyethyl)-4-phenylpyrrolidin-3-ylcarbamate (0.257 g, 0.725 mmol) and TFA (3.91 mL, 50.8 mmol) was heated at 60° C. for 17 hours. The reaction mixture was cooled and concentrated under vacuum using toluene to azeotrope. The residue was treated with 2 N HCl in $Et_2O$ and concentrated to give the title compound (0.21 g, 100% yield) as an off-white solid. MS (apci) m/z=221.2 (M+H).

Preparation D

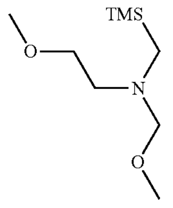

2-methoxy-N-(methoxymethyl)-N-((trimethylsilyl)methyl)ethanamine

Step A: Preparation of 2-methoxy-N-((trimethylsilyl)methyl)ethanamine

To a DMSO solution (15 mL) of 2-methoxyethanamine (14.2 mL, 163 mmol) at 90° C. was added a DMSO (10 mL) solution of (chloromethyl)trimethylsilane (11.4 mL, 81.5 mmol) by addition funnel over 40 minutes. The mixture was heated at 90° C. for 3.5 hours then cooled to ambient temperature. The reaction mixture was diluted with $H_2O$ (150 mL) and extracted with EtOAc (2×150 mL). The combined organic extracts were washed with brine (150 mL), dried with $MgSO_4$, filtered and concentrated to yield the product as a yellow oil (8.14 g, 62% yield). MS (apci) m/z=162.0 (M+H).

Step B: Preparation of 2-methoxy-N-(methoxymethyl)-N-((trimethylsilyl)methyl)ethanamine A MeOH (2.45 mL) solution of aqueous formaldehyde (37% wt. %, 4.91 g, 60.6 mmol) was cooled to 0° C. and treated dropwise with 2-methoxy-N-((trimethylsilyl)methyl)ethanamine (8.14 g, 50.5 mmol). The resulting biphasic mixture was stirred at 0° C. for 3 hours, $K_2CO_3$ (6.97 g, 50.5 mmol) was added and the mixture was stirred at 0° C. for 1 hour. The yellow oil was decanted onto fresh $K_2CO_3$ (2.00 g, 14.4 mmol) and the mixture was stirred at ambient temperature for 2 hours. The yellow oil was decanted, the $K_2CO_3$ was washed with $Et_2O$ (2×10 mL), and the $Et_2O$ washings were combined with the decanted yellow oil and concentrated to yield the title compound as a yellow oil (9.92 g, 96% yield). $^1H$ NMR ($CDCl_3$) δ 4.00 (s, 2H), 3.37-3.43 (m, 2H), 3.29 (s, 3H), 3.19 (s, 3H), 2.77-2.82 (m, 2H), 2.18 (s, 2H), 0.00 (s, 9H).

Preparation E1

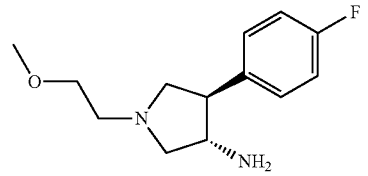

(3S,4R)-4-(4-fluorophenyl)-1-(2-methoxyethyl)pyrrolidin-3-amine

Step A: Preparation of (E)-1-fluoro-4-(2-nitrovinyl)benzene

Acetic acid (2.0 L, 35.5 mol) and ammonium acetate (310.5 g, 4.03 mol) were stirred at ambient temperature for 1 hour, then nitromethane (611 mL, 11.3 mol) and 4-fluorobenzaldehyde (200 g, 1.61 mol) were added and the reaction mixture was heated to 90° C. for 3 hours. The reaction was allowed to cool to ambient temperature, then $H_2O$ (4 L) was added over 2 hours with mechanical stirring. The suspension was stirred 1 hour, then filtered and washed with 2:1 water/acetic acid (500 mL) The solids were dried in a vacuum oven (50° C.) to afford the title product as a pale yellow solid (238 g, 1.42 mol, 88% yield). $^1H$ NMR ($CDCl_3$) δ 7.98 (1H), 7.55 (3H), 7.16 (2H).

Step B: Preparation of trans-3-(4-fluorophenyl)-1-(2-methoxyethyl)-4-nitro-pyrrolidine To a suspension of (E)-1-fluoro-4-(2-nitrovinyl)benzene (201 g, 1.20 mol) in DCM (1.09 L) and TFA (9.3 mL, 120 mmol) was added dropwise over 30 minutes 2-methoxy-N-(methoxymethyl)-N-((trimethylsilyl)methyl)ethanamine (Preparation D; 383 g, 1.86 mol) and the internal reaction temperature was maintained between 23-36° C. by cooling in an ice bath. The reaction mixture was poured into aqueous phosphate buffer solution (pH 7, 500 mL) and diluted with DCM (300 mL). The phases were separated and the aqueous phase was extracted with DCM (400 mL). The organic phases were combined, washed with brine (300 mL), dried ($MgSO_4$), filtered and concentrated under reduced pressure. The crude oil was purified by silica column chromatography eluting with 40% EtOAc/heptane to afford the title compound as a yellow oil (245 g, 76% yield). MS (apci) m/z=269.1 (M+H).

Step C: Preparation of trans-4-(4-fluorophenyl)-1-(2-methoxyethyl)pyrrolidin-3-amine To a solution of trans-3-(4-fluorophenyl)-1-(2-methoxyethyl)-4-nitropyrrolidine (289 g, 1.08 mol) in EtOH (1 L) was added platinum(IV) oxide (24.5 g, 108 mmol) in a Parr vessel and installed into a Parr shaker. The vessel was evacuated and backfilled with nitrogen (3×), then evacuated and backfilled with hydrogen (60 psi). The vessel was recharged with hydrogen as needed until the reaction was complete. The reaction mixture was filtered through Celite® and rinsed with MeOH (50 mL), then concentrated under reduced pressure to afford the title compound as a yellow oil (243 g, 95% yield). MS (apci) m/z=239.1 (M+H).

Step D: Preparation of (3 S,4R)-4-(4-fluorophenyl)-1-(2-methoxyethyl)pyrrolidin-3-amine (2S,3S)-2,3-bis(4-methylbenzoyloxy)succinate To a solution of (3 S,4R)-4-(4-fluorophenyl)-1-(2-methoxyethyl)pyrrolidin-3-amine (120 g, 504 mmol) in THF (3.0 L) and $H_2O$ (333 mL) was added di-p-toluoyl-D-tartaric acid (195 g, 504 mmol). Stirred at ambient temperature for 1 hour, then placed in a freezer (−11° C.) for 18 hours. The mixture was stirred to give a slurry, filtered, and rinsed with $Et_2O$ (4×100 mL). The solid was dried in vacuum oven (40° C.) for 4 hours, then recrystallized twice by the following procedure: the solid was dissolved in THF (1.06 mL) and $H_2O$ (118 mL) with heating to 45° C., then allowing to cool to ambient temperature over 2 hours, then placed in a freezer (−11° C.) for 18 hours; the mixture was stirred to give a slurry, filtered, and rinsed with $Et_2O$ (4×100 mL). After two recrystallizations, the solid was dried in vacuum oven (40° C.) for 18 hours to afford the title compound as a white crystalline solid (96 g, 31% yield). MS (apci) m/z=239.2 (M+H).

Step E: Preparation of (3S,4R)-4-(4-fluorophenyl)-1-(2-methoxyethyl)pyrrolidin-3-amine (3 S,4R)-4-(4-fluorophenyl)-1-(2-methoxyethyl)pyrrolidin-3-amine (2S,3S)-2,3-bis(4-methylbenzoyloxy)succinate (20 g, 32.0 mmol) was dissolved in DCM (300 mL) and washed with 1M NaOH (2×200 mL). The combined aqueous phases were extracted with DCM (200 mL). The combined organic extracts were washed with brine (200 mL), dried ($MgSO_4$), filtered and concentrated, then dried under vacuum to afford the title compound as a yellow oil (6.17 g, 81%, >99% ee). MS (apci) m/z=239.1 (M+H).

The following pyrrolidine intermediates were made according to the method of Preparation E1, using the appropriate benzaldehyde in Step A and replacing EtOH and platinum(IV) oxide with MeOH and Raney nickel respectively in Step C. For preparation E3, the 90% THF/$H_2O$ in Step D was replaced with 85% MeOH/$H_2O$.

| Preparation # | Structure | Name | Data |
|---|---|---|---|
| E2 | 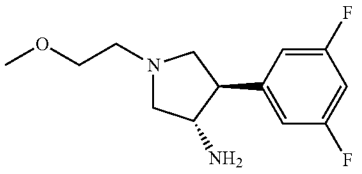 [SMILES: COCCN1C[C@@H](N)[C@H](c2cc(F)cc(F)c2)C1] | (3S,4R)-4-(3,5-difluorophenyl)-1-(2-methoxyethyl)pyrrolidin-3-amine | MS (apci) m/z = 257.1 (M + H) |
| E3 | 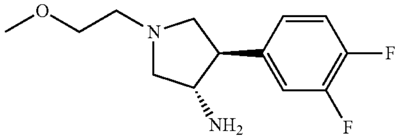 [SMILES: COCCN1C[C@@H](N)[C@H](c2ccc(F)c(F)c2)C1] | (3S,4R)-4-(3,4-difluorophenyl)-1-(2-methoxyethyl)pyrrolidin-3-amine (2S,3S)-2,3-bis(4-methylbenzoyloxy)succinate | MS (apci) m/z = 257.1 (M + H) |

Preparation G-100

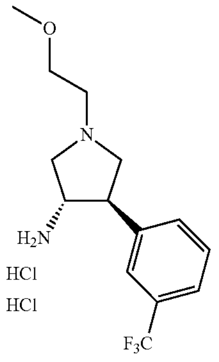

(3S,4R)-1-(2-methoxyethyl)-4-(3-(trifluoromethyl)phenyl)pyrrolidin-3-amine dihydrochloride Step A: Preparation of tert-butyl (3S,4R)-1-(2-methoxyethyl)-4-(3-(trifluoromethyl)-phenyl)pyrrolidin-3-ylcarbamate A solution of tert-butyl (3S,4R)-4-(3-(trifluoromethyl)phenyl)-pyrrolidin-3-ylcarbamate (100 mg, 0.303 mmol, commercially available), N,N-diethylpropan-2-amine (0.145 mL, 0.908 mmol) and 1-bromo-2-methoxyethane (0.0361 mL, 0.363 mmol) in DMF (1 mL) was stirred at ambient temperature for 2 hours, then heated to 60° C. for 4 hours, then cooled to ambient temperature overnight. After partitioning between EtOAc and saturated $NaHCO_3$ (10 mL each), the organic layer was washed with water and brine (2×10 mL each), dried over $Na_2SO_4$, filtered and concentrated to yield the crude product as white solid (80 mg, 68% yield). LCMS (apci) m/z=389.1 (M+H).

Step B: Preparation of (3S,4R)-1-(2-methoxyethyl)-4-(3-(trifluoromethyl)phenyl)-pyrrolidin-3-amine dihydrochloride A solution of tert-butyl (3S,4R)-1-(2-methoxyethyl)-4-(3-(trifluoromethyl)phenyl)pyrrolidin-3-ylcarbamate (80.0 mg, 0.206 mmol) in 5-6 N HCl in IPA (4.12 mL, 20.6 mmol) was stirred at ambient temperature for 1 hour, followed by concentrating in vacuo and triturating with $Et_2O$ to afford the product as beige solid (74 mg, 99.5% yield). LCMS (apci) m/z=289.1 (M+H).

Preparation H-100

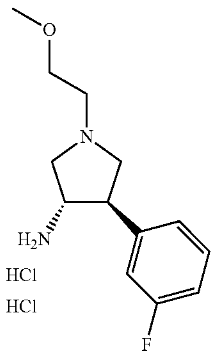

(3S,4R)-4-(3-fluorophenyl)-1-(2-methoxyethyl)pyrrolidin-3-amine dihydrochloride

Prepared according to the method of Preparation G-100, replacing tert-butyl (3S,4R)-4-(3-(trifluoromethyl)phenyl)-pyrrolidin-3-ylcarbamate with tert-butyl (3S,4R)-4-(3-fluorophenyl)pyrrolidin-3-ylcarbamate to afford the title compound. LCMS (apci) m/z=239.1 (M+H).

Preparation I-100

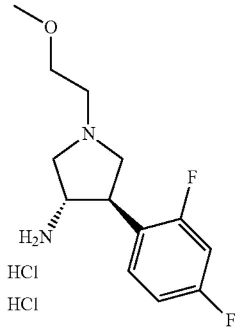

(3S,4R)-4-(2,4-difluorophenyl)-1-(2-methoxyethyl) pyrrolidin-3-amine dihydrochloride Prepared according to the method of Preparation G-100, replacing tert-butyl (3S,4R)-4-(3-(trifluoromethyl)phenyl)-pyrrolidin-3-ylcarbamate with tert-butyl (3S,4R)-4-(2,4 di-fluoro-phenyl)pyrrolidin-3-ylcarbamate to afford the title compound. LCMS (apci) m/z=257.1 (M+H).

Preparation J-100

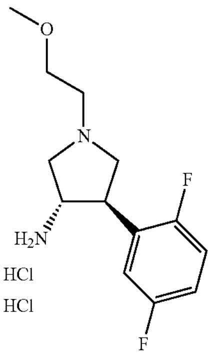

(3S,4R)-4-(2,5-difluorophenyl)-1-(2-methoxyethyl) pyrrolidin-3-amine dihydrochloride Prepared according to the method of Preparation G-100, replacing tert-butyl (3S,4R)-4-(3-(trifluoromethyl)phenyl)-pyrrolidin-3-ylcarbamate with tert-butyl (3S,4R)-4-(2,5 di-fluoro-phenyl)pyrrolidin-3-ylcarbamate to afford the title compound. LCMS (apci) m/z=257.1 (M+H).

Preparation K-100

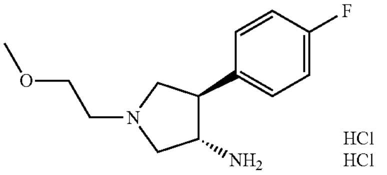

(3S,4R)-4-(4-fluorophenyl)-1-(2-methoxyethyl)pyrrolidin-3-amine dihydrochloride

Prepared according to the method described in Preparation E1, replacing cinnamoyl chloride with (E)-3-(4-fluorophenyl)acryloyl chloride. MS (apci) m/z=239.1 (M+H).

The following pyrrolidine intermediates were made according to the method of Preparation E1, using the appropriate benzaldehyde in Step A and replacing EtOH and platinum(IV) oxide with MeOH and Raney nickel respectively in Step C.

| Preparation # | Structure | Name | Data |
|---|---|---|---|
| L-100 | 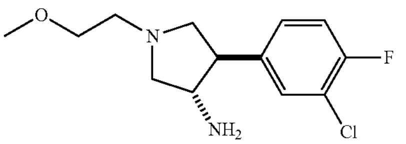 [SMILES: COCCN1C[C@@H](N)[C@H](c2ccc(F)c(Cl)c2)C1] | trans-4-(3-chloro-4-fluorophenyl)-1-(2-methoxyethyl) pyrrolidin-3-amine | MS (apci) m/z = 273.1 (M + H) |
| L-101 | 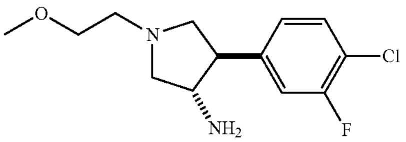 [SMILES: COCCN1C[C@@H](N)[C@H](c2ccc(Cl)c(F)c2)C1] | trans-4-(4-chloro-3-fluorophenyl)-1-(2-methoxyethyl) pyrrolidin-3-amine | MS (apci) m/z = 273.1 (M + H) |

-continued

| Preparation # | Structure | Name | Data |
|---|---|---|---|
| L-102 | 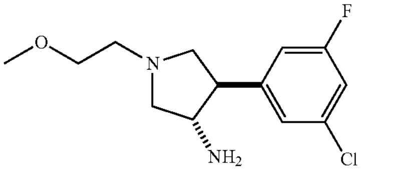 [SMILES: COCCN1C[C@@H](N)[C@H](c2cc(F)cc(Cl)c2)C1] | trans-4-(3-chloro-5-fluoro-phenyl)-1-(2-methoxyethyl) pyrrolidin-3-amine | MS (apci) m/z = 273.1 (M + H) |
| L-103 | 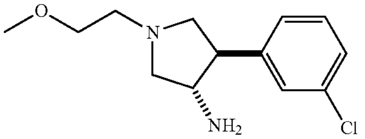 [SMILES: COCCN1C[C@@H](N)[C@H](c2cccc(Cl)c2)C1] | trans-4-(3-chlorophenyl)-1-(2-methoxyethyl)pyrrolidin-3-amine | MS (apci) m/z = 255.1 (M + H) |
| L-104 | 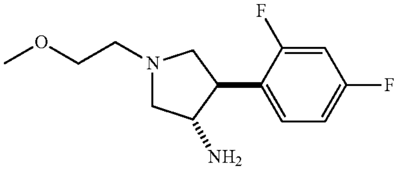 [SMILES: COCCN1C[C@@H](N)[C@H](c2ccc(F)cc2F)C1] | trans-4-(2,4-difluorophenyl)-1-(2-methoxyethyl)pyrrolidin-3-amine | MS (apci) m/z = 256.1 (M + H) |
| L-105 | 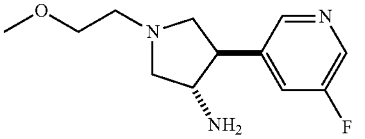 [SMILES: COCCN1C[C@@H](N)[C@H](c2cncc(F)c2)C1] | trans-4-(5-fluoropyridin-3-yl)-1-(2-methoxyethyl)pyrrolidin-3-amine | MS (apci) m/z = 240.1 (M + H) |
| L-106 | 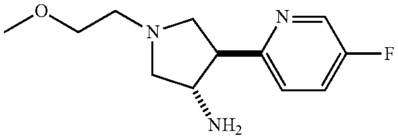 | trans-4-(5-fluoropyridin-2-yl)-1-(2-methoxyethyl)pyrrolidin-3-amine | $^1$H NMR consistent with expected product |
| L-107 | 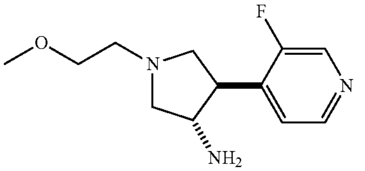 [SMILES: COCCN1C[C@@H](N)[C@H](c2ccncc2F)C1] | trans-4-(3-fluoropyridin-4-yl)-1-(2-methoxyethyl)pyrrolidin-3-amine | Not available |
| L-108 | 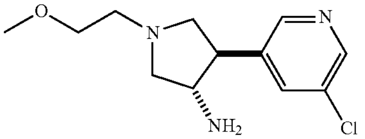 [SMILES: COCCN1C[C@@H](N)[C@H](c2cncc(Cl)c2)C1] | trans-4-(5-chloropyridin-3-yl)-1-(2-methoxyethyl)pyrrolidin-3-amine | MS (apci) m/z = 256.1 (M + H) |
| L-109 | 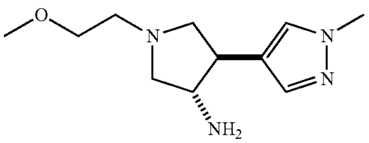 | trans-1-(2-methoxyethyl)-4-(1-methyl-1H-pyrazol-4-yl) pyrrolidin-3-amine | $^1$H NMR consistent with expected product |
| L-110 | 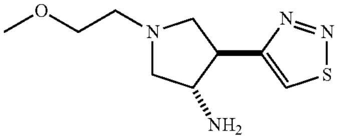 | trans-1-(2-methoxyethyl)-4-(1,2,3-thiadiazol-4-yl)pyrrolidin-3-amine | Not available |

Preparation L-111

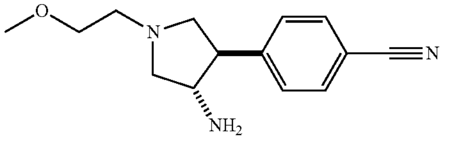

4-(trans-4-amino-1-(2-methoxyethyl)pyrrolidin-3-yl) benzonitrile

Prepared according to the method described in Preparation E1, Steps A to C, replacing 4-fluorobenzaldehyde with 4-formylbenzonitrile in Step A and replacing EtOH and platinum(IV) oxide with MeOH, Zn (dust) and saturated $NH_4Cl$, respectively in Step C. MS (apci) m/z=246.1 (M+H).

Preparation L112

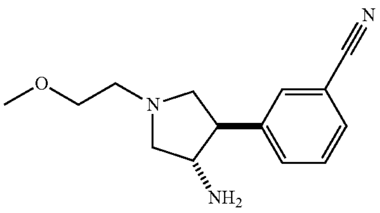

3-(trans-4-amino-1-(2-methoxyethyl)pyrrolidin-3-yl) benzonitrile

Prepared according to the method described in Preparation E1, Steps A to C, replacing 4-fluorobenzaldehyde with 3-formylbenzonitrile in Step A, and replacing EtOH and platinum(IV) oxide with MeOH, Zn (dust) and saturated $NH_4Cl$, respectively, in Step C. MS (apci) m/z=246.2 (M+H).

Preparation M-100

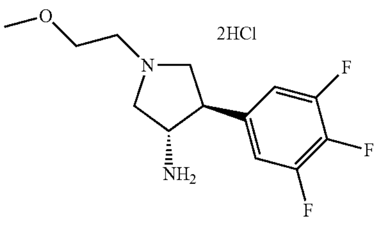

2HCl (3S,4R)-1-(2-methoxyethyl)-4-(3,4,5-trifluorophenyl)pyrrolidin-3-amine dihydrochloride Prepared according to the method described in Preparation B, replacing cinnamoyl chloride with (E)-3-(3,4,5-trifluorophenyl)acryloyl chloride. $^1H$ NMR ($D_2O$) δ 7.06-7.10 (m, 2H), 4.13-4.20 (m, 1H), 3.92-3.99 (m, 2H), 3.71-3.74 (m, 1H), 3.57-3.63 (m, 3H), 3.41-3.49 (m, 3H), 3.25 (s, 3H).

Preparation N-100

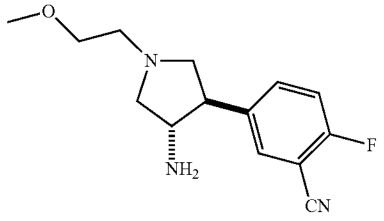

Trans-5-(4-amino-1-(2-methoxyethyl)pyrrolidin-3-yl)-2-fluorobenzonitrile

Step A: (E)-2-fluoro-5-(2-nitrovinyl)benzonitrile

To a solution of 2-fluoro-5-formylbenzonitrile (3.84 g, 25.0 mmol) in 3:1 $CH_3NO_2/CH_3CN$ (25 mL) was added DMAP (0.305 g, 2.50 mmol) and the mixture stirred at ambient temperature for 23 hours. The mixture was cooled on an ice bath and $Ac_2O$ (3.54 mL, 37.5 mmol) was added. The mixture was stirred for 5 minutes, allowed to reach ambient temperature and stirred for 1 hour. The mixture was concentrated to a yellow solid. The solid was suspended in iPrOH (70 mL) and stirred for 10 minutes. The suspension was collected via vacuum filtration, the cake washed with iPrOH and dried in vacuum to afford the title compound as a light tan powder (3.36 g, 70%). $^1H$ NMR ($CDCl_3$) δ 7.96 (d, 1H), 7.79-7.88 (m, 2H), 7.57 (d, 1H), 7.36 (t, 1H).

Step B: Trans-2-fluoro-5-(1-(2-methoxyethyl)-4-nitropyrrolidine-3-yl)benzonitrile Using (E)-2-fluoro-5-(2-nitrovinyl)benzonitrile in Step B of the procedure describe in Preparation E1, the title compound was prepared as light gold syrup (1.56 g, 53%). MS (apci) m/z=294.1 (M+H).

Step C: Trans-5-(4-amino-1-(2-methoxyethyl)pyrrolidin-3-yl)-2-fluorobenzonitrile A solution of trans-2-fluoro-5-(1-(2-methoxyethyl)-4-nitropyrrolidin-3-yl)benzonitrile (450 mg, 1.53 mmol) in MeOH (6.0 mL) was cooled to 0°. Zn dust (1.00 mg, 15.3 mmol) and saturated aqueous $NH_4Cl$ (1.0 mL) were added sequentially and the mixture was stirred for 5 minutes. The mixture was allowed to reach ambient temperature and stirred until complete by LCMS analysis. The mixture was filtered through packed Celite® using MeOH for rinsing and elution and the filtrate was concentrated to a colorless syrup. The syrup was treated with 1M $K_2CO_3$ (15 mL), mixed and extracted with $CH_2Cl_2$ (3×). The combined $CH_2Cl_2$ extracts were dried over $Na_2SO_4$, filtered and concentrated to provide the title compound as a colorless syrup (412 mg, 100%). MS (apci) m/z=264.1 (M+H).

Preparation O-100

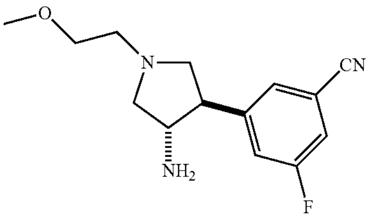

Trans-3-(4-amino-1-(2-methoxyethyl)pyrrolidin-3-yl)-5-fluorobenzonitrile

Step A: 3-fluoro-5-formylbenzonitrile

A solution of 3-bromo-5-fluorobenzonitrile (5.00 g, 25.0 mmol) in dry THF (25 mL) was cooled to 0° C. and 2M iPrMgCl (15.0 mL, 30.0 mmol) in THF was added dropwise over 5 minutes. The mixture was stirred at 0° C. for 15 minutes then at ambient temperature for 1 hour. The mixture was cooled to 0° C. and dry DMF (5.81 mL, 75.0 mmol) was added. The mixture was stirred for 17 hours during which time the temperature reached ambient temperature after 2 hours. The mixture was added to ice water (150 mL) and $Et_2O$ (100 mL). The biphasic mixture was stirred and treated with 6M HCl to aqueous pH=3. The organic layer was removed and the aqueous layer extracted with $Et_2O$ (2×). The combined $Et_2O$ fractions were washed with saturated NaCl and dried over $MgSO_4$/activated carbon. The dried solution was filtered through a $SiO_2$ plug eluting with $Et_2O$. The filtrate was concentrated to give the title compound as a yellow solid that was dried in vacuum (3.68 g, 99%). $^1H$ NMR ($CDCl_3$) δ 10.0 (s, 1H), 8.00 (s, 1H), 7.81-7.86 (m, 1H), 7.62-7.67 (m, 1H).

Step B: Trans-3-(4-amino-1-(2-methoxyethyl)pyrrolidin-3-yl)-5-fluorobenzonitrile The tile compound was prepared using 3-fluoro-5-formylbenzonitrile in the procedure described for the preparation of trans-5-(4-amino-1-(2-methoxyethyl)pyrrolidin-3-yl)-2-fluorobenzonitrile (Preparation N-100). The compound was isolated as a colorless syrup (542 mg, 93%). MS (apci) m/z=264.1 (M+H)

Preparation P-100

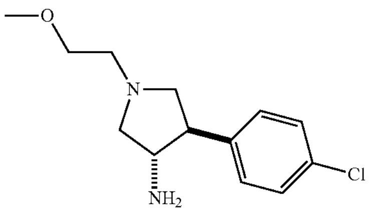

Trans-1-(2-methoxyethyl)-4-(4-chlorophenyl)pyrrolidin-3-amine

Step A: Trans-3-(4-chlorophenyl)-1-(2-methoxyethyl)-4-nitropyrrolidine

Using (E)-1-chloro-4-(2-nitrovinyl)benzene in Step B of the procedure describe in Preparation E1, the title compound was prepared as viscous colorless oil (5.10 g, 64%). MS (apci) m/z=285.0 (M+H).

Step B: Trans-1-(2-methoxyethyl)-4-(4-chlorophenyl)pyrrolidin-3-amine

To a suspension of 2800 Raney Nickel (50 wt % in $H_2O$, 0.873 g, 5.10 mmol) in MeOH (25 mL) was added trans-3-(4-chlorophenyl)-1-(2-methoxyethyl)-4-nitropyrrolidine (2.90 g, 10.2 mmol) in MeOH (25 mL). The mixture was flushed with $H_2$ gas and stirred under a balloon atmosphere of $H_2$ for 16 hours. The mixture was purged with $N_2$ gas and filtered through packed Celite® using MeOH for rinsing and elution. The filtrate was concentrated to a cloudy oil. The oil was dissolved in $CH_2Cl_2$ and dried over $Na_2SO_4$/activated carbon. The solution was filtered and concentrated to provide the title compound as a light gold oil that was dried in vacuum (2.46 g, 95%). MS (apci) m/z=255.1 (M+H).

Preparation F1

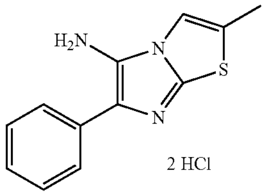

2 HCl 2-methyl-6-phenylimidazo [2,1-b]thiazol-5-amine dihydrochloride

Step A: Preparation of 2-methyl-6-phenyl-N-(2,4,4-trimethylpentan-2-yl)imidazo[2,1-b]thiazol-5-amine To a solution of 5-methylthiazol-2-amine (1.16 g, 10.0 mmol) and benzaldehyde (1.11 mL, 11.0 mmol) in 2:1 DCM-MeOH (30 mL) was added $Sc(OTf)_3$ (0.246 g, 0.500 mmol) and the mixture was stirred at ambient temperature for 30 minutes. 1,1,3,3-tetramethylbutyl isocyanide (2.32 mL, 12.0 mmol) was added and the mixture was stirred at ambient temperature for 24 hours. The mixture was concentrated and the residue was purified by silica column chromatography eluting with a step gradient of DCM, 10% then 20% EtOAc/hexanes. The title compound was obtained as a cream colored solid (3.10 g, 91% yield). $^1H$ NMR ($CDCl_3$) δ 7.80 (d, J=7.5 Hz, 2H), 7.37 (t, J=7.6 Hz., 2H), 7.25 (d, J=8.5 Hz, 1H), 7.08 (s, 1H), 3.10 (br s, 1H), 2.41 (s, 3H), 1.53 (s, 2H), 1.02 (s, 9H), 1.00 (s, 6H) ppm.

Step B: Preparation of 2-methyl-6-phenylimidazo[2,1-b]thiazol-5-amine dihydrochloride To a suspension of 2-methyl-6-phenyl-N-(2,4,4-trimethylpentan-2-yl)imidazo[2,1-b]thiazol-5-amine (3.10 g, 9.08 mmol) in MeOH (90 mL) was added concentrated HCl (80 mL) and the resulting solution was stirred at ambient temperature for 5 hours. The mixture was concentrated and the residual solid was azeotroped with toluene (2×). The solid was washed with 1% MeOH/EtOAc and dried in vacuum to afford the title compound as a faint green powder (2.22 g, 92% yield). $^1H$ NMR ($DMSOd_6$) δ 8.10 (s, 1H), 7.77 (d, J=7.5 Hz, 2H), 7.48 (t, J=7.8 Hz, 2H), 7.32 (t, J=7.4 Hz, 1H), 5.88 (br s, 2H), 2.49 (s, 3H) ppm.

The following intermediates were prepared according to the method of Preparation F1 using the appropriate 2-amino-1-azaheterocycle and aldehyde.

| Preparation# | Structure | Name | Data |
|---|---|---|---|
| F2 | 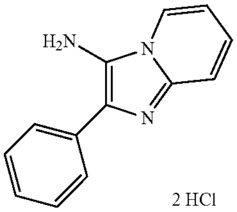 [SMILES: Nc1c(-c2ccccc2)nc2ccccn12] 2 HCl | 2-phenylimidazo[1,2-a]pyridin-3-amine hydrochloride | MS(apci) m/z = 210.3 (M + H) |
| F3 | 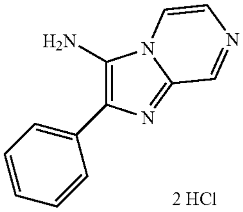 [SMILES: Nc1c(-c2ccccc2)nc2cnccn12] 2 HCl | 2-phenylimidazo[1,2-a]pyrazin-3-amine dihydrochloride | MS(apci) m/z = 211.3 (M + H) |
| F4 | 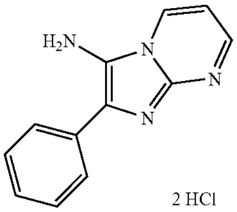 [SMILES: Nc1c(-c2ccccc2)nc2ncccn12] 2 HCl | 2-phenylimidazo[1,2-a]pyrimidin-3-amine dihydrochloride | MS(apci) m/z = 211.3 (M + H) |
| F5 | 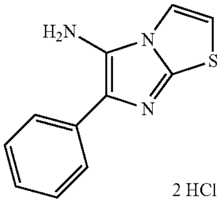 [SMILES: Nc1c(-c2ccccc2)nc2sccn12] 2 HCl | 6-phenylimidazo[2,1-b]thiazol-5-amine dihydrochloride | MS(apci) m/z = 216.0 (M + H) |
| F6 | 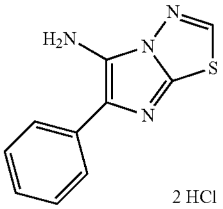 [SMILES: Nc1c(-c2ccccc2)nc2scnn12] 2 HCl | 6-phenylimidazo[2,1-b][1,3,4]thiadiazol-5-amine dihydrochloride | MS(apci) m/z = 217.2 (M + H) |
| F7 | 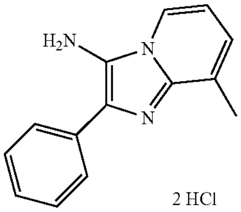 [SMILES: Cc1cccn2c(N)c(-c3ccccc3)nc12] 2 HCl | 8-methyl-2-phenylimidazo[1,2-a]pyridin-3-amine dihydrochloride | MS(apci) m/z = 224.3 (M + H) |
| F8 | 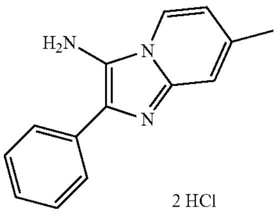 [SMILES: Cc1ccn2c(N)c(-c3ccccc3)nc2c1] 2 HCl | 7-methyl-2-phenylimidazo[1,2-a]pyridin-3-amine dihydrochloride | |

-continued

| Preparation# | Structure | Name | Data |
|---|---|---|---|
| F9 | 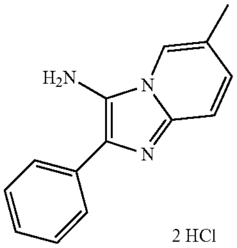 [SMILES: Cc1ccc2nc(-c3ccccc3)c(N)n2c1] 2 HCl | 6-methyl-2-phenylimidazo[1,2-a]pyridin-3-amine dihydrochloride | MS(apci) m/z = 224.2 (M + H) |
| F10 | 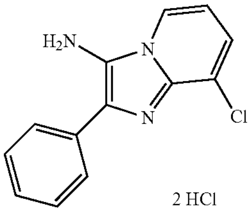 [SMILES: Nc1c(-c2ccccc2)nc2c(Cl)cccn12] 2 HCl | 8-chloro-2-phenylimidazo[1,2-a]pyridin-3-amine dihydrochloride | MS(apci) m/z = 244.2 (M + H) |
| F11 | 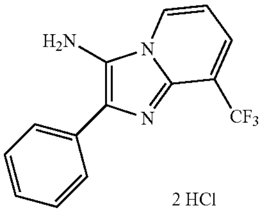 [SMILES: Nc1c(-c2ccccc2)nc2c(C(F)(F)F)cccn12] 2 HCl | 8-trifluoromethyl-2-phenylimidazo[1,2-a]pyridin-3-amine dihydrochloride | MS(apci) m/z = 278.0 (M + H) |
| F12 | 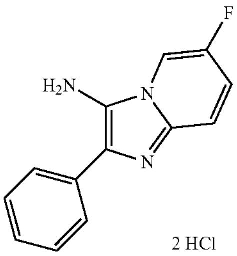 [SMILES: Nc1c(-c2ccccc2)nc2ccc(F)cn12] 2 HCl | 6-fluoro-2-phenylimidazo[1,2-a]pyridin-3-amine dihydrochloride | $^1$H NMR ($DMSOd_6$) δ 9.06 (s, 1H), 7.97-7.82 (m, 4H), 7.57 (t, J = 7.7 Hz, 2H), 7.54 (t, J = 7.4 Hz, 1H), 6.21 (br s, 2H) ppm. |
| F13 | 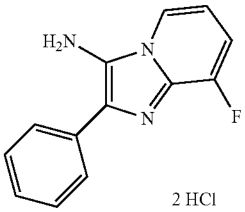 [SMILES: Nc1c(-c2ccccc2)nc2c(F)cccn12] 2 HCl | 8-fluoro-2-phenylimidazo[1,2-a]pyridin-3-amine dihydrochloride | $^1$H NMR ($DMSOd_6$) δ 8.75 (d, J = 6.8 Hz, 1H), 7.96 (d, J = 7.3 Hz, 2H), 7.75 (dd, J = 10.5, 8.0 Hz, 1H), 7.57 (t, J = 7.4 Hz, 2H), 7.48-7.41 (m, 2H) ppm. |
| F14 | 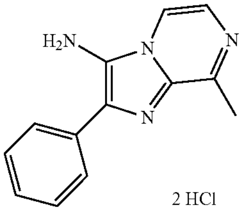 [SMILES: Cc1nccn2c(N)c(-c3ccccc3)nc12] 2 HCl | 8-methyl-2-phenylimidazo[1,2-a]pyrazin-3-amine dihydrochloride | $^1$H NMR ($DMSOd_6$) δ 8.58 (d, J = 5.6 Hz, 1H), 8.01 (d, J = 8.4 Hz, 2H), 7.74 (d, J = 5.6 Hz, 1H), 7.55(t, J = 7.5 Hz, 2H), 7.46 (t, J = 7.4 Hz, 1H), 2.89 (s, 3H) ppm. |

Preparation F15

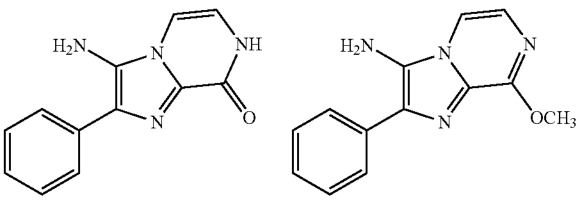

3-amino-2-phenylimidazo[1,2-a]pyrazin-8(7H)-one dihydrochloride and 8-methoxy-2-phenylimidazo[1,2-a]pyrazin-3-amine dihydrochloride Step A: Preparation of 8-methoxy-2-phenyl-N-(2,4,4-trimethylpentan-2-yl)imidazo[1,2-a]pyrazin-3-amine The title compound was prepared utilizing 3-methoxypyrazin-2-amine in the procedure outlined in Preparation F1, Step A. The compound was isolated as a colorless foam (2.80 g, 99% yield). MS (apci) m/z=353.1 (M+H).

Step B: Preparation of 3-amino-2-phenylimidazo[1,2-a]pyrazin-8(7H)-one dihydrochloride 8-methoxy-2-phenyl-N-(2,4,4-trimethylpentan-2-yl)imidazo[1,2-a]pyrazin-3-amine (2.75 g, 7.80 mmol) was dissolved in 1:1 dioxane-anhydrous MeOH (25 mL) and treated with 4M HCl dioxane (50 mL). The mixture was stirred at ambient temperature for 3 hours and was diluted with MTBE (250 mL). The resulting suspension was stirred for 5 minutes and filtered. The collected solid was washed with MTBE and dried in vacuum to afford the title compound as a light yellow powder (1.52 g, 65% yield). MS (apci) m/z=227.0 (M+H).

Step C: Preparation of 8-methoxy-2-phenylimidazo[1,2-a]pyrazin-3-amine dihydrochloride The filtrate from Step B was allowed to stand at ambient temperature for 16 hours. The resulting precipitate was collected via vacuum filtration, washed with MTBE and dried in vacuum to provide the title compound as a yellow solid (101 mg, 4.1% yield). MS (apci) m/z=241.0 (M+H).

Preparation F16

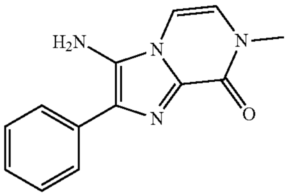

3-amino-7-methyl-2-phenylimidazo[1,2-a]pyrazin-8(7H)-one

A fine suspension of 3-amino-2-phenylimidazo [1,2-a]pyrazin-8(7H)-one dihydrochloride (Preparation F15, 299 mg, 0.999 mmol) in 2:1 $H_2O$-MeOH (10 mL) was treated with 2M NaOH to pH=13. The mixture was stirred vigorously for 2 hours and filtered. The collected solid was washed with $H_2O$ and MeOH and dried in vacuum to provide the free base as a white powder (225 mg, 99% yield). A fine suspension of 3-amino-2-phenylimidazo[1,2-a]pyrazin-8(7H)-one (220 mg, 0.972 mmol) in dry DMF (4 mL) was cooled to 0° C. and LiH (8.54 mg, 1.02 mmol) was added in one portion. The mixture was allowed to reach ambient temperature and was stirred for 1 hour. The mixture was cooled to 0° C. and iodomethane (63.6 μL, 1.02 mmol) was added. The mixture was allowed to reach ambient temperature and stirred for 17 hours. The mixture was diluted with cold $H_2O$ (10 mL) and mixed. The resulting fine white precipitate was collected via vacuum filtration and washed with $H_2O$. The wet solid was suspended in MeOH and concentrated to furnish the title compound as a dry white solid (187 mg, 80% yield). MS (apci) m/z=241.0 (M+H).

Preparation F17

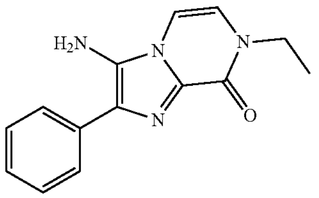

3-amino-7-ethyl-2-phenylimidazo[1,2-a]pyrazin-8(7H)-one

A fine pale-yellow suspension of 3-amino-2-phenylimidazo[1,2-a]pyrazin-8(7H)-one dihydrochloride (Preparation F15, 1.39 g, 4.65 mmol) in MeOH (20 mL) was treated with $H_2O$ (20 mL) and 2M NaOH was added to pH=13. The mixture was sonicated for 1-2 minutes and was stirred at ambient temperature for 1 hour. The solid was collected via vacuum filtration, washed with $H_2O$ and MeOH and dried in vacuum to afford the free-base as a white powder (1.06 g, 101%), white powder. To a solution of 3-amino-2-phenylimidazo[1,2-a]pyrazin-8(7H)-one (226 mg, 0.999 mmol) in dry DMSO (3 mL) was added 1M LiOt-Bu in THF (1.20 mL, 1.20 mmol) over 2 minutes. The mixture was stirred at ambient temperature for 30 minutes and iodoethane (87.9 μL, 1.10 mmol) was added. The reaction mixture was stirred at ambient temperature for 2.5 hours. The mixture was diluted with cold $H_2O$ (10 mL) and stirred for 15 minutes at ambient temperature. The resulting fine white precipitate was collected via vacuum filtration and was washed with $H_2O$ and MTBE. The solid was dried in vacuum to afford the title compound as a white solid (129 mg, 51% yield). MS (apci) m/z=255.0 (M+H).

SYNTHETIC EXAMPLES

Example 1

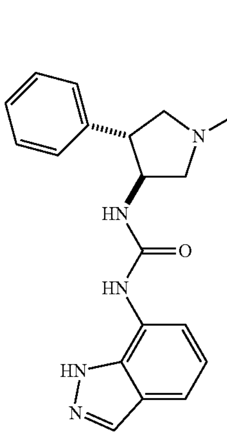

2($CF_3COOH$)

1-(1H-indazol-7-yl)-3-(trans-1-(2-methoxyethyl)-4-phenylpyrrolidin-3-yl)urea di-trifluoroacetate Step A: Preparation of 4-nitrophenyl trans-1-(2-methoxyethyl)-4-phenylpyrrolidin-3-ylcarbamate To a solution of trans-1-(2-methoxyethyl)-4-phenylpyrrolidin-3-amine dihydrochloride [Preparation B] (300 mg, 1.02 mmol) in DCM (10 mL) at 0° C. was added triethylamine (0.71 mL, 5.12 mmol) followed by a solution of 4-nitrophenyl chloroformate (227 mg, 1.13 mmol) in DCM (2 mL). The mixture was stirred at this temperature for 1 hour then partitioned between saturated $NaHCO_3$ (20 mL) and DCM (20 mL). The organic layer was removed and the aqueous layer was extracted with DCM (2×20 mL). The combined organic phases were washed with brine (20 mL), dried over $Na_2SO_4$, filtered and concentrated under vacuum to afford 4-nitrophenyl trans-1-(2-methoxyethyl)-4-phenylpyrrolidin-3-ylcarbamate as a yellow gum which was used directly in the next step assuming 100% yield.

Step B: Preparation of 1-(1H-indazol-7-yl)-3-(trans-1-(2-methoxyethyl)-4-phenylpyrrolidin-3-yl)urea To a solution of 4-nitrophenyl trans-1-(2-methoxyethyl)-4-phenylpyrrolidin-3-ylcarbamate (197 mg, 0.51 mmol) in DCE (3 mL) was added 1H-indazol-7-amine (82 mg, 0.61 mmol) followed by DIEA (267 μL, 1.53 mmol). The reaction mixture was stirred at 60° C. for 16 hours, cooled to ambient temperature and partitioned between saturated $NaHCO_3$ (10 mL) and DCM (10 mL). The organic layer was removed and the aqueous layer was extracted with DCM (2×10 mL). The combined organic phases were washed with brine (10 mL), dried over $Na_2SO_4$ and concentrated under vacuum. The residue was purified by silica column chromatography eluting with 0-10% MeOH/DCM, then by reverse phase HPLC (5-95% ACN/water/0.1% TFA) to afford the title compound (9 mg, 3% yield) as a pale pink solid. MS (apci) m/z=380.3 (M+H).

Example 2

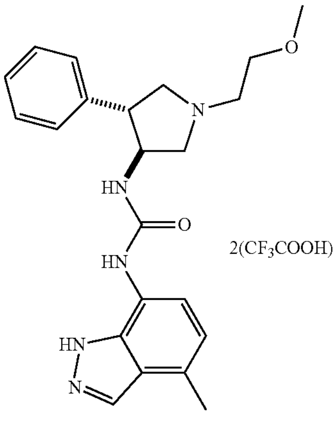 [SMILES: COCCN1C[C@@H](NC(=O)Nc2ccc(C)c3cn[nH]c23)[C@H](c2ccccc2)C1]

2($CF_3COOH$)

1-(trans-1-(2-methoxyethyl)-4-phenylpyrrolidin-3-yl)-3-(4-methyl-1H-indazol-7-yl)urea di-trifluoroacetate Prepared according to the procedure of Example 1, replacing 1H-indazol-7-amine with 4-methyl-1H-indazol-7-amine in Step B. The crude product was purified by silica column chromatography eluting with 2-3% MeOH/DCM, then reverse phase HPLC (5-95% ACN/water/0.1% TFA) to afford the title compound (21 mg, 7% yield) an off-white solid. MS (apci) m/z=394.2 (M+H).

Example 3

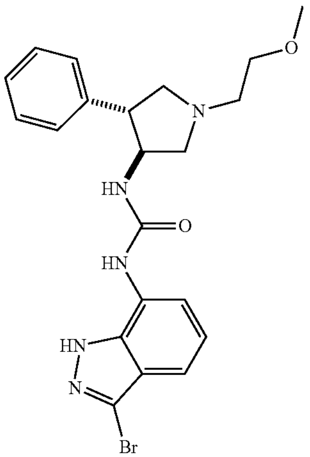 [SMILES: COCCN1C[C@@H](NC(=O)Nc2cccc3c(Br)n[nH]c23)[C@H](c2ccccc2)C1]

1-(3-bromo-1H-indazol-7-yl)-3-(trans-1-(2-methoxyethyl)-4-phenylpyrrolidin-3-yl)urea Step A: Preparation of tert-butyl 3-bromo-7-nitro-1H-indazole-1-carboxylate To a solution of 3-bromo-7-nitro-1H-indazole (1.0 g, 4.13 mmol) in DCM (30 mL) were added $Et_3N$ (633 μL, 4.54 mmol), DMAP (505 mg, 4.13 mmol) and Boc anhydride (992 mg, 4.54 mmol). The mixture was heated at reflux for 16 hours, cooled to ambient temperature and concentrated under vacuum. The residue was purified by silica column chromatography eluting with 9:1 hexanes/EtOAc, to afford tert-butyl 3-bromo-7-nitro-1H-indazole-1-carboxylate (1.16 g, 82% yield) as a yellow solid. $^{1}$H NMR ($CDCl_3$) δ 8.08 (d, J=7.7 Hz, 1H), 7.93 (d, J=8.0 Hz, 1H), 7.50 (t, J=7.9 Hz, 1H), 1.65 (s, 9H) ppm.

Step B: Preparation of tert-butyl 7-amino-3-bromo-1H-indazole-1-carboxylate

To a solution of tert-butyl 3-bromo-7-nitro-1H-indazole-1-carboxylate (1.16 g, 3.39 mmol) in methanol (20 mL) under $N_2$ atmosphere was added 2800 Raney nickel (290 mg, 3.39 mmol) in water (2 mL). The mixture was hydrogenated under a double-walled balloon atmosphere of $H_2$ for 18 hours and filtered through GF paper using methanol-water for wash and elution. The filtrate was concentrated, and the residue was dried with a toluene azeotrope then in vacuum. The residue was purified by silica column chromatography eluting with 9:1 hexanes/EtOAc to afford tert-butyl 7-amino-3-bromo-1H-indazole-1-carboxylate (511 mg, 48% yield) as a white, crystalline solid. MS (apci) m/z=312.9 (M+H).

Step C: Preparation 1-(3-bromo-1H-indazol-7-yl)-3-(trans-1-(2-methoxyethyl)-4-phenylpyrrolidin-3-yl) urea Prepared according to the procedure of Example 1, replacing 1H-indazol-7-amine with tert-butyl 7-amino-3-bromo-1H-indazole-1-carboxylate in Step B. The crude material was purified by silica column chromatography eluting with 2% MeOH/DCM to afford the title compound (23 mg, 15% yield) as a pale yellow foam. MS (apci) m/z=458.1 (M+).

Example 4

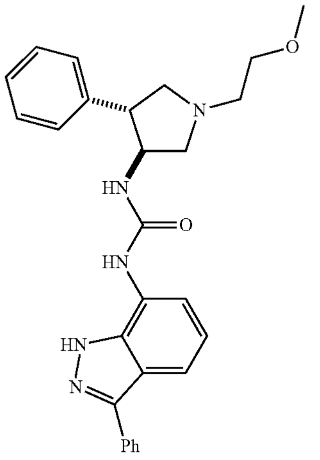

1-(trans-1-(2-methoxyethyl)-4-phenylpyrrolidin-3-yl)-3-(3-phenyl-1H-indazol-7-yl)urea Step A: Preparation of 3-bromo-1-(4-methoxybenzyl)-7-nitro-1H-indazole To a solution of 3-bromo-7-nitro-1H-indazole (1.0 g, 4.13 mmol) in acetone (30 mL) at 0° C. was added freshly powdered potassium hydroxide (348 mg, 6.2 mmol). After stirring for 15 minutes, 4-methoxy benzyl chloride (561 μL, 4.13 mmol) was added dropwise. The mixture was stirred at ambient temperature for 2 hours then at reflux for 16 hours. The cooled mixture was concentrated then partitioned between water (50 mL) and EtOAc (50 mL). The organic layer was removed and the aqueous phase was extracted with EtOAc (2×30 mL) The combined organic phases were washed with brine (30 mL), dried over $Na_2SO_4$, filtered and concentrated under vacuum. The residue was purified by silica column chromatography eluting with 19:1 hexanes/EtOAc to afford 3-bromo-1-(4-methoxybenzyl)-7-nitro-1H-indazole (569 mg, 38% yield) as a bright yellow crystalline solid. $^{1}$H NMR ($CDCl_3$) δ 8.06 (d, J=7.7 Hz, 1H), 7.93 (d, J=8.0 Hz, 1H), 7.26 (m, 1H), 6.98 (d, J=8.6 Hz, 2H), 6.75 (d, J=8.6 Hz, 2H), 5.78 (s, 2H), 3.73 (s, 3H) ppm.

Step B: Preparation of 1-(4-methoxybenzyl)-7-nitro-3-phenyl-1H-indazole

3-Bromo-1-(4-methoxybenzyl)-7-nitro-1H-indazole (100 mg, 0.28 mmol) was combined with phenyl boronic acid (50.5 mg, 0.41 mmol), sodium carbonate (88 mg, 0.83 mmol) and $Pd(PPh_3)_4$ (32 mg, 0.03 mmol) in 1:1 DME-$H_2O$ (4 mL). The mixture was purged with $N_2$ and stirred in a sealed tube at 90° C. for 16 hours. The cooled mixture was filtered through GF paper with EtOAc wash and the filtrate partitioned between EtOAc (10 mL) and saturated $NaHCO_3$ (10 mL). The organic layer was removed and the aqueous layer was extracted with EtOAc (2×10 mL). The combined organic phases were washed with brine (10 mL), dried over $Na_2SO_4$, filtered and concentrated under vacuum. The residue was purified by silica column chromatography eluting with 9:1 hexanes/EtOAc, then again with 19:1 hexanes/EtOAc, to afford 1-(4-methoxybenzyl)-7-nitro-3-phenyl-1H-indazole (51 mg, 51% yield) as a bright yellow solid. MS (apci) m/z=360.2 (M+H).

Step C: Preparation of 1-(4-methoxybenzyl)-3-phenyl-1H-indazol-7-amine

To a suspension of 1-(4-methoxybenzyl)-7-nitro-3-phenyl-1H-indazole (51 mg, 0.14 mmol) in MeOH (5 mL) under $N_2$ atmosphere was added 10% Pd/C (wet, Degussa type, 10 mg). The mixture was hydrogenated under double wall balloon atmosphere of $H_2$ for 16 hours, filtered through GF paper and the filtrate concentrated under vacuum to afford 1-(4-methoxybenzyl)-3-phenyl-1H-indazol-7-amine (41.7 mg, 89% yield) as pale purple gum. MS (apci) m/z=329.9 (M+H).

Step D: Preparation of phenyl (1-(4-methoxybenzyl)-3-phenyl-1H-indazol-7-yl)carbamate To a solution of 1-(4-methoxybenzyl)-3-phenyl-1H-indazol-7-amine (41.7 mg, 0.13 mmol) in EtOAc (2 mL) was added 2 M NaOH (0.13 mL, 0.25 mmol) followed by phenyl chloroformate (22 μL, 0.18 mmol). The mixture was stirred vigorously for 16 hours then partitioned between EtOAc (10 mL) and water (10 mL). The organic layer was removed and the aqueous layer was extracted with EtOAc (2×10 mL). The combined organic phases were washed with brine (10 mL), dried over $Na_2SO_4$, filtered and concentrated under vacuum to afford phenyl (1-(4-methoxybenzyl)-3-phenyl-1H-indazol-7-yl)carbamate (53 mg, 93% yield) as a cream solid. MS (apci) m/z=450.0 (M+H).

Step E: Preparation of 1-(1-(4-methoxybenzyl)-3-phenyl-1H-indazol-7-yl)-3-(trans-1-(2-methoxyethyl)-4-phenylpyrrolidin-3-yl)urea To a solution of trans-1-(2-methoxyethyl)-4-phenylpyrrolidin-3-amine dihydrochloride [Preparation B] (30 mg, 0.10 mmol) and phenyl (1-(4-methoxybenzyl)-3-phenyl-1H-indazol-7-yl)carbamate (50.6 mg, 0.11 mmol) in DMA (3 mL) at 0° C. was added DIEA (62 μL, 0.36 mmol). The mixture was stirred at ambient temperature for 16 hours and partitioned between saturated $NH_4Cl$ (20 mL) and EtOAc (10 mL) The organic layer was removed and the aqueous layer extracted with EtOAc (2×10 mL). The combined organic phases were washed with water (5×10 mL) and brine (10 mL), dried over $Na_2SO_4$, filtered and concentrated under vacuum. The residue was purified by silica column chromatography eluting with 2.5% MeOH/DCM to afford 1-(1-(4-methoxybenzyl)-3-phenyl-1H-indazol-7-yl)-3-(trans-1-(2-methoxyethyl)-4-phenylpyrrolidin-3-yl)urea (44 mg, 75% yield) as a white solid. MS (apci) m/z=576.1 (M+H).

Step F: Preparation of 1-(trans-1-(2-methoxyethyl)-4-phenylpyrrolidin-3-yl)-3-(3-phenyl-1H-indazol-7-yl)urea A solution of 1-(1-(4-methoxybenzyl)-3-phenyl-1H-indazol-7-yl)-3-(trans-1-(2-methoxyethyl)-4-phenylpyrrolidin-3-yl)urea (44 mg, 0.076 mmol) in TFA (2 mL) was stirred at reflux for 2 hours then cooled and concentrated. The residue was partitioned between 1N NaOH (10 mL) and DCM (10 mL) and the organic layer was removed. The aqueous layer was extracted with DCM (2×10 mL) and the combined organic phases were washed with brine (10 mL), dried over $Na_2SO_4$, filtered and concentrated under vacuum. The residue was purified by silica column chromatography eluting with 2-5% MeOH/DCM to afford the title compound (28.8 mg, 83% yield) as a colorless glass. MS (apci) m/z=456.2 (M+H).

Example 5

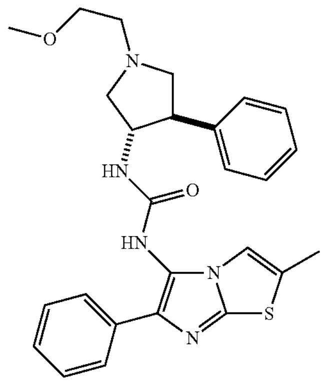

1-((trans)-1-(2-methoxyethyl)-4-phenylpyrrolidin-3-yl)-3-(2-methyl-6-phenylimidazo[2,1-b]thiazol-5-yl)urea To a fine suspension of 2-methyl-6-phenylimidazo[2,1-b]thiazol-5-amine hydrochloride (Preparation F1, 26.6 mg, 0.100 mmol) in dry DMF (0.40 mL) was added DIEA (57.5 μL, 0.330 mmol) and the mixture was stirred at ambient temperature for 5 minutes (homogeneous solution). CDI (35.7 mg, 0.220 mmol) was added in one portion and the mixture was stirred at ambient temperature for 3 hours. To the mixture was added a solution of trans-1-(2-methoxyethyl)-4-phenyl-3-amino-pyrrolidine dihydrochloride (Preparation B, 64.6 mg, 0.220 mmol) and DIEA (57.5 μL, 0.330 mmol) in dry DMF (0.25 mL) The mixture was stirred at ambient temperature for 17 hours and was added to $H_2O$ (4 mL) with stirring. The mixture was extracted with EtOAc (3×) and the combined extracts washed with saturated aqueous NaCl (2×). The EtOAc solution was dried over $MgSO_4$/activated charcoal, filtered through packed Celite® and concentrated. The residue was purified by silica column chromatography eluting with a step gradient of EtOAc, 2% then 5% (9:1 MeOH/$NH_4OH$)/EtOAc to provide a colorless glass. The glass was dissolved in 1:1 DCM/hexanes and the solution concentrated to give the title compound as a white solid (34 mg, 71% yield). MS (apci) m/z=476.1 (M+H).

The following compounds were prepared according the method used for the synthesis of Example 5 using appropriate starting materials, reaction solvent and eluent for column chromatography.

| Example # | Structure | Name | Data |
|---|---|---|---|
| 6 | 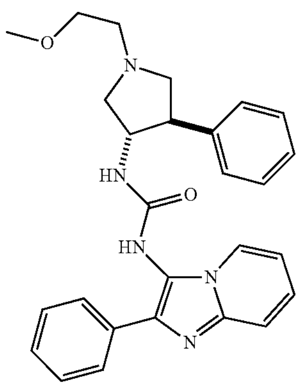 [SMILES: COCCN1C[C@@H](NC(=O)Nc2c(-c3ccccc3)nc3ccccn23)[C@H](c2ccccc2)C1] | 1-((trans)-1-(2-methoxyethyl)-4-phenylpyrrolidin-3-yl)-3-(2-phenylimidazo[1,2-a]pyridin-3-yl)urea | MS(apci) m/z = 456.1 (M + H) |

-continued

| Example # | Structure | Name | Data |
| --- | --- | --- | --- |
| 7 | 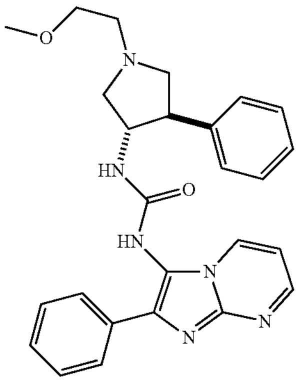 [SMILES: COCCN1C[C@@H](NC(=O)Nc2c(-c3ccccc3)nc3ncccn23)[C@H](c2ccccc2)C1] | 1-((trans)-1-(2-methoxyethyl)-4-phenylpyrrolidin-3-yl)-3-(2-phenylimidazo[1,2-a]pyrimidin-3-yl)urea | MS(apci) m/z = 455.3 (M − H) |
| 8 | 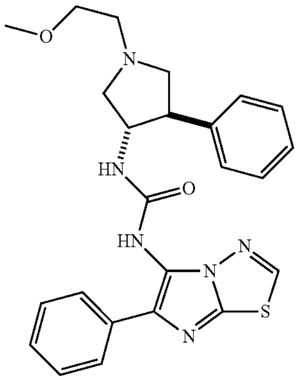 [SMILES: COCCN1C[C@@H](NC(=O)Nc2c(-c3ccccc3)nc3scnn23)[C@H](c2ccccc2)C1] | 1-((trans)-1-(2-methoxyethyl)-4-phenylpyrrolidin-3-yl)-3-(6-phenylimidazo[2,1-b][1,3,4]thiadiazol-5-yl)urea | MS(apci) m/z = 463.1 (M + H) |
| 9 | 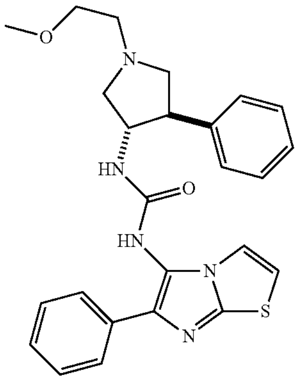 [SMILES: COCCN1C[C@@H](NC(=O)Nc2c(-c3ccccc3)nc3sccn23)[C@H](c2ccccc2)C1] | 1-((trans)-1-(2-methoxyethyl)-4-phenylpyrrolidin-3-yl)-3-(6-phenylimidazo[2,1-b]thiazol-5-yl)urea | MS(apci) m/z = 462.2 (M + H) |
| 10 | 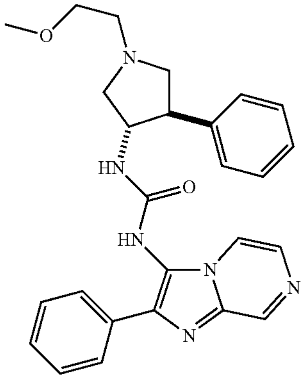 [SMILES: COCCN1C[C@@H](NC(=O)Nc2c(-c3ccccc3)nc3cnccn23)[C@H](c2ccccc2)C1] | 1-((trans)-1-(2-methoxyethyl)-4-phenylpyrrolidin-3-yl)-3-(2-phenylimidazo[1,2-a]pyrazin-3-yl)urea | MS(apci) m/z = 457.2 (M + H) |

-continued

| Example # | Structure | Name | Data |
|---|---|---|---|
| 11 | 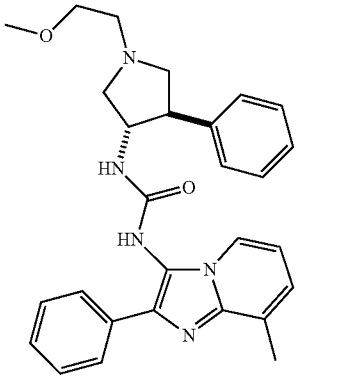 [SMILES: COCCN1C[C@@H](NC(=O)Nc2c(-c3ccccc3)nc3c(C)cccn23)[C@H](c2ccccc2)C1] | 1-((trans)-1-(2-methoxyethyl)-4-phenylpyrrolidin-3-yl)-3-(8-methyl-2-phenylimidazo[1,2-a]pyridin-3-yl)urea | MS(apci) m/z = 470.1 (M + H) |
| 12 | 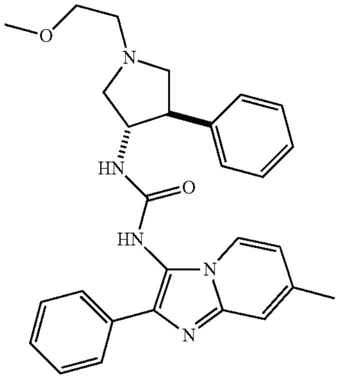 | 1-((trans)-1-(2-methoxyethyl)-4-phenylpyrrolidin-3-yl)-3-(7-methyl-2-phenylimidazo[1,2-a]pyridin-3-yl)urea | MS(apci) m/z = 470.1 (M + H) |
| 13 | 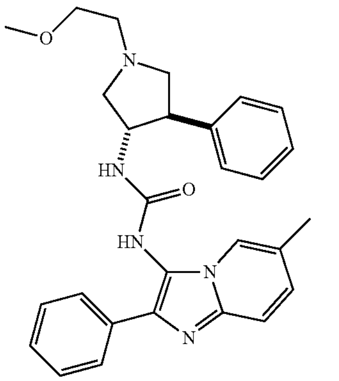 | 1-((trans)-1-(2-methoxyethyl)-4-phenylpyrrolidin-3-yl)-3-(6-methyl-2-phenylimidazo[1,2-a]pyridin-3-yl)urea | MS(apci) m/z = 470.1 (M + H) |
| 14 | 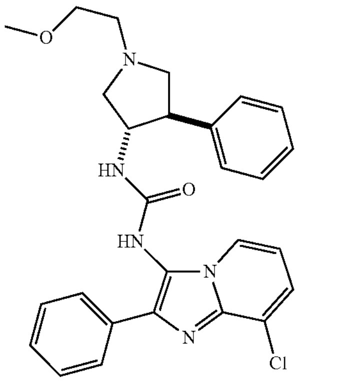 [SMILES: COCCN1C[C@@H](NC(=O)Nc2c(-c3ccccc3)nc3c(Cl)cccn23)[C@H](c2ccccc2)C1] | 1-(8-chloro-2-phenylimidazo[1,2-a]pyridin-3-yl)-3-((trans)-1-(2-methoxyethyl)-4-phenylpyrrolidin-3-yl)urea | MS(apci) m/z = 490.1 (M + H) |

-continued

| Example # | Structure | Name | Data |
|---|---|---|---|
| 15 | 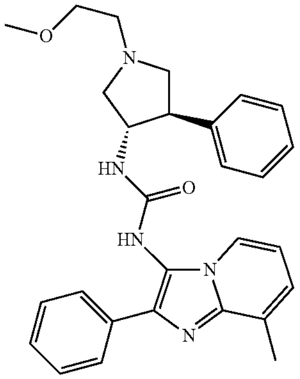 [SMILES: COCCN1C[C@@H](NC(=O)Nc2c(-c3ccccc3)nc3c(C)cccn23)[C@H](c2ccccc2)C1] | 1-((3S,4R)-1-(2-methoxyethyl)-4-phenylpyrrolidin-3-yl)-3-(8-methyl-2-phenylimidazo[1,2-a]pyridin-3-yl)urea | MS(apci) m/z = 470.3 (M + H) |
| 16 | 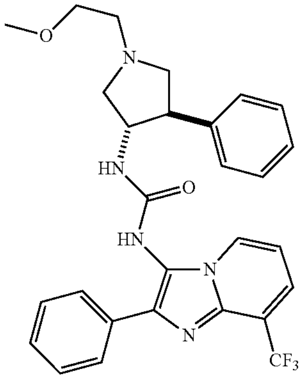 [SMILES: COCCN1C[C@@H](NC(=O)Nc2c(-c3ccccc3)nc3c(C(F)(F)F)cccn23)[C@H](c2ccccc2)C1] | 1-((trans)-1-(2-methoxyethyl)-4-phenylpyrrolidin-3-yl)-3-(2-phenyl-8-(trifluoromethyl)imidazo[1,2-a]pyridin-3-yl)urea | MS(apci) m/z = 524.2 (M + H) |
| 17 | 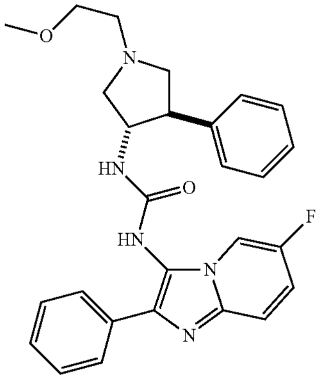 [SMILES: COCCN1C[C@@H](NC(=O)Nc2c(-c3ccccc3)nc3ccc(F)cn23)[C@H](c2ccccc2)C1] | 1-(6-fluoro-2-phenylimidazo[1,2-a]pyridin-3-yl)-3-((trans)-1-(2-methoxyethyl)-4-phenylpyrrolidin-3-yl)urea | MS(apci) m/z = 474.2 (M + H) |
| 18 | 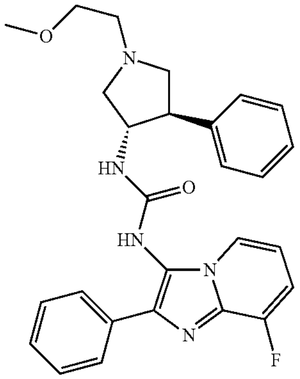 [SMILES: COCCN1C[C@@H](NC(=O)Nc2c(-c3ccccc3)nc3c(F)cccn23)[C@H](c2ccccc2)C1] | 1-(8-fluoro-2-phenylimidazo[1,2-a]pyridin-3-yl)-3-((3S,4R)-1-(2-methoxyethyl)-4-phenylpyrrolidin-3-yl)urea | MS(apci) m/z = 474.1 (M + H) |

-continued

| Example # | Structure | Name | Data |
|---|---|---|---|
| 19 | 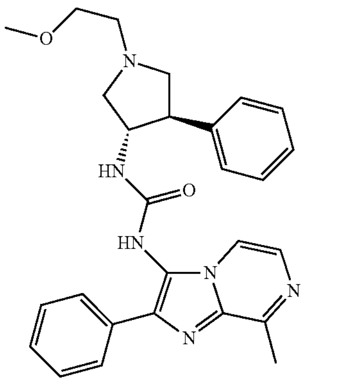 [SMILES: COCCN1C[C@@H](NC(=O)Nc2c(-c3ccccc3)nc3c(C)nccn23)[C@H](c2ccccc2)C1] | 1-((3S,4R)-1-(2-methoxyethyl)-4-phenylpyrrolidin-3-yl)-3-(8-methyl-2-phenylimidazo[1,2-a]pyrazin-3-yl)urea | MS(apci) m/z = 471.3 (M + H) |
| 20 | 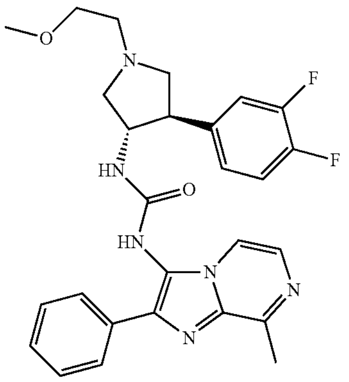 [SMILES: COCCN1C[C@@H](NC(=O)Nc2c(-c3ccccc3)nc3c(C)nccn23)[C@H](c2ccc(F)c(F)c2)C1] | 1-((3S,4R)-4-(3,4-difluorophenyl)-1-(2-methoxyethyl)pyrrolidin-3-yl)-3-(8-methyl-2-phenylimidazo[1,2-a]pyrazin-3-yl)urea | MS(apci) m/z = 507.0 (M + H) |
| 21 | 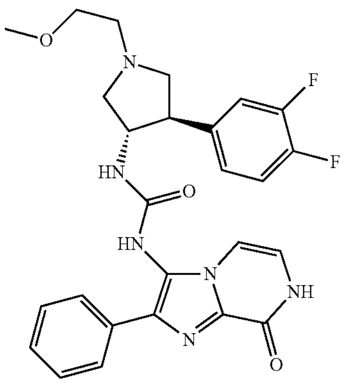 [SMILES: COCCN1C[C@@H](NC(=O)Nc2c(-c3ccccc3)nc3c(=O)[nH]ccn23)[C@H](c2ccc(F)c(F)c2)C1] | 1-((3S,4R)-4-(3,4-difluorophenyl)-1-(2-methoxyethyl)pyrrolidin-3-yl)-3-(8-oxo-2-phenyl-7,8-dihydroimidazo[1,2-a]pyrazin-3-yl)urea | MS(apci) m/z = 509.0 (M + H) |
| 22 | 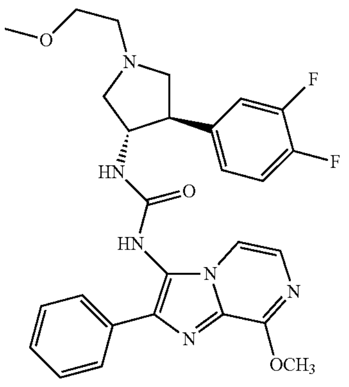 [SMILES: COCCN1C[C@@H](NC(=O)Nc2c(-c3ccccc3)nc3c(OC)nccn23)[C@H](c2ccc(F)c(F)c2)C1] | 1-((3S,4R)-4-(3,4-difluorophenyl)-1-(2-methoxyethyl)pyrrolidin-3-yl)-3-(8-methoxy-2-phenylimidazo[1,2-a]pyrazin-3-yl)urea | MS(apci) m/z = 523.1 (M + H) |

-continued

| Example # | Structure | Name | Data |
|---|---|---|---|
| 23 | 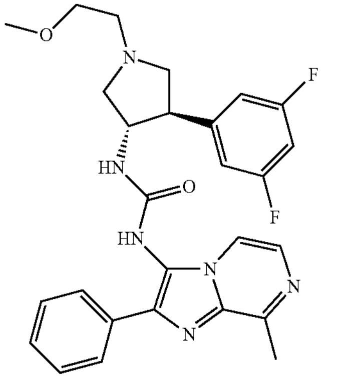 [SMILES: COCCN1C[C@@H](NC(=O)Nc2c(-c3ccccc3)nc3c(C)nccn23)[C@H](c2cc(F)cc(F)c2)C1] | 1-((3S,4R)-4-(3,5-difluorophenyl)-1-(2-methoxyethyl)pyrrolidin-3-yl)-3-(8-methyl-2-phenylimidazo[1,2-a]pyrazin-3-yl)urea | MS(apci) m/z = 507.1 (M + H) |
| 24 | 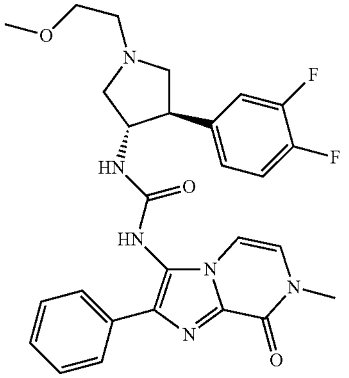 | 1-((3S,4R)-4-(3,4-difluorophenyl)-1-(2-methoxyethyl)pyrrolidin-3-yl)-3-(7-methyl-8-oxo-2-phenyl-7,8-dihydroimidazo[1,2-a]pyrazin-3-yl)urea | MS(apci) m/z = 523.1 (M + H) |
| 25 | 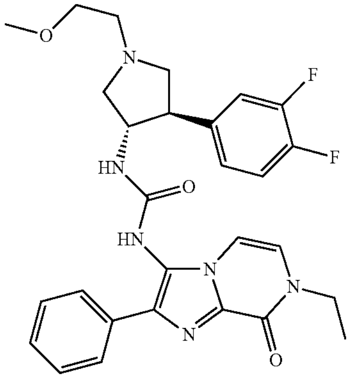 [SMILES: CCn1ccn2c(NC(=O)N[C@@H]3CN(CCOC)C[C@H]3c3ccc(F)c(F)c3)c(-c3ccccc3)nc2c1=O] | 1-((3S,4R)-4-(3,4-difluorophenyl)-1-(2-methoxyethyl)pyrrolidin-3-yl)-3-(7-ethyl-8-oxo-2-phenyl-7,8-dihydroimidazo[1,2-a]pyrazin-3-yl)urea | MS(apci) m/z = 537.0 (M + H) |
| 26 | 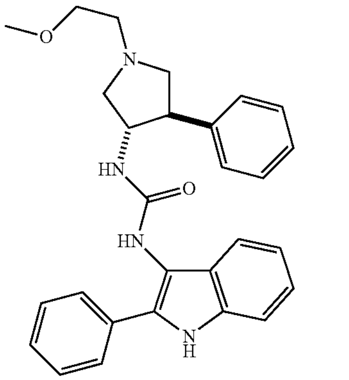 [SMILES: COCCN1C[C@@H](NC(=O)Nc2c(-c3ccccc3)[nH]c3ccccc23)[C@H](c2ccccc2)C1] | 1-((trans)-1-(2-methoxyethyl)-4-phenylpyrrolidin-3-yl)-3-(2-phenyl-1H-indol-3-yl)urea | MS(apci) m/z = 455.1 (M + H) |

-continued

| Example # | Structure | Name | Data |
|---|---|---|---|
| 27 | 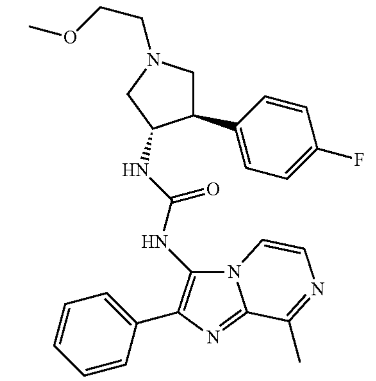 [SMILES: COCCN1C[C@@H](NC(=O)Nc2c(-c3ccccc3)nc3c(C)nccn23)[C@H](c2ccc(F)cc2)C1] | 1-((3S,4R)-4-(4-fluorophenyl)-1-(2-methoxyethyl)pyrrolidin-3-yl)-3-(8-methyl-2-phenylimidazo[1,2-a]pyrazin-3-yl)urea | MS (apci) m/z = 489.1 (M + H) |

Example 28

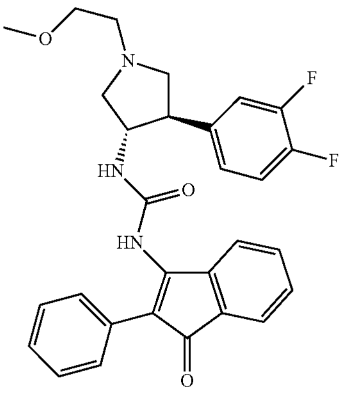 [SMILES: COCCN1C[C@@H](NC(=O)NC2=C(c3ccccc3)C(=O)c3ccccc32)[C@H](c2ccc(F)c(F)c2)C1]

1-((3S,4R)-4-(3,4-difluorophenyl)-1-(2-methoxyethyl)pyrrolidin-3-yl)-3-(1-oxo-2-phenyl-1H-inden-3-yl)urea To a suspension of 3-amino-2-phenyl-1H-inden-1-one (50 mg, 0.23 mmol) in DCM (2.3 mL) at 0° C. was added DIEA (197 μL, 1.1 mmol) followed by triphosgene (27 mg, 0.090 mmol) in one portion. The reaction was allowed to warm to ambient temperature and stirred for 10 minutes. (3S,4R)-4-(3,4-difluorophenyl)-1-(2-methoxyethyl)pyrrolidin-3-amine dihydrochloride (74 mg, 0.23 mmol) was then introduced. After stirred at ambient temperature for 16 hours, the reaction mixture was washed with saturated $NH_4Cl$ (2×2 mL), water and brine (2 mL each), then filtered through a Phase-Separator frit and concentrated. The crude was triturated with acetonitrile (1 mL) and filtered. The filtrate was purified by reverse-phase chromatography (C18, eluent 5 to 70% acetonitrile/water) to yield the product as brown oil. MS (apci) m/z=504.2 (M+H).

What is claimed is:

1. A compound of Formula I:

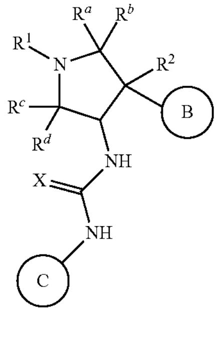

I or stereoisomers, tautomers, or pharmaceutically acceptable salts, solvates or prodrugs thereof, wherein:

Ring B and the NH—C(═X)—NH moiety are in the trans configuration;

$R^a$, $R^b$, $R^c$ and $R^d$ are H;

X is O;

$R^1$ is (1-3C alkoxy)(1-6C)alkyl;

$R^2$ is H;

Ring B is $Ar^1$;

$Ar^1$ is phenyl optionally substituted with one or more substituents independently selected from halogen;

Ring C is selected from formulas C-2, C-3 and C-9

C-2

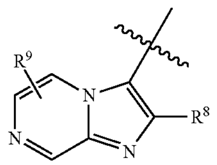

C-3

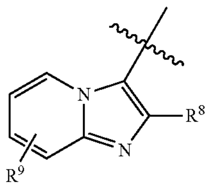

-continued

C-9

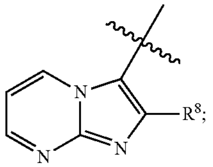

and $R^8$ is phenyl; and $R^9$ is H, halogen, (1-6C)alkyl [optionally substituted with one to five fluoros] or (1-6C)alkoxy.

2. A compound according to claim 1, wherein Ring B and the —NH—C(═X)—NH— moiety of Formula I are trans in the absolute configuration shown in structure C:

C

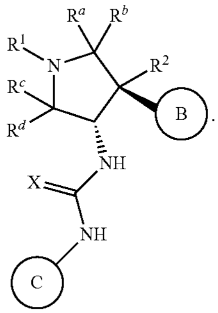

3. A compound according to claim 1, wherein ring B and the —NH—C(═X)—NH— moiety of Formula I are trans in the absolute configuration shown in structure D:

D

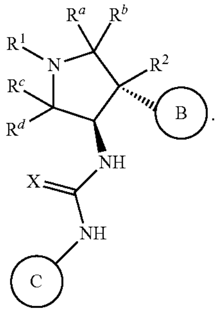

4. A compound of claim 1, selected from 1-((trans)-1-(2-methoxyethyl)-4-phenylpyrrolidin-3-yl)-3-(2-phenylimidazo[1,2-a]pyridin-3-yl)urea;

1-((trans)-1-(2-methoxyethyl)-4-phenylpyrrolidin-3-yl)-3-(2-phenylimidazo[1,2-a]pyrimidin-3-yl)urea;

1-((trans)-1-(2-methoxyethyl)-4-phenylpyrrolidin-3-yl)-3-(2-phenylimidazo[1,2-a]pyrazin-3-yl)urea;

1-((trans)-1-(2-methoxyethyl)-4-phenylpyrrolidin-3-yl)-3-(8-methyl-2-phenylimidazo[1,2-a]pyridin-3-yl)urea;

1-((trans)-1-(2-methoxyethyl)-4-phenylpyrrolidin-3-yl)-3-(7-methyl-2-phenylimidazo[1,2-a]pyridin-3-yl)urea;

1-((trans)-1-(2-methoxyethyl)-4-phenylpyrrolidin-3-yl)-3-(6-methyl-2-phenylimidazo[1,2-a]pyridin-3-yl)urea;

1-(8-chloro-2-phenylimidazo[1,2-a]pyridin-3-yl)-3-((trans)-1-(2-methoxyethyl)-4-phenylpyrrolidin-3-yl)urea;

1-((3S,4R)-1-(2-methoxyethyl)-4-phenylpyrrolidin-3-yl)-3-(8-methyl-2-phenylimidazo[1,2-a]pyridin-3-yl)urea;

1-((trans)-1-(2-methoxyethyl)-4-phenylpyrrolidin-3-yl)-3-(2-phenyl-8-(trifluoromethyl)imidazo[1,2-a]pyridin-3-yl)urea;

1-(6-fluoro-2-phenylimidazo[1,2-a]pyridin-3-yl)-3-((trans)-1-(2-methoxyethyl)-4-phenylpyrrolidin-3-yl)urea;

1-(8-fluoro-2-phenylimidazo[1,2-a]pyridin-3-yl)-3-((3S,4R)-1-(2-methoxyethyl)-4-phenylpyrrolidin-3-yl)urea;

1-((3S,4R)-1-(2-methoxyethyl)-4-phenylpyrrolidin-3-yl)-3-(8-methyl-2-phenylimidazo[1,2-a]pyrazin-3-yl)urea;

1-((3S,4R)-4-(3,4-difluorophenyl)-1-(2-methoxyethyl)pyrrolidin-3-yl)-3-(8-methyl-2-phenylimidazo[1,2-a]pyrazin-3-yl)urea;

1-((3S,4R)-4-(3,4-difluorophenyl)-1-(2-methoxyethyl)pyrrolidin-3-yl)-3-(8-methoxy-2-phenylimidazo[1,2-a]pyrazin-3-yl)urea;

1-((3S,4R)-4-(3,5-difluorophenyl)-1-(2-methoxyethyl)pyrrolidin-3-yl)-3-(8-methyl-2-phenylimidazo[1,2-a]pyrazin-3-yl)urea;

or a pharmaceutically acceptable salt thereof.

5. A pharmaceutical composition, which comprises a compound of Formula I as defined in claim 1 or a pharmaceutically acceptable salt thereof, and a pharmaceutically acceptable diluent or carrier.

6. A process for the preparation of a compound of claim 1, which comprises:

(a) coupling a corresponding compound having the formula II

II

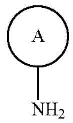

with a corresponding compound having the formula III

III

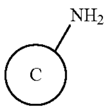

in the presence carbonyldiimidazole or triphosgene and a base; or (c) coupling a corresponding compound having the formula II

II

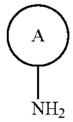

with a corresponding compound having the formula IV

IV

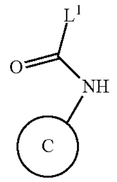

where $L^1$ is a leaving group, in the presence of a base; or (d) coupling a corresponding compound having the formula V

V

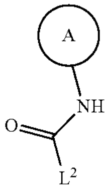

where $L^2$ is a leaving group, with a corresponding compound having the formula III

III

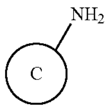

in the presence of a base; or (e) activating a corresponding compound having the formula VI

VI

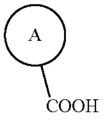

with diphenylphosphoryl azide followed by coupling the activated intermediate with a corresponding compound having the formula III

III

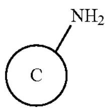

in the presence a base; or (f) coupling a corresponding compound having the formula II

II

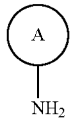

with a corresponding compound having the formula VII

VII

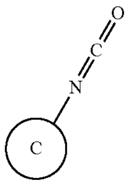

in the presence of a base; or (g) coupling a corresponding compound having the formula VIII

VIII

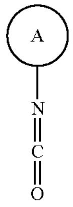

with a corresponding compound having the formula III

III

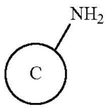

in the presence of a base; and optionally removing protecting groups and optionally preparing a pharmaceutically acceptable salt thereof, wherein in any of the above methods (a), (c), (d), (e), (f), or (g), the ring A is

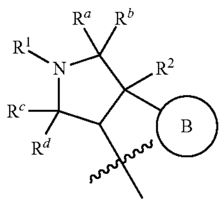

where $R^1$, $R^2$, Ring B, $R^a$, $R^b$, $R^c$ and $R^d$ are as defined in claim 1.

* * * * *